United States Patent
Lucks et al.

(10) Patent No.: US 12,203,144 B2
(45) Date of Patent: Jan. 21, 2025

(54) ANALYTES' DETECTION USING REGULATED IN VITRO TRANSCRIPTION

(71) Applicant: Northwestern University, Evanston, IL (US)

(72) Inventors: Julius B. Lucks, Evanston, IL (US); Khalid K. Alam, Evanston, IL (US); Jaeyoung K. Jung, Evanston, IL (US)

(73) Assignee: Northwestern University, Evanston, IL (US)

( * ) Notice: Subject to any disclaimer, the term of this patent is extended or adjusted under 35 U.S.C. 154(b) by 867 days.

(21) Appl. No.: 17/309,240

(22) PCT Filed: Nov. 11, 2019

(86) PCT No.: PCT/US2019/060790
§ 371 (c)(1),
(2) Date: May 10, 2021

(87) PCT Pub. No.: WO2020/097610
PCT Pub. Date: May 14, 2020

(65) Prior Publication Data
US 2022/0017977 A1   Jan. 20, 2022

Related U.S. Application Data

(60) Provisional application No. 62/758,242, filed on Nov. 9, 2018.

(51) Int. Cl.
| | |
|---|---|
| *C12Q 1/6897* | (2018.01) |
| *C12N 9/12* | (2006.01) |
| *C12N 15/115* | (2010.01) |
| *C12Q 1/6825* | (2018.01) |

(52) U.S. Cl.
CPC ......... *C12Q 1/6897* (2013.01); *C12N 9/1247* (2013.01); *C12N 15/115* (2013.01); *C12Y 207/07006* (2013.01); *C12N 2310/16* (2013.01); *C12N 2330/30* (2013.01)

(58) Field of Classification Search
None
See application file for complete search history.

(56) References Cited

U.S. PATENT DOCUMENTS

| | | |
|---|---|---|
| 4,458,066 A | 7/1984 | Caruthers |
| 4,683,195 A | 7/1987 | Mullis |
| 4,683,202 A | 7/1987 | Mullis |
| 4,897,355 A | 1/1990 | Eppstein |
| 4,946,787 A | 8/1990 | Eppstein |
| 5,049,386 A | 9/1991 | Eppstein |
| 5,494,810 A | 2/1996 | Barany |
| 7,396,664 B2 | 7/2008 | Daly |
| 2017/0183664 A1 | 6/2017 | Lucks |
| 2021/0163947 A1 | 6/2021 | Silverman |
| 2021/0164059 A1 | 6/2021 | Jewett |
| 2021/0198678 A1 | 7/2021 | Glasscock |

FOREIGN PATENT DOCUMENTS

| | | |
|---|---|---|
| WO | 1991016024 A1 | 10/1991 |
| WO | 1991017424 A1 | 11/1991 |
| WO | 2018035158 A1 | 2/2018 |
| WO | 2018035159 A1 | 2/2018 |

OTHER PUBLICATIONS

Zhang, D. Y., et al. Engineering entropy-driven reactions and networks catalyzed by DNA. Science 318, 1121-1125 (2007).
Zhu, T., et al. Deciphering and engineering of the final step halogenase for improved chlortetracycline biosynthesis in industrial *Streptomyces aureofaciens*. Metabolic Engineering 19, 69-78 (2013).
Murray Elizabeth let al: "Application of the Invader RNA assay to the polarity of vertebrate mRNA decay.", Methods in Molecular Biology 2008, vol. 419, 2008, pp. 259-276.
Lin Jyun-Liang et al: "Enabling tools for high-throughput detection of metabolites: Metabolic engineering and directed evolution applications", Biotechnology Advances, Elsevier Publishing, Barking, GB, vol. 35, No. 8, (Jul. 16, 2017), pp. 950-970.
European Search Report. Corresponding to EP 19881824.7. Apr. 8, 2022.
Alam, K. K., et al. A Fluorescent Split Aptamer for Visualizing RNA-RNA Assembly In Vivo. ACS Synth. Biol. 6, 1710-1721 (2017).
Autour, A., et al. iSpinach: a fluorogenic RNA aptamer optimized for in vitro applications. Nucleic Acids Res. 44, 2491-2500 (2016).
Babendure, J. R., et al. Aptamers switch on fluorescence of triphenylmethane dyes. J. Am. Chem. Soc. 125, 14716-14717 (2003).
Beaucage, S. L., et al. "Deoxynucleoside phosphoramidites—a new class of key intermediates for deoxypolynucleotide synthesis." Tetrahedron letters 22.20 (1981): 1859-1862.
Bhadra, S. et al. Design and application of cotranscriptional non-enzymatic RNA circuits and signal transducers. Nucleic Acids Res. 42, e58-e58 (2014).

(Continued)

*Primary Examiner* — Suzanne M Noakes
*Assistant Examiner* — Jae W Lee
(74) *Attorney, Agent, or Firm* — Quarles & Brady LLP

(57) ABSTRACT

Disclosed are compositions, systems, kits, and methods for detecting an analyte or target molecule in a sample by regulated in vitro transcription. The compositions, systems, kits, and methods typically comprise and/or utilize one or more components selected from: (a) an RNA polymerase; (b) an allosteric transcription factor (ATT), wherein the ATT binds an analyte or target molecule as a ligand; (c) an engineered transcription template; and/or any combination thereof. The engineered transcription template typically comprises a promoter sequence for the RNA polymerase and an operator sequence for the ATT. The promoter sequence and operator sequence are operably linked to a sequence encoding an RNA, wherein the ATT modulates transcription of the encoded RNA when the ATT binds the analyte or target molecule as a ligand, wherein the transcribed RNA generates a detectable signal in conjunction with a reporter molecule.

32 Claims, 54 Drawing Sheets

Specification includes a Sequence Listing.

(56) References Cited

OTHER PUBLICATIONS

Brown et al., "[8] Chemical synthesis and cloning of a tyrosine tRNA gene." Methods in Enzymology. vol. 68. Academic Press, 1979. 109-151.
Busenlehner, L. S., et al. The SmtB/ArsR family of metalloregulatory transcriptional repressors: structural insights into prokaryotic metal resistance. FEMS Microbiol Rev 27, 131-143 (2003).
Chang, Y. M., et al. Structural analysis of the antibiotic-recognition mechanism of MarR proteins. Acta Crystallogr. D Biol. Crystallogr. 69, 1138-1149 (2013).
Dolgosheina, E. V. et al. RNA mango aptamer-fluorophore: a bright, high-affinity complex for RNA labeling and tracking. ACS Chem Biol 9, 2412-2420 (2014).
Fernandez-López, R., et al. Transcription factor-based biosensors enlightened by the analyte. 6, 1-21 (2015).
Filonov, G. S., et al. Broccoli: rapid selection of an RNA mimic of green fluorescent protein by fluorescence-based selection and directed evolution. J. Am. Chem. Soc. 136, 16299-16308 (2014).
Goodchild, "Conjugates of oligonucleotides and modified oligonucleotides: a review of their synthesis and properties." Bioconjugate Chemistry 1.3 (1990): 165-187.
Gootenberg, J. S. et al. Nucleic acid detection with CRISPR-Cas13a/C2c2. Science 356, 438-442 (2017).
Gossen, M., et al. "Transcriptional activation by tetracyclines in mammalian cells." Science 268.5218 (1995): 1766-1769.
Grate, D. et al. Laser-mediated, site-specific inactivation of RNA transcripts. Proc. Natl. Acad. Sci. U.S.A. 96, 6131-6136 (1999).
Grkovic, S., et al. QacR is a repressor protein that regulates expression of the *Staphylococcus aureus* multidrug efflux pump QacA. J. Biol. Chem. 273, 18665-18673 (1998).
Han, K. Y., et al. Understanding the Photophysics of the Spinach-DFHBI RNA Aptamer-Fluorogen Complex To Improve Live-Cell RNA Imaging. J. Am. Chem. Soc. 135, 19033-19038 (2013).
Heili, J. M. et al. Real-Time Visualization of in Vitro Transcription of a Fluorescent RNA Aptamer: An Experiment for the Upper-Division Undergraduate or First-Year Graduate Laboratory. Journal of Chemical Education 95, 1867-1871 (2018).
Hofer, K., et al. Universal aptamer-based real-time monitoring of enzymatic RNA synthesis. J. Am. Chem. Soc. 135, 13692-13694 (2013).
International Searching Authority. International Searching Report and Written Opinion for application PCT/US2019/060790. Mailed on Nov. 11, 2019. 9 pages.
Kasey, C. M., et al. Development of Transcription Factor-Based Designer Macrolide Biosensors for Metabolic Engineering and Synthetic Biology. ACS Synth. Biol. 7, 227-239 (2018).
Kellenberger, C. A., et al. RNA-Based Fluorescent Biosensors for Live Cell Imaging of Second Messengers Cyclic di-GMP and Cyclic AMP-GMP. J. Am. Chem. Soc. 135, 4906-4909 (2013).
Lloyd, J. et al. Dynamic Control of Aptamer-Ligand Activity Using Strand Displacement Reactions. ACS Synth. Biol. 7, 30-37 (2018).
Narang et al., "[6] Improved phosphotriester method for the synthesis of gene fragments." Methods in Enzymology. vol. 68. Academic Press, 1979. 90-98.
Noguchi, N., et al. 2000. Regulation of Transcription of the mph(A) Gene for Macrolide 2'-Phosphotransferase I in *Escherichia coli*: Characterization of the Regulatory Gene mphR(A). Am Soc Microbiol. 182(18). 5052-5058.
Nutiu, R. et al. "Structure-switching signaling aptamers." Journal of the American Chemical Society 125.16 (2003): 4771-4778.
Nutiu, R. et al. "Structure-switching signaling aptamers: transducing molecular recognition into fluorescence signaling." Chemistry—A European Journal 10.8 (2004): 1868-1876.
Owczarzy et al., "Predicting stability of DNA duplexes in solutions containing magnesium and monovalent cations." Biochemistry 47.19 (2008): 5336-5353.
Paige, J. S., et al. Fluorescence imaging of cellular metabolites with RNA. Science 335, 1194-1194 (2012).
Pardee, K. et al. Paper-Based Synthetic Gene Networks. Cell 1-22 (2014). doi:10.1016/j.cell.2014.10.004.
Pardee, K. et al. Rapid, Low-Cost Detection of Zika Virus Using Programmable Biomolecular Components. Cell 165, 1-25 (2016).
Reyes-Caballero, H. et al. The Metalloregulatory Zinc Site in *Streptococcus pneumoniae* AdcR, a Zinc-activated MarR Family Repressor. J. Mol. Biol. 403, 197-216 (2010).
Saenger, W., et al. The Tetracycline Repressor—A Paradigm for a Biological Switch. Angew Chem Int Ed Engl 39, 2042-2052 (2000).
Sajja, S., et al. Activation of Split RNA Aptamers: Experiments Demonstrating the Enzymatic Synthesis of Short RNAs and Their Assembly As Observed by Fluorescent Response. Journal of Chemical Education 95, 1861-1866 (2018).
Salehi, A. S. M. et al. Biosensing estrogenic endocrine disruptors in human blood and urine: A RAPID cell-free protein synthesis approach. Toxicol. Appl. Pharmacol. 345, 19-25 (2018).
Schaffter, S. W. et al. T7 RNA polymerase non-specifically transcribes and induces disassembly of DNA nanostructures. Nucleic Acids Res. 46, 5332-5343 (2018).
Soltani, M., et al. Reengineering cell-free protein synthesis as a biosensor: Biosensing with transcription, translation, and protein-folding. Biochemical Engineering Journal 138, 165-171 (2018).
Song, W. et al. Imaging RNA polymerase III transcription using a photostable RNA-fluorophore complex. Nat Chem Bio 13, 1187-1194 (2017).
Song, W., et al. Plug-and-play fluorophores extend the spectral properties of Spinach. J. Am. Chem. Soc. 136, 1198-1201 (2014).
Srinivas, N. et al. On the biophysics and kinetics of toehold-mediated DNA strand displacement. Nucleic Acids Res. 41, 10641-10658 (2013).
Strack, R. L., et al. A superfolding Spinach2 reveals the dynamic nature of trinucleotide repeat-containing RNA. Nature Methods 10, 1219-1224 (2013).
Takahashi, M. K. et al. Characterizing and prototyping genetic networks with cell-free transcription-translation reactions. Methods 86, 60-72 (2015).
Tatusova, T.A. et al. (1999), "Blast 2 sequences—a new tool for comparing protein and nucleotide sequences", FEMS Microbiol Lett. 174:247-250).
Voyvodic, P. L., et al. "Plug-and-play metabolic transducers expand the chemical detection space of cell-free biosensors." Nature communications 10.1 (2019): 1-8.
Wang, W. et al. Development of a Synthetic Oxytetracycline-Inducible Expression System for Streptomycetes Using de Novo Characterized Genetic Parts. ACS Synth. Biol. 5, 765-773 (2016).
Weber, W. et al. Macrolide-based transgene control in mammalian cells and mice. Nat. Biotechnol. 20, 901-907 (2002).
Wetmur, J. G. "DNA probes: applications of the principles of nucleic acid hybridization." Critical reviews in biochemistry and molecular biology 26.3-4 (1991): 227-259.
Yin, Y. W. et al. Structural basis for the transition from initiation to elongation transcription in T7 RNA polymerase. Science 298, 1387-1395 (2002).
Yoshida, M., et al. Ligand specificity of MobR, a transcriptional regulator for the 3-hydroxybenzoate hydroxylase gene of Comamonas testosteroni KH122-3s. Biochem. Biophys. Res. Commun. 362, 275-280 (2007).
Zhang, D. Y. et al. Dynamic DNA nanotechnology using strand-displacement reactions. Nature Chemistry 3, 103-113 (2011).

C

SBOL Visual 2.0.0 representation of DNA template

DFHBI-1T

B

C

A (SEQ ID NO:1)

5' TAATACGACTCACTATAGGGAGGTCCCTATCATCAGTGATAGAGACCCACATACTCTGATGATCCGAGACGGGTCCAGAT
ATTCGTATCTGTCGAGTAGAGAGTCAAGAGTCGGCAAGGTCATTCATGGCAAGAGATATTCGTATCTGTCGA
GTAGAGTGTGGCCTTGCCATGTGTATGGGTAGCATAACCCCTGGGCCCCTAAAGGGGTTGAGGGGTTTTTG 3'

3WJdB aptamer

T7 terminator

B

SBOL Visual 2.0.0 representation of DNA template

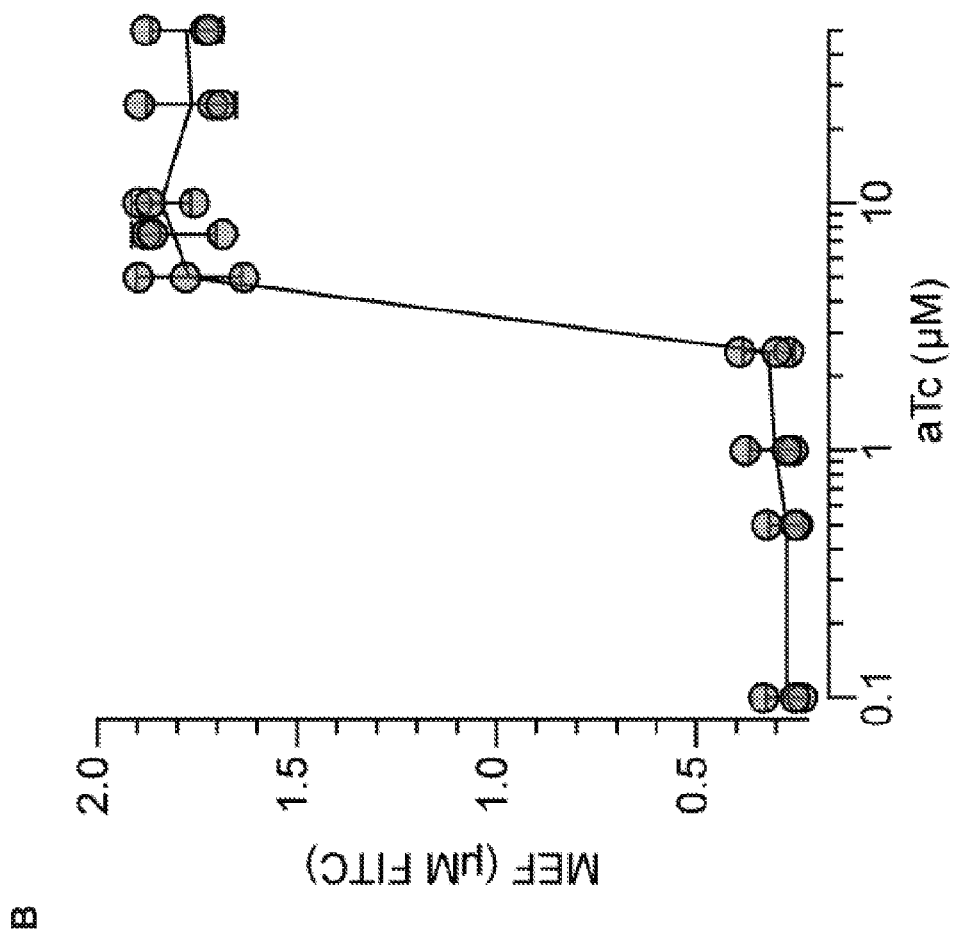

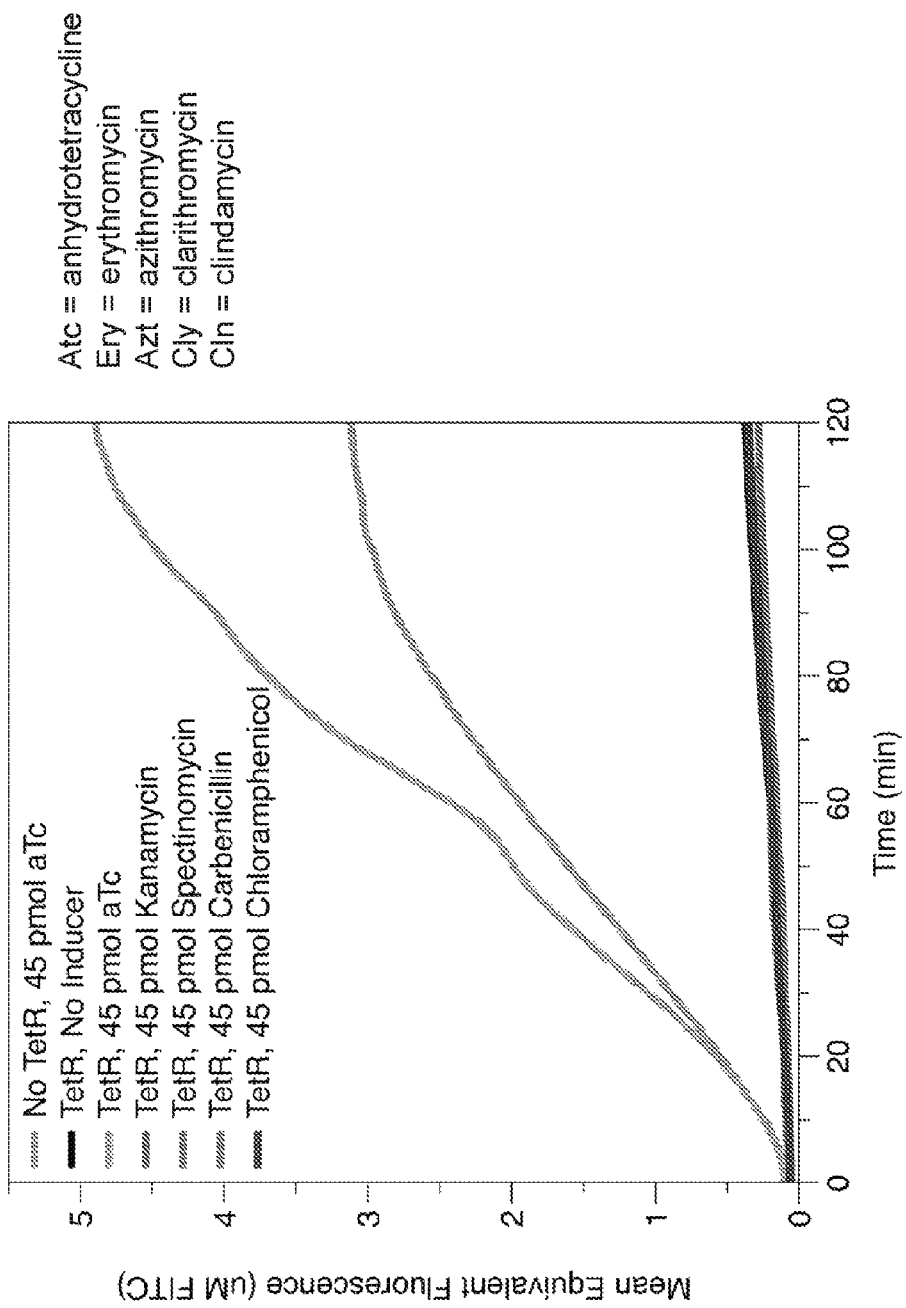

h g

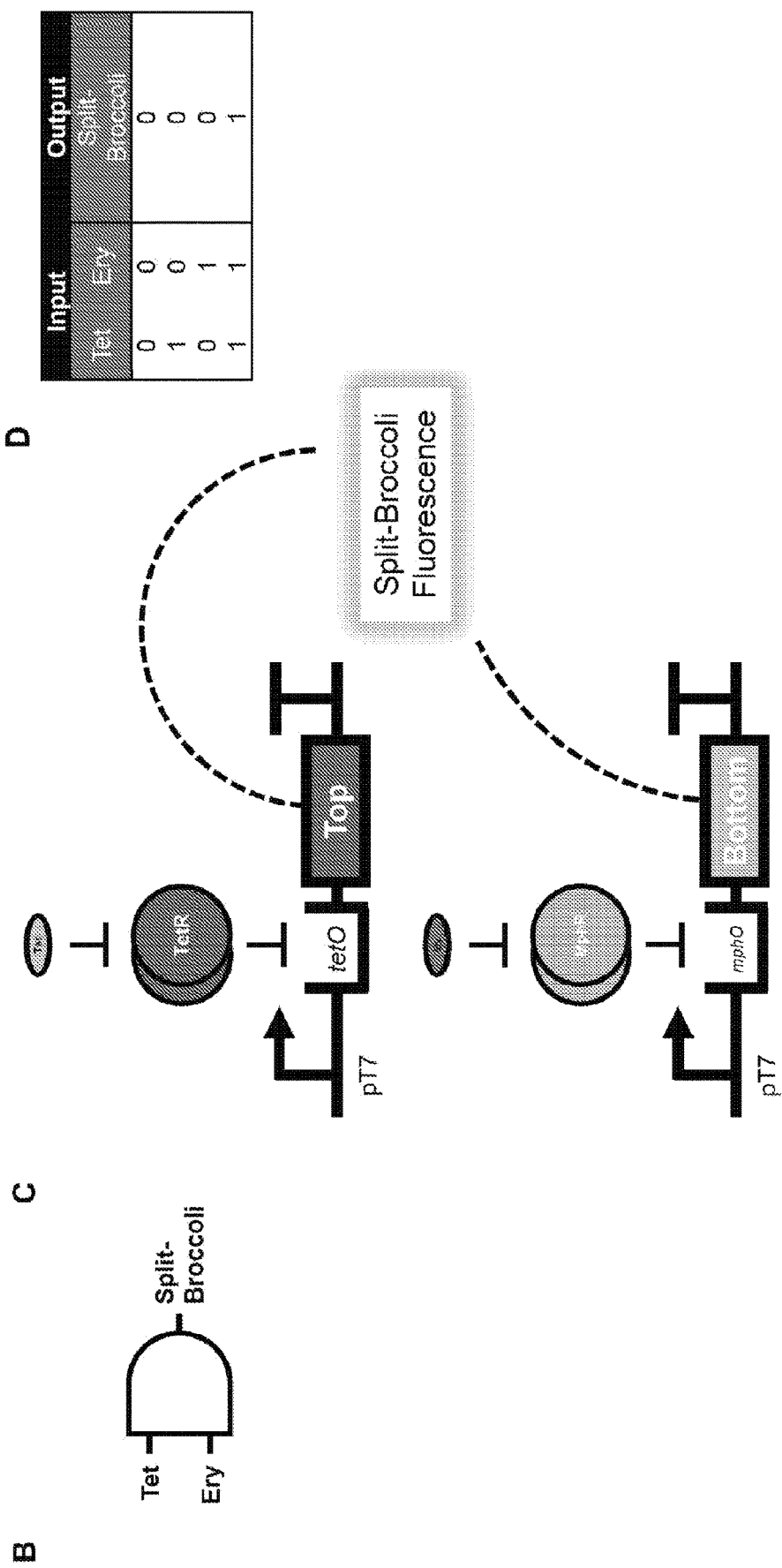

ANALYTES' DETECTION USING REGULATED IN VITRO TRANSCRIPTION

CROSS-REFERENCE TO RELATED PATENT APPLICATIONS

The present application represents the U.S. national stage entry of International Patent Application No. PCT/US2019/060790, filed on Nov. 11, 2019, and claims the benefit of priority to U.S. Provisional Application No. 62/758,242, filed on Nov. 9, 2018, the contents of both of which are incorporated herein by reference in their entirety.

REFERENCE TO AN ELECTRONIC SEQUENCE LISTING

The contents of the electronic sequence listing (Named: 702581.01952 ST25.txt; Size: 8,128 bytes; and Date of Creation: Aug. 23, 2024) is incorporated herein by reference in its entirety.

BACKGROUND

The present invention is related to compositions, systems, kits, and methods for detecting analytes and target molecules. The compositions, systems, kits, and methods utilize regulated in vitro transcription in order to detect an analyte or a target molecule in a sample.

Biology has evolved highly sophisticated, sensitive, and specific mechanisms to deal with environmental challenges to survival, growth, and reproduction. Many of these mechanisms rely on allosteric transcription factors to regulate gene expression in response to sensing the environmental challenge. When repurposed and engineered into biological systems, these allosteric transcription factors can serve as the foundation for powerful biosensors that enable on-site chemical analysis without requiring infrastructure or expertise. Whole-cell, reconstituted transcription-translation and cell-extract biosensors that utilize allosteric transcription factors are promising platforms for low-cost detection of analytes, ranging from molecular contaminants and toxins, to heavy metal ions. However, whole-cell biosensors are inherently limited by cellular physiology and raise concerns over the regulation, containment, and stability of genetically modified organisms. While reconstituted transcription-translation and cell-extract systems overcome these challenges, they can be costly or highly variable making them impractical. Here we present a novel biosensing platform that reduces the cost and variability of cell-free biosensors, while preserving the advantages that cell-free systems have over whole-cell biosensors. Our platform is able to sense a wide variety of analytes, is well-defined and highly reproducible, low-cost, and rapid when compared to existing whole-cell and cell-free biosensors.

SUMMARY

Disclosed herein are compositions, systems, kits, and methods that utilize regulated in vitro transcription in order to detect an analyte or a target molecule in a sample. The disclosed compositions, systems, kits, and methods typically comprise and/or utilize one or more components selected from: (a) an RNA polymerase; (b) an allosteric transcription factor (ATF), wherein the ATF binds an analyte or target molecule as a ligand; (c) an engineered transcription template; and/or any combination thereof. The engineered transcription template typically comprises a promoter sequence for the RNA polymerase and an operator sequence for the ATF. The promoter sequence and operator sequence are operably linked to a sequence encoding an RNA, wherein the ATF modulates transcription of the encoded RNA when the ATF binds the analyte or target molecule as a ligand. The RNA that is transcribed from the engineered transcription template generates a detectable signal in conjunction with a reporter molecule.

DETAILED DESCRIPTION

Figure 1:
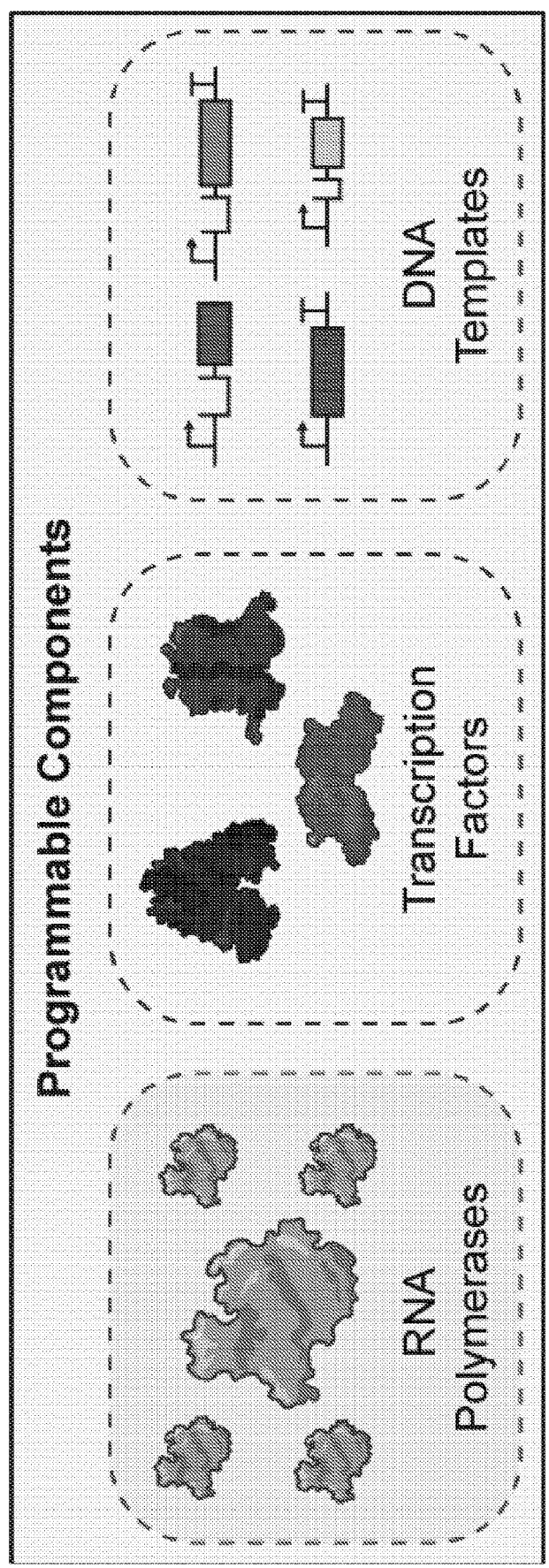
FIG. 1. Illustration of the components of a regulated in vitro transcription sensor which is modularly composed of three main elements: RNA Polymerase(s), Transcription Factor(s), and engineered Transcription Template(s).

The present invention is described herein using several definitions, as set forth below and throughout the application.

Unless otherwise specified or indicated by context, the terms "a", "an", and "the" mean "one or more." For example, "a composition," "a system," "a kit," "a method," "a protein," "a vector," "a domain," "a binding site," and "an RNA" should be interpreted to mean "one or more compositions," "one or more systems," "one or more kits," "one or more methods," "one or more proteins," "one or more vectors," "one or more domains," "one or more binding sites," and "one or more RNAs," respectively.

As used herein, "about," "approximately," "substantially," and "significantly" will be understood by persons of ordinary skill in the art and will vary to some extent on the context in which they are used. If there are uses of these terms which are not clear to persons of ordinary skill in the art given the context in which they are used, "about" and "approximately" will mean plus or minus≤10% of the particular term and "substantially" and "significantly" will mean plus or minus>10% of the particular term.

As used herein, the terms "include" and "including" have the same meaning as the terms "comprise" and "comprising" in that these latter terms are "open" transitional terms that do not limit claims only to the recited elements succeeding these transitional terms. The term "consisting of," while encompassed by the term "comprising," should be interpreted as a "closed" transitional term that limits claims only to the recited elements succeeding this transitional term. The term "consisting essentially of," while encompassed by the term "comprising," should be interpreted as a "partially closed" transitional term which permits additional elements succeeding this transitional term, but only if those additional elements do not materially affect the basic and novel characteristics of the claim.

As used herein, the terms "regulation" and "modulation" may be utilized interchangeably and may include "promotion" and "induction." For example, a transcription factor that regulates or modulates expression of a target gene may promote and/or induce expression of the target gene. In addition, the terms "regulation" and "modulation" may be utilized interchangeably and may include "inhibition" and "reduction." For example, a transcription factor that regulates or modulates expression of a target gene may inhibit and/or reduce expression of the target gene.

As used herein, the term "sample" may include "biological samples" and "non-biological samples." Biological samples may include samples obtained from a human or non-human subject. Biological samples may include but are not limited to, blood samples and blood product samples (e.g., serum or plasma), urine samples, saliva samples, fecal samples, perspiration samples, and tissue samples. Non-biological samples may include but are not limited to aqueous samples (e.g., watershed samples) and surface swab samples.

Polynucleotides and Uses Thereof

The terms "polynucleotide," "polynucleotide sequence," "nucleic acid" and "nucleic acid sequence" refer to a nucleotide, oligonucleotide, polynucleotide (which terms may be used interchangeably), or any fragment thereof. These phrases also refer to DNA or RNA of genomic, natural, or synthetic origin (which may be single-stranded or double-stranded and may represent the sense or the antisense strand).

The terms "nucleic acid" and "oligonucleotide," as used herein, may refer to polydeoxyribonucleotides (containing 2-deoxy-D-ribose), polyribonucleotides (containing D-ribose), and to any other type of polynucleotide that is an N glycoside of a purine or pyrimidine base. There is no intended distinction in length between the terms "nucleic acid", "oligonucleotide" and "polynucleotide", and these terms will be used interchangeably. These terms refer only to the primary structure of the molecule. Thus, these terms include double- and single-stranded DNA, as well as double- and single-stranded RNA. For use in the present methods, an oligonucleotide also can comprise nucleotide analogs in which the base, sugar, or phosphate backbone is modified as well as non-purine or non-pyrimidine nucleotide analogs.

Oligonucleotides can be prepared by any suitable method, including direct chemical synthesis by a method such as the phosphotriester method of Narang et al., 1979, *Meth. Enzymol.* 68:90-99; the phosphodiester method of Brown et al., 1979, *Meth. Enzymol.* 68:109-151; the diethylphosphoramidite method of Beaucage et al., 1981, *Tetrahedron Letters* 22:1859-1862; and the solid support method of U.S. Pat. No. 4,458,066, each incorporated herein by reference. A review of synthesis methods of conjugates of oligonucleotides and modified nucleotides is provided in Goodchild, 1990, *Bioconjugate Chemistry* 1(3): 165-187, incorporated herein by reference.

Regarding polynucleotide sequences, the terms "percent identity" and "% identity" refer to the percentage of residue matches between at least two polynucleotide sequences aligned using a standardized algorithm. Such an algorithm may insert, in a standardized and reproducible way, gaps in the sequences being compared in order to optimize alignment between two sequences, and therefore achieve a more meaningful comparison of the two sequences. Percent identity for a nucleic acid sequence may be determined as understood in the art. (See, e.g., U.S. Pat. No. 7,396,664, which is incorporated herein by reference in its entirety). A suite of commonly used and freely available sequence comparison algorithms is provided by the National Center for Biotechnology Information (NCBI) Basic Local Alignment Search Tool (BLAST), which is available from several sources, including the NCBI, Bethesda, Md., at its website. The BLAST software suite includes various sequence analysis programs including "blastn," that is used to align a known polynucleotide sequence with other polynucleotide sequences from a variety of databases. Also available is a tool called "BLAST 2 Sequences" that is used for direct pairwise comparison of two nucleotide sequences. "BLAST 2 Sequences" can be accessed and used interactively at the NCBI website. The "BLAST 2 Sequences" tool can be used for both blastn and blastp (discussed above).

Regarding polynucleotide sequences, percent identity may be measured over the length of an entire defined polynucleotide sequence, for example, as defined by a particular SEQ ID number, or may be measured over a shorter length, for example, over the length of a fragment taken from a larger, defined sequence, for instance, a fragment of at least 20, at least 30, at least 40, at least 50, at least 70, at least 100, or at least 200 contiguous nucleotides. Such lengths are exemplary only, and it is understood that any fragment length supported by the sequences shown herein, in the tables, figures, or Sequence Listing, may be used to describe a length over which percentage identity may be measured.

Regarding polynucleotide sequences, "variant," "mutant," or "derivative" may be defined as a nucleic acid sequence having at least 50% sequence identity to the particular nucleic acid sequence over a certain length of one of the nucleic acid sequences using blastn with the "BLAST 2 Sequences" tool available at the National Center for Biotechnology Information's website. (See Tatiana A. Tatusova, Thomas L. Madden (1999), "Blast 2 sequences—a new tool for comparing protein and nucleotide sequences", FEMS Microbiol Lett. 174:247-250). Such a pair of nucleic acids may show, for example, at least 60%, at least 70%, at least 80%, at least 85%, at least 90%, at least 91%, at least 92%, at least 93%, at least 94%, at least 95%, at least 96%, at least 97%, at least 98%, or at least 99% or greater sequence identity over a certain defined length.

Nucleic acid sequences that do not show a high degree of identity may nevertheless encode similar amino acid sequences due to the degeneracy of the genetic code where multiple codons may encode for a single amino acid. It is understood that changes in a nucleic acid sequence can be made using this degeneracy to produce multiple nucleic acid sequences that all encode substantially the same protein. For example, polynucleotide sequences as contemplated herein may encode a protein and may be codon-optimized for expression in a particular host. In the art, codon usage frequency tables have been prepared for a number of host organisms including humans, mouse, rat, pig, E. coli, plants, and other host cells.

A "recombinant nucleic acid" is a sequence that is not naturally occurring or has a sequence that is made by an artificial combination of two or more otherwise separated segments of sequence. This artificial combination is often accomplished by chemical synthesis or, more commonly, by the artificial manipulation of isolated segments of nucleic acids, e.g., by genetic engineering techniques known in the art. The term recombinant includes nucleic acids that have been altered solely by addition, substitution, or deletion of a portion of the nucleic acid. Frequently, a recombinant nucleic acid may include a nucleic acid sequence operably linked to a promoter sequence. Such a recombinant nucleic acid may be part of a vector that is used, for example, to transform a cell.

The nucleic acids disclosed herein may be "substantially isolated or purified." The term "substantially isolated or purified" refers to a nucleic acid that is removed from its natural environment, and is at least 60% free, preferably at least 75% free, and more preferably at least 90% free, even more preferably at least 95% free from other components with which it is naturally associated.

The term "amplification reaction" refers to any chemical reaction, including an enzymatic reaction, which results in increased copies of a template nucleic acid sequence or results in transcription of a template nucleic acid. Amplification reactions include reverse transcription, the polymerase chain reaction (PCR), including Real Time PCR (see U.S. Pat. Nos. 4,683,195 and 4,683,202; PCR Protocols: A Guide to Methods and Applications (Innis et al., eds, 1990)), and the ligase chain reaction (LCR) (see Barany et al., U.S. Pat. No. 5,494,810). Exemplary "amplification reactions conditions" or "amplification conditions" typically comprise either two or three step cycles. Two-step cycles have a high temperature denaturation step followed by a hybridization/elongation (or ligation) step. Three step cycles comprise a denaturation step followed by a hybridization step followed by a separate elongation step.

The terms "target," "target sequence," "target region," and "target nucleic acid," as used herein, are synonymous and may refer to a region or sequence of a nucleic acid which is to be hybridized and/or bound by another nucleic acid (e.g., a target sequence that is bound by a STAR RNA and/or a target sequence that is bound by a trigger RNA for a Toehold switch).

The term "hybridization," as used herein, refers to the formation of a duplex structure by two single-stranded nucleic acids due to complementary base pairing. Hybridization can occur between fully complementary nucleic acid strands or between "substantially complementary" nucleic acid strands that contain minor regions of mismatch. Conditions under which hybridization of fully complementary nucleic acid strands is strongly preferred are referred to as "stringent hybridization conditions" or "sequence-specific hybridization conditions". Stable duplexes of substantially complementary sequences can be achieved under less stringent hybridization conditions; the degree of mismatch tolerated can be controlled by suitable adjustment of the hybridization conditions. Those skilled in the art of nucleic acid technology can determine duplex stability empirically considering a number of variables including, for example, the length and base pair composition of the oligonucleotides, ionic strength, and incidence of mismatched base pairs, following the guidance provided by the art (see, e.g., Sambrook et al., 1989, Molecular Cloning—A Laboratory Manual, Cold Spring Harbor Laboratory, Cold Spring Harbor, New York; Wetmur, 1991, Critical Review in Biochem. and Mol. Biol. 26(3/4):227-259; and Owczarzy et al., 2008, *Biochemistry*, 47: 5336-5353, which are incorporated herein by reference).

The term "primer," as used herein, refers to an oligonucleotide capable of acting as a point of initiation of DNA synthesis under suitable conditions. Such conditions include those in which synthesis of a primer extension product complementary to a nucleic acid strand is induced in the presence of four different nucleoside triphosphates and an agent for extension (for example, a DNA polymerase or reverse transcriptase) in an appropriate buffer and at a suitable temperature.

A primer is preferably a single-stranded DNA. The appropriate length of a primer depends on the intended use of the primer but typically ranges from about 6 to about 225 nucleotides, including intermediate ranges, such as from 15 to 35 nucleotides, from 18 to 75 nucleotides and from 25 to 150 nucleotides. Short primer molecules generally require cooler temperatures to form sufficiently stable hybrid complexes with the template. A primer need not reflect the exact sequence of the template nucleic acid, but must be sufficiently complementary to hybridize with the template. The design of suitable primers for the amplification of a given target sequence is well known in the art and described in the literature cited herein.

Primers can incorporate additional features which allow for the detection or immobilization of the primer but do not alter the basic property of the primer, that of acting as a point of initiation of DNA synthesis. For example, primers may contain an additional nucleic acid sequence at the 5' end which does not hybridize to the target nucleic acid, but which facilitates cloning or detection of the amplified product, or which enables transcription of RNA (for example, by inclusion of a promoter) or translation of protein (for example, by inclusion of a 5'-UTR, such as an Internal Ribosome Entry Site (IRES) or a 3'-UTR element, such as a poly(A)$_n$ sequence, where n is in the range from about 20 to about 200). The region of the primer that is sufficiently complementary to the template to hybridize is referred to herein as the hybridizing region.

As used herein, a primer is "specific," for a target sequence if, when used in an amplification reaction under sufficiently stringent conditions, the primer hybridizes primarily to the target nucleic acid. Typically, a primer is specific for a target sequence if the primer-target duplex stability is greater than the stability of a duplex formed between the primer and any other sequence found in the sample. One of skill in the art will recognize that various factors, such as salt conditions as well as base composition of the primer and the location of the mismatches, will affect the specificity of the primer, and that routine experimental confirmation of the primer specificity will be needed in many cases. Hybridization conditions can be chosen under which the primer can form stable duplexes only with a target sequence. Thus, the use of target-specific primers under suitably stringent amplification conditions enables the selective amplification of those target sequences that contain the target primer binding sites.

As used herein, a "polymerase" refers to an enzyme that catalyzes the polymerization of nucleotides. "DNA polymerase" catalyzes the polymerization of deoxyribonucleotides. Known DNA polymerases include, for example, *Pyrococcus furiosus* (Pfu) DNA polymerase, *E. coli* DNA polymerase I, T7 DNA polymerase and *Thermus aquaticus* (Taq) DNA polymerase, among others. "RNA polymerase" catalyzes the polymerization of ribonucleotides. The foregoing examples of DNA polymerases are also known as DNA-dependent DNA polymerases. RNA-dependent DNA polymerases also fall within the scope of DNA polymerases. Reverse transcriptase, which includes viral polymerases encoded by retroviruses, is an example of an RNA-dependent DNA polymerase. Known examples of RNA polymerase ("RNAP") include, for example, RNA polymerases of bacteriophages (e.g. T3 RNA polymerase, T7 RNA polymerase, SP6 RNA polymerase, Syn5 RNA polymerase), and *E. coli* RNA polymerase, among others. The foregoing examples of RNA polymerases are also known as DNA-dependent RNA polymerase. The polymerase activity of any of the above enzymes can be determined by means well known in the art.

Also contemplated for us in the disclosed compositions, systems, kits, and methods are engineered RNA polymerase. For example, an engineered polymerase may be a non-naturally occurring RNA polymerase whose amino acid sequence has been engineered to include one or more of an insertion, a deletion, or a substitution relative to the amino acid sequence of a naturally occurring or wild-type RNA polymerase.

The term "promoter" refers to a cis-acting DNA sequence that directs RNA polymerase and other trans-acting transcription factors to initiate RNA transcription from the DNA template that includes the cis-acting DNA sequence.

As used herein, "an engineered transcription template" or "an engineered expression template" refers to a non-naturally occurring nucleic acid that serves as substrate for transcribing at least one RNA. As used herein, "expression template" and "transcription template" have the same meaning and are used interchangeably. Engineered include nucleic acids composed of DNA or RNA. Suitable sources of DNA for use in a nucleic acid for an expression template include genomic DNA, cDNA and RNA that can be converted into cDNA. Genomic DNA, cDNA and RNA can be from any biological source, such as a tissue sample, a biopsy, a swab, sputum, a blood sample, a fecal sample, a urine sample, a scraping, among others. The genomic DNA, cDNA and RNA can be from host cell or virus origins and from any species, including extant and extinct organisms.

"Transformation" or "transfection" describes a process by which exogenous nucleic acid (e.g., DNA or RNA) is introduced into a recipient cell. Transformation or transfection may occur under natural or artificial conditions according to various methods well known in the art, and may rely on any known method for the insertion of foreign nucleic acid sequences into a prokaryotic or eukaryotic host cell. The method for transformation or transfection is selected based on the type of host cell being transformed and may include, but is not limited to, bacteriophage or viral infection or non-viral delivery. Methods of non-viral delivery of nucleic acids include lipofection, nucleofection, microinjection, electroporation, heat shock, particle bombardment, biolistics, virosomes, liposomes, immunoliposomes, polycation or lipid:nucleic acid conjugates, naked DNA, artificial virions, and agent-enhanced uptake of DNA. Lipofection is described in e.g., U.S. Pat. Nos. 5,049,386, 4,946,787; and 4,897,355) and lipofection reagents are sold commercially (e.g., Transfectam™ and Lipofectin™). Cationic and neutral lipids that are suitable for efficient receptor-recognition lipofection of polynucleotides include those of Felgner, WO 91/17424; WO 91/16024. Delivery can be to cells (e.g. in vitro or ex vivo administration) or target tissues (e.g. in vivo administration). The term "transformed cells" or "transfected cells" includes stably transformed or transfected cells in which the inserted DNA is capable of replication either as an autonomously replicating plasmid or as part of the host chromosome, as well as transiently transformed or transfected cells which express the inserted DNA or RNA for limited periods of time.

The polynucleotide sequences contemplated herein may be present in expression vectors. For example, the vectors may comprise a polynucleotide encoding an ORF of a protein operably linked to a promoter. "Operably linked" refers to the situation in which a first nucleic acid sequence is placed in a functional relationship with a second nucleic acid sequence. For instance, a promoter is operably linked to a coding sequence if the promoter affects the transcription or expression of the coding sequence. Operably linked DNA sequences may be in close proximity or contiguous and, where necessary to join two protein coding regions, in the same reading frame. Vectors contemplated herein may comprise a heterologous promoter operably linked to a polynucleotide that encodes a protein. A "heterologous promoter" refers to a promoter that is not the native or endogenous promoter for the protein or RNA that is being expressed.

As used herein, "expression" refers to the process by which a polynucleotide is transcribed from a DNA template (such as into mRNA or another RNA transcript) and/or the process by which a transcribed mRNA is subsequently translated into peptides, polypeptides, or proteins. Transcripts and encoded polypeptides may be collectively referred to as "gene product."

The term "vector" refers to some means by which nucleic acid (e.g., DNA) can be introduced into a host organism or host tissue. There are various types of vectors including plasmid vector, bacteriophage vectors, cosmid vectors, bacterial vectors, and viral vectors. As used herein, a "vector" may refer to a recombinant nucleic acid that has been engineered to express a heterologous polypeptide (e.g., the fusion proteins disclosed herein). The recombinant nucleic acid typically includes cis-acting elements for expression of the heterologous polypeptide.

In the methods contemplated herein, a host cell may be transiently or non-transiently transfected (i.e., stably transfected) with one or more vectors described herein. A cell transfected with one or more vectors described herein may be used to establish a new cell line comprising one or more vector-derived sequences. In the methods contemplated herein, a cell may be transiently transfected with the components of a system as described herein (such as by transient transfection of one or more vectors), and modified through the activity of a complex, in order to establish a new cell line comprising cells containing the modification but lacking any other exogenous sequence.

Peptides, Polypeptides, and Proteins

As used herein, the terms "protein" or "polypeptide" or "peptide" may be used interchangeable to refer to a polymer of amino acids. Typically, a "polypeptide" or "protein" is defined as a longer polymer of amino acids, of a length typically of greater than 50, 60, 70, 80, 90, or 100 amino acids. A "peptide" is defined as a short polymer of amino acids, of a length typically of 50, 40, 30, 20 or less amino acids.

A "protein" as contemplated herein typically comprises a polymer of naturally or non-naturally occurring amino acids (e.g., alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine). The proteins contemplated herein may be further modified in vitro or in vivo to include non-amino acid moieties. These modifications may include but are not limited to acylation (e.g., O-acylation (esters), N-acylation (amides), S-acylation (thioesters)), acetylation (e.g., the addition of an acetyl group, either at the N-terminus of the protein or at lysine residues), formylation lipoylation (e.g., attachment of a lipoate, a C8 functional group), myristoylation (e.g., attachment of myristate, a C14 saturated acid), palmitoylation (e.g., attachment of palmitate, a C16 saturated acid), alkylation (e.g., the addition of an alkyl group, such as an methyl at a lysine or arginine residue), isoprenylation or prenylation (e.g., the addition of an isoprenoid group such as farnesol or geranylgeraniol), amidation at C-terminus, glycosylation (e.g., the addition of a glycosyl group to either asparagine, hydroxylysine, serine, or threonine, resulting in a glycoprotein). Distinct from glycation, which is regarded as a non-enzymatic attachment of sugars, polysialylation (e.g., the addition of polysialic acid), glypiation (e.g., glycosylphosphatidylinositol (GPI) anchor formation), hydroxylation, iodination (e.g., of thyroid hormones), and phosphorylation (e.g., the addition of a phosphate group, usually to serine, tyrosine, threonine or histidine).

The proteins disclosed herein may include "wild type" proteins and variants, mutants, and derivatives thereof. As used herein the term "wild type" is a term of the art understood by skilled persons and means the typical form of an organism, strain, gene or characteristic as it occurs in nature as distinguished from mutant or variant forms. As used herein, a "variant, "mutant," or "derivative" refers to a protein molecule having an amino acid sequence that differs from a reference protein or polypeptide molecule. A variant or mutant may have one or more insertions, deletions, or substitutions of an amino acid residue relative to a reference molecule. A variant or mutant may include a fragment of a reference molecule. For example, a mutant or variant molecule may have one or more insertions, deletions, or substitution of at least one amino acid residue relative to a reference polypeptide.

Regarding proteins, a "deletion" refers to a change in the amino acid sequence that results in the absence of one or more amino acid residues. A deletion may remove at least 1, 2, 3, 4, 5, 10, 20, 50, 100, 200, or more amino acids residues. A deletion may include an internal deletion and/or a terminal deletion (e.g., an N-terminal truncation, a C-terminal truncation or both of a reference polypeptide). A "variant," "mutant," or "derivative" of a reference polypeptide sequence may include a deletion relative to the reference polypeptide sequence.

Regarding proteins, "fragment" is a portion of an amino acid sequence which is identical in sequence to but shorter in length than a reference sequence. A fragment may comprise up to the entire length of the reference sequence, minus at least one amino acid residue. For example, a fragment may comprise from 5 to 1000 contiguous amino acid residues of a reference polypeptide, respectively. In some embodiments, a fragment may comprise at least 5, 10, 15, 20, 25, 30, 40, 50, 60, 70, 80, 90, 100, 150, 250, or 500 contiguous amino acid residues of a reference polypeptide. Fragments may be preferentially selected from certain regions of a molecule. The term "at least a fragment" encompasses the full-length polypeptide. A fragment may include an N-terminal truncation, a C-terminal truncation, or both truncations relative to the full-length protein. A "variant," "mutant," or "derivative" of a reference polypeptide sequence may include a fragment of the reference polypeptide sequence.

Regarding proteins, the words "insertion" and "addition" refer to changes in an amino acid sequence resulting in the addition of one or more amino acid residues. An insertion or addition may refer to 1, 2, 3, 4, 5, 10, 20, 30, 40, 50, 60, 70, 80, 90, 100, 150, 200, or more amino acid residues. A "variant," "mutant," or "derivative" of a reference polypeptide sequence may include an insertion or addition relative to the reference polypeptide sequence. A variant of a protein may have N-terminal insertions, C-terminal insertions, internal insertions, or any combination of N-terminal insertions, C-terminal insertions, and internal insertions.

Regarding proteins, the phrases "percent identity" and "% identity," refer to the percentage of residue matches between at least two amino acid sequences aligned using a standardized algorithm. Methods of amino acid sequence alignment are well-known. Some alignment methods take into account conservative amino acid substitutions. Such conservative substitutions, explained in more detail below, generally preserve the charge and hydrophobicity at the site of substitution, thus preserving the structure (and therefore function) of the polypeptide. Percent identity for amino acid sequences may be determined as understood in the art. (See, e.g., U.S. Pat. No. 7,396,664, which is incorporated herein by reference in its entirety). A suite of commonly used and freely available sequence comparison algorithms is provided by the National Center for Biotechnology Information (NCBI) Basic Local Alignment Search Tool (BLAST), which is available from several sources, including the NCBI, Bethesda, Md., at its website. The BLAST software suite includes various sequence analysis programs including "blastp," that is used to align a known amino acid sequence with other amino acids sequences from a variety of databases.

Regarding proteins, percent identity may be measured over the length of an entire defined polypeptide sequence, for example, as defined by a particular SEQ ID number, or may be measured over a shorter length, for example, over the length of a fragment taken from a larger, defined polypeptide sequence, for instance, a fragment of at least 15, at least 20, at least 30, at least 40, at least 50, at least 70 or at least 150 contiguous residues. Such lengths are exemplary only, and it is understood that any fragment length supported by the sequences shown herein, in the tables, figures or Sequence Listing, may be used to describe a length over which percentage identity may be measured.

Regarding proteins, the amino acid sequences of variants, mutants, or derivatives as contemplated herein may include conservative amino acid substitutions relative to a reference amino acid sequence. For example, a variant, mutant, or derivative protein may include conservative amino acid substitutions relative to a reference molecule. "Conservative amino acid substitutions" are those substitutions that are a substitution of an amino acid for a different amino acid where the substitution is predicted to interfere least with the properties of the reference polypeptide. In other words, conservative amino acid substitutions substantially conserve the structure and the function of the reference polypeptide. The following table provides a list of exemplary conservative amino acid substitutions which are contemplated herein:

| Original Residue | Conservative Substitution |
| --- | --- |
| Ala | Gly, Ser |
| Arg | His, Lys |
| Asn | Asp, Gln, His |
| Asp | Asn, Glu |
| Cys | Ala, Ser |
| Gln | Asn, Glu, His |
| Glu | Asp, Gln, His |
| Gly | Ala |
| His | Asn, Arg, Gln, Glu |
| Ile | Leu, Val |
| Leu | Ile, Val |
| Lys | Arg, Gln, Glu |
| Met | Leu, Ile |
| Phe | His, Met, Leu, Trp, Tyr |
| Ser | Cys, Thr |
| Thr | Ser, Val |
| Trp | Phe, Tyr |
| Tyr | His, Phe, Trp |
| Val | Ile, Leu, Thr |

Conservative amino acid substitutions generally maintain (a) the structure of the polypeptide backbone in the area of the substitution, for example, as a beta sheet or alpha helical conformation, (b) the charge or hydrophobicity of the molecule at the site of the substitution, and/or (c) the bulk of the side chain. Non-conservative amino acids typically disrupt (a) the structure of the polypeptide backbone in the area of the substitution, for example, as a beta sheet or alpha helical conformation, (b) the charge or hydrophobicity of the molecule at the site of the substitution, and/or (c) the bulk of the side chain.

The disclosed proteins, mutants, variants, or described herein may have one or more functional or biological activities exhibited by a reference polypeptide (e.g., one or more functional or biological activities exhibited by wild-type protein).

In some embodiments of the disclosed compositions, systems, kits, and methods, the components may be substantially isolated or purified. The term "substantially isolated or purified" refers to components that are removed from their natural environment, and are at least 60% free, preferably at least 75% free, and more preferably at least 90% free, even more preferably at least 95% free from other components with which they are naturally associated.

Detection of Analytes and Target Molecules Using Regulated In Vitro Transcription Disclosed are compositions, systems, kits, and methods that relate to detection of analytes and target molecules using regulated in vitro transcription. The disclosed compositions, systems, kits, and methods include and utilize components as described herein.

The disclosed compositions, systems, kits, and methods may be utilized to detect an analyte or a target molecule in a sample. In some embodiments, the disclosed compositions, systems, kits, and methods comprise or utilize one or more components selected from: (a) an RNA polymerase; (b) an allosteric transcription factor (ATF), wherein the analyte or target molecule is a ligand to which the ATF binds; (c) an engineered transcription template; or a combination thereof. The transcription template typically comprises a promoter sequence for the RNA polymerase and an operator sequence for the ATF. The promoter sequence and operator sequence are operably linked to a sequence encoding an RNA, wherein the ATF modulates transcription of the encoded RNA when the ATF binds the analyte or target molecule as a ligand. The RNA that is transcribed from the transcription template typically binds to a reporter molecule, and the RNA binding to the reporter molecule results in a detectable signal being generated, thereby indicating that the analyte or target molecule is present.

In some embodiments of the disclosed compositions, systems, or kits, the transcribed RNA binds to the reporter molecule which RNA binding generates a detectable signal. Suitable reporter molecules may include fluorescence-activated dyes (e.g., dyes activated by an RNA aptamer as described) or fluorescently labeled double-stranded nucleotide molecules (e.g., fluorescently double-stranded DNA molecules as described herein).

In other embodiments of the disclosed compositions, systems, or kits, the compositions, systems, or kits further comprise a second engineered transcription template, in which the second engineered transcription template comprises a promoter sequence for the RNA polymerase operably linked to a sequence encoding a second RNA. In these embodiments, the second RNA binds to the reporter molecule which second RNA binding generates a detectable signal (e.g., where the reporter molecule is fluorescence-activated dye as described or a fluorescently labeled double-stranded nucleotide molecule as described herein), and the RNA transcribed from the first engineered transcription template, namely the first RNA, interacts with the second RNA and interferes with the detectable signal generated by the second RNA binding to the reporter molecule (e.g., as a kleptamer).

Suitable RNA polymerases for inclusion or use in the disclosed compositions, systems, kits, and methods may include, but are not limited to, RNA polymerases derived from bacteriophages. Suitable RNA polymerases may include but are not limited to T7 RNA polymerase, T3 RNA polymerase, SP6 RNA polymerase, and Syn5 RNA polymerase. Suitable RNA polymerases may include engineered RNA polymerases as contemplated herein.

In the disclosed compositions, systems, kits, and methods, the allosteric transcription factor (ATF) modulates transcription from the engineered transcription template. In some embodiments, the ATF modulates transcription from the engineered transcription template when the ATF binds the operator sequence. In some embodiments, the ATF represses transcription from the engineered transcription template when the ATF binds the operator sequence. In other embodiments, the ATF activates, derepresses, and/or augments transcription from the engineered transcription template when the ATF binds the operator sequence.

In the disclosed compositions, systems, kits, and methods, the allosteric transcription factor (ATF) binds the analyte or target molecule as a ligand. In some embodiments, in the absence of the analyte or target molecule as a ligand the ATF binds to the operator sequence, and/or in the presence of the analyte or target molecule as a ligand the ATF does not bind to the operator sequence or binds to the operator sequence at a lower affinity than in the absence of the analyte or target molecule as a ligand. In other embodiments, in the presence of the analyte or target molecule as a ligand the ATF binds to the operator sequence, and/or in the absence of the analyte or target molecule as a ligand the ATF does not bind to the operator sequence or binds to the operator sequence at a lower affinity than in the presence of the analyte or target molecule as a ligand.

Allosteric transcription factors (ATFs) are known in the art. Suitable ATFs for the disclosed compositions, systems, kits, and methods may include, but are not limited to prokaryotic ATFs. Suitable ATFs may include but are not limited to TetR, MphR, QacR, OtrR, CtcS, SAR2349, MobR, and SmtB. The TetR family of ATFs include TetR, MphR, and QacR. The MarR family of ATFs include OtrR, CtcS, SAR2349, and MobR. Suitable ATF may also include the ArsR/SmtB family of ATFs.

Suitable ATFs may include engineered ATFs. For example an engineered ATF is a non-naturally occurring ATF having an amino acid sequence which has been engineered to include one or more of an insertion, a deletion, or a substitution relative to the amino acid sequence of a naturally occurring or wild-type ATF.

In some embodiments of the disclosed compositions, systems, kits, and methods, the analyte or target molecule that is a ligand for the ATF is a member of the tetracycline-family of antibiotics. Suitable analytes/target molecules as ligands for the ATF may include, but are not limited to tetracycline, anhydrotetracyline, oxytetracycline, chlortetracycline, and doxycycline.

In some embodiments of the disclosed systems and methods, the target molecule that is the ligand for the ATF is a member of the macrolide-family of antibiotics. Suitable target molecules/ligands for the ATF may include, but are not limited to erythromycin, azithromycin, and clarithromycin.

In some embodiments of the disclosed compositions, systems, kits, and methods, the analyte or target molecule that is a ligand for the ATF is a quaternary amine or salts thereof. Suitable quaternary amines may include but are not limited to alkyldimethylbenzylammonium salts.

In some embodiments of the disclosed compositions, systems, kits, and methods, the analyte that is a ligand for the ATF is a metal or a cation thereof. Suitable metals or cations thereof may include but are not limited to heavy metals and cations thereof. Suitable metals or cations thereof may include but are not limited to Zn, Pb, Cu, Cd, Ni, As, Mn (or $Zn^{2+}$, $Pb^{2+}$, $Cu^+$, $Cu^{2+}$, $Cd^{2+}$, $Ni^{2+}$, $As^{3+}$, $As^{5+}$, and $Mn^{2+}$).

In some embodiments of the disclosed compositions, systems, kits, and methods, the analyte that is a ligand for the ATF is selected from salicylate, 3-hydroxy benzoic acid, narigenin, uric acid.

In the disclosed compositions, systems, kits, and methods, the RNA that is transcribed from the engineered transcription template typically binds to a reporter molecule, and the RNA binding to the reporter molecule results in a detectable signal being generated. Suitable transcribed RNAs for the disclosed compositions, systems, kits, and methods may include but are not limited to fluorescence-activating aptamers. Suitable transcribed RNAs may include, but are not limited to, Malachite Green aptamer, Mango aptamer, and the Spinach/Broccoli family of aptamers. Suitable transcribed RNAs may include, but are not limited to a three-way junction dimeric Broccoli (3WJdB) aptamer.

In some embodiments of the disclosed compositions, systems, kits, and methods, the compositions, systems, kits, and methods include or utilize (d) a dye, wherein the transcribed RNA is an aptamer that binds and activates the fluorescence of the dye (e.g., by forming a fluorescent complex) to generate the detectable signal. Suitable dyes that are activated by the transcribed aptamer may include but are not limited to 4-hydroxybenzlidene imidazolinone (HBI)-derivative dye, such as (5Z)-5-[(3,5-Difluoro-4-hydroxyphenyl)methylene]-3,5-dihydro-2,3-dimethyl-4H-Imidazol-4-one, (Z)-4-(3,5-Difluoro-4-hydroxybenzylidene)-1, 2-dimethyl-1H-imidazol-5 (4H)-one (DFHBI); (5Z)-5-[(3,5-Difluoro-4-hydroxyphenyl)methylene]-3,5-dihydro-2-methyl-3-(2,2,2-trifluoroethyl)-4H-imidazol-4-one (DFHBI-1T); 3,5-difluoro-4-hydroxybenzylidene imidazolinone-2-oxime (DFHO), thiazole orange dyes (e.g., TO1-Biotin), and Malachite Green.

In the disclosed compositions, systems, kits, and methods, the RNA that is transcribed from the engineered transcription template typically binds to a reporter molecule, and the RNA binding to the reporter molecule results in a detectable signal being generated. In some embodiments of the disclosed compositions, systems, kits, and methods, the reporter molecule is a fluorescently labeled double-stranded nucleic acid (e.g., which functions as an output gate) comprising a fluorophore and a quencher that quenches the fluorophore in the fluorescently labeled double-stranded nucleic acid. In these embodiments, the RNA that is transcribed from the engineered transcription template displaces one of the strands of the fluorescently labeled double-stranded nucleic acid which results in dequenching of the fluorophore to generate the detectable signal.

Suitable reporter molecules may include but are not limited to fluorescently labeled double-stranded DNA molecules (e.g., which function as an output gate) comprising a top strand having a fluorophore conjugated at its 3'-end and a bottom strand having a quencher conjugated at its 5' end that quenches the fluorophore in the fluorescently labeled double-stranded DNA molecule. In these embodiments, the RNA that is transcribed from the engineered transcription template comprises a sequence that is complementary to the full length of the top strand and the transcribed RNA displaces the bottom strand which results in dequenching of the fluorophore to generate the detectable signal. Typically these reporter molecules are configured such that, the top strand is longer than the bottom strand (e.g., by about 1, 2, 3, 4, 5, 6, 7, 8, 9, 10, 11, 12, 13, 14, 15 nucleotides or more). In this configuration, displacement of the bottom strand by the transcribed RNA is thermodynamically favored because the transcribed RNA comprises a sequence that is complementary to the full length of the top strand, which permits additional base-pairing between the transcribed RNA and the top strand that is not presented between the top strand and the bottom strand. Optionally, the disclosed systems and methods further may comprise a non-labeled double-stranded DNA molecule (e.g., which functions as a threshold gate) comprising a top strand that comprises a nucleotide sequence that is identical to the nucleotide sequence of the top strand of the labeled double-stranded DNA molecule.

Typically, the top strand of the non-labeled double-stranded DNA molecule is longer than the bottom strand of the non-labeled double-stranded DNA molecule (e.g., by about 1, 2, 3, 4, 5, 6, 7, 8, 9, 10, 11, 12, 13, 14, 15 nucleotides or more). Optionally, the bottom strand of the non-labeled double-stranded DNA molecule is shorter in length than the length of the bottom strand of the fluorescently labeled double-stranded DNA molecule (e.g., by about 1, 2, 3, 4, 5, 6, 7, 8, 9, 10, 11, 12, 13, 14, 15 nucleotides or more), such that displacement of the bottom strand of the non-labeled double-stranded DNA molecule is favored thermodynamically versus displacement of the bottom strand of the fluorescently labeled double-stranded DNA molecule.

In some embodiments of the disclosed compositions, systems, kits, and methods, multiple ATFs and/or multiple engineered transcription templates may be included and/or utilized. For example, multiple ATFs and/or multiple engineered transcription templates may be included and/or utilized in order to create logic gates.

The disclosed compositions, systems, kits, and methods may be utilized to detect one or more analytes or target molecules (i.e., multiple analytes or target molecules) in a sample. In some embodiments, the disclosed compositions, systems, kits, and methods may include or utilize: (a) one or more RNA polymerases; and (b) two or more ATFs; and/or (c) two or more engineered transcription templates. In some embodiments, the compositions, systems, kits, and methods may include or utilize: (a) one or more RNA polymerases; (b)(i) a first allosteric transcription factor (ATF), wherein one or more of the analytes or target molecules is a ligand to which the first ATF binds; (b)(ii) a second allosteric transcription factor (ATF), wherein one or more of the analytes or target molecules is a ligand to which the second ATF binds; (c)(i) a first engineered transcription template, the first engineered transcription template comprising a promoter sequence for the RNA polymerase and an operator sequence for first ATF operably linked to a sequence encoding a first RNA, wherein the first ATF modulates transcription of the encoded first RNA when the first ATF binds the analyte or target molecule as a ligand; and (c)(ii) a second engineered transcription template, the second engineered transcription template comprising a promoter sequence for the RNA polymerase and an operator sequence for the second ATF operably linked to a sequence encoding a second RNA, wherein the second ATF modulates transcription of the encoded second RNA when the second ATF binds the analyte or target molecule a ligand. In these embodiments, the first transcribed RNA, the second transcribed RNA, and a reporter molecule form a complex that generates a detectable signal. In some embodiment, the first transcribed RNA and the second transcribed RNA interact, for example, to form at least a partially double stranded RNA complex (e.g., an aptamer generated from split parts) which binds to the reporter molecule, where binding of the RNA complex to the reporter molecule generates a detectable signal. In some embodiments, the first transcribed RNA and the second transcribed RNA interact to form a fluorescence-activating aptamer, which may include but is not limited to a Split-Broccoli aptamer. The fluorescence-activating aptamer formed from the first transcribed RNA and the second transcribed RNA may bind and activate the fluorescence of a dye (e.g., by forming a fluorescent complex) to generate the detectable signal. In some embodiments, the first transcribed RNA and the second transcribed RNA interact to inhibit the formation of a fluorescence-activating aptamer, which may include but is not limited to a 3WJdB aptamer. In some embodiments, the first transcribed RNA interacts with the ATF and inhibits its ability to bind to its operator, thus increasing the production of the second RNA which may include but is not limited to a fluorescence-activating aptamer. Suitable dyes that are activated by the transcribed aptamer may include but are not limited to 4-hydroxybenzlidene imidazolinone (HBI)-derivative dye, such as (5Z)-5-[(3,5-Difluoro-4-hydroxyphenyl)methylene]-3,5-dihydro-2,3-dimethyl-4H-Imidazol-4-one, (Z)-4-(3,5-Difluoro-4-hydroxybenzylidene)-1,2-dimethyl-1H-imidazol-5(4H)-one (DFHBI); (5Z)-5-[(3,5-Difluoro-4-hydroxyphenyl)methylene]-3,5-dihydro-2-methyl-3-(2,2,2-trifluoroethyl)-4H-imidazol-4-one (DFHBI-1T); 3,5-difluoro-4-hydroxybenzylidene imidazolinone-2-oxime (DFHO), thiazole orange dyes (e.g., TO1-Biotin), and Malachite Green.

The compositions, systems, kits, and methods disclosed herein further may include or utilize additional components, such as additional components for performing RNA transcription. Additional components may include but are not limited to one or more of ribonucleoside triphosphates, an aqueous butter system that includes a reducing agent such dithiothreitol (DTT), divalent cations such as $Mg^{++}$, spermidine, an inorganic pyrophosphatase, an RNase inhibitor, crowding agents, and monovalent salts (e.g., NaCl and K-glutamate).

The components of the disclosed compositions, systems, kits, and methods may be mixed. For example, the components of the disclosed compositions, systems, kits, and methods may be mixed as an aqueous solution and/or may be dried or lyophilized to prepare a dried mixture which may be reconstituted (e.g., to perform the methods disclosed herein).

The disclosed compositions, systems, and kits, and the components thereof may be utilized in methods for detecting an analyte or target molecule in a sample (e.g., by performing an RNA transcription reaction). The methods may include contacting one or more components of the disclosed compositions, systems, and kits with the sample and detecting a detectable signal, thereby detecting the analyte or target molecule in the sample.

ILLUSTRATIVE EMBODIMENTS

The following embodiments are illustrative and should not be interpreted to limit the scope of the claimed subject matter Embodiment 1. A composition, system, or kit for detecting an analyte comprising as components: (a) an RNA polymerase; (b) an allosteric transcription factor (ATF), wherein the analyte is a ligand to which the ATF binds; (c) an engineered transcription template, the engineered transcription template comprising a promoter sequence for the RNA polymerase and an operator sequence for the ATF operably linked to a sequence encoding an RNA, wherein the ATF modulates transcription of the encoded RNA when the ATF binds the analyte as a ligand and wherein the transcribed RNA generates a detectable signal in conjunction with a reporter molecule.

Embodiment 2. The composition, system, or kit of embodiment 1, wherein the transcribed RNA binds to the reporter molecule which RNA binding generates a detectable signal.

Embodiment 3. The composition, system, or kit of embodiment 1, further comprising a second engineered transcription template, the second engineered transcription template comprising a promoter sequence for the RNA polymerase operably linked to a sequence encoding a second RNA, wherein the second RNA binds to the reporter molecule which second RNA binding generates a detectable signal, and the RNA transcribed from the first engineered transcription template, namely the first RNA, interacts with the second RNA and interferes with the detectable signal generated by the second RNA binding to the reporter molecule.

Embodiment 4. The composition, system, or kit of any of the foregoing embodiments, wherein the RNA polymerase is selected from T7 RNA polymerase, T3 RNA polymerase, SP6 RNA polymerase, and Syn5 RNA polymerase or the RNA polymerase is an engineered RNA polymerase.

Embodiment 5. The composition, system, or kit of any of the foregoing embodiments, wherein the ATF represses transcription from the engineered transcription template when the ATF binds the operator.

Embodiment 6. The composition, system, or kit of any of the foregoing embodiments, wherein the ATF activates transcription from the engineered transcription template when the ATF binds the operator.

Embodiment 7. The composition, system, or kit of any of the foregoing embodiments, wherein in the absence of the analyte as a ligand the ATF binds to the operator sequence.

Embodiment 8. The composition, system, or kit of any of embodiments 1-6, wherein in the presence of the analyte as a ligand the ATF does not bind to the operator or binds to the operator at a lower affinity than in the absence of the analyte as a ligand.

Embodiment 9. The composition, system, or kit of any of embodiments 1-6, wherein in the presence of the analyte as a ligand the ATF binds to the operator sequence.

Embodiment 10. The composition, system, or kit of any of embodiments 1-6, wherein in the absence of the analyte as a ligand the ATF does not bind to the operator or binds to the operator at a lower affinity than in the presence of the analyte as a ligand.

Embodiment 11. The composition, system, or kit of any of the foregoing embodiments, wherein the ATF is an engineered ATF or the ATF belongs to the TetR, MarR, or ArsR/SmtB class or family of transcription factors, optionally wherein the ATF is selected from the group consisting of the TetR, MphR, QacR, OtrR, CtcS, SAR2349, MobR, CadC, CsoR, AdcR, TtgR, HucR and SmtB.

Embodiment 12. The composition, system, or kit of any of the foregoing embodiments, wherein the analyte that is a ligand for the ATF is a member of the tetracycline-family of antibiotics.

Embodiment 13. The composition, system, or kit of any of embodiments 1-11, wherein the analyte that is a ligand for the ATF is a member of the macrolide-family of antibiotics.

Embodiment 14. The composition, system, or kit of any of embodiments 1-11, wherein the analyte is a quaternary amine or salts thereof (e.g., benzalkonium chloride).

Embodiment 15. The composition, system, or kit of any of embodiments 1-11, wherein the analyte is a metal or a cation thereof, optionally wherein the metal or the cation thereof is Zn, Pb, Cu, Cd, Ni, As, or Mn.

Embodiment 16. The composition, system, or kit of embodiment 15, wherein the analyte is selected from uric acid, 3-hydroxy benzoic acid, narigenin, and salicylate.

Embodiment 17. The composition, system, or kit of any of the foregoing embodiments, wherein the transcribed RNA is a fluorescence-activating aptamer.

Embodiment 18. The composition, system, or kit of any of the foregoing embodiments, wherein the transcribed RNA is a fluorescence-activating aptamer selected from the group consisting of Malachite Green aptamer, Mango aptamer, and the Spinach/Broccoli family of aptamers.

Embodiment 19. The composition, system, or kit of embodiment 17 or 18, wherein the system further comprises (d) a dye, wherein the aptamer binds and activates the fluorescence of the dye (e.g., by forming a fluorescent complex) to generate the detectable signal.

Embodiment 20. The composition, system, or kit of embodiment 19, wherein the dye is a 4-hydroxybenzlidene imidazolinone (HBI)-derivative dye, such as (5Z)-5-[(3,5-Difluoro-4-hydroxyphenyl)methylene]-3,5-dihydro-2,3-dimethyl-4H-Imidazol-4-one, (Z)-4-(3,5-Difluoro-4-hydroxybenzylidene)-1,2-dimethyl-1H-imidazol-5(4H)-one (DFHBI); (5Z)-5-[(3,5-Difluoro-4-hydroxyphenyl)methylene]-3,5-dihydro-2-methyl-3-(2,2,2-trifluoroethyl)-4H-imidazol-4-one (DFHBI-1T); 3,5-difluoro-4-hydroxybenzylidene imidazolinone-2-oxime (DFHO), thiazole orange dyes (e.g., TO1-Biotin), and Malachite Green.

Embodiment 21. The composition, system, or kit of any of embodiments 17-20, wherein the aptamer is a three-way junction dimeric Broccoli (3WJdB) aptamer.

Embodiment 22. The composition, system, or kit of any of embodiments 1-16, wherein the reporter molecule is a fluorescently labeled double-stranded nucleic acid (e.g., which functions as an output gate) comprising a fluorophore and a quencher that quenches the fluorophore in the fluorescently labeled double-stranded nucleic acid and the transcribed RNA displaces one of the strands of the fluorescently labeled double-stranded nucleic acid which results in dequenching of the fluorophore to generate the detectable signal.

Embodiment 23. The composition, system, or kit of embodiment 22, wherein the reporter molecule is a fluorescently labeled double-stranded DNA molecule (e.g., which functions as an output gate) comprising a top strand having a fluorophore conjugated at its 3'-end and a bottom strand having a quencher conjugated at its 5' end that quenches the fluorophore in the fluorescently labeled double-stranded DNA molecule and the transcribed RNA displaces the bottom strand of the fluorescently labeled double-stranded DNA molecule which results in dequenching of the fluorophore to generate the detectable signal.

Embodiment 24. The composition, system, or kit of embodiment 23, wherein the top strand is longer than the bottom strand (e.g., by about 1, 2, 3, 4, 5, 6, 7, 8, 9, 10, 11, 12, 13, 14, 15 nucleotides or more) and wherein the transcribed RNA comprises a sequence that is complementary to the full length of the top strand.

Embodiment 25. The composition, system, or kit of any of embodiments 22-24, wherein the system further comprises a non-labeled double-stranded DNA molecule (e.g., which functions as a threshold gate) comprising a top strand that comprises a nucleotide sequence that is identical to the nucleotide sequence of the top strand of the labeled double-stranded DNA molecule.

Embodiment 26. The composition, system, or kit of embodiment 25, wherein the top strand of the non-labeled double-stranded DNA molecule is longer than the bottom strand of the non-labeled double-stranded DNA molecule (e.g., by about 1, 2, 3, 4, 5, 6, 7, 8, 9, 10, 11, 12, 13, 14, 15 nucleotides or more).

Embodiment 27. The composition, system, or kit of embodiment 25 or 26, wherein the bottom strand of the non-labeled double-stranded DNA molecule is shorter in length than the length of the bottom strand of the fluorescently labeled double-stranded DNA molecule (e.g., by about 1, 2, 3, 4, 5, 6, 7, 8, 9, 10, 11, 12, 13, 14, 15 nucleotides or more).

Embodiment 28. A composition, system, or kit for detecting one or more analytes, the system comprising as components: (a) one or more RNA polymerases; (b)(i) a first allosteric transcription factor (ATF), wherein one or more of the analytes is a ligand to which the first ATF binds; (b)(ii) a second allosteric transcription factor (ATF) which may be the same as the first ATF or different than the first ATG, wherein one or more of the analytes is a ligand to which the second ATF binds; (c)(i) a first engineered transcription template, the first engineered transcription template comprising a promoter sequence for the RNA polymerase and an operator sequence to which the first ATF is capable of binding operably linked to a sequence encoding a first RNA, wherein the first ATF modulates transcription of the encoded first RNA when the first ATF binds the analyte as a ligand; and (c)(ii) a second engineered transcription template, the second engineered transcription template comprising a promoter sequence for the RNA polymerase and an operator sequence to which the second ATF is capable of binding operably linked to a sequence encoding a second RNA, wherein the second ATF modulates transcription of the encoded second RNA when the second ATF binds the analyte as a ligand; wherein the first RNA, the second RNA, and a report molecule for a complex that generates a detectable signal.

Embodiment 29. The composition, system, or kit of embodiment 28, wherein one or more of the following occur: (i) the first RNA binds to the reporter molecule to generate a detectable signal, and the second RNA binds to the first RNA to inhibit the detectable signal; (ii) wherein the first RNA binds to the reporter molecule to generate a detectable signal, and the second RNA binds to the first ATF to interfere with the first ATF binding to its operator sequence; (iii) wherein the first RNA and the second RNA interact to form a fluorescence-activating aptamer.

Embodiment 30. The composition, system, or kit of embodiment 28 or 29, wherein the first RNA and the second RNA are part of a Split-Broccoli aptamer system.

Embodiment 31. The composition, system, or kit of any of embodiments 28-30, wherein the system further comprises (d) a dye, wherein the aptamer binds and activates the fluorescence of the dye (e.g., by forming a fluorescent complex) to generate the detectable signal.

Embodiment 32. The composition, system, or kit of embodiment 31, wherein the dye is selected from the group consisting of (5Z)-5-[(3,5-Difluoro-4-hydroxyphenyl)methylene]-3,5-dihydro-2,3-dimethyl-4H-Imidazol-4-one, (Z)-4-(3,5-Difluoro-4-hydroxybenzylidene)-1,2-dimethyl-1H-imidazol-5(4H)-one (DFHBI), (5Z)-5-[(3,5-Difluoro-4-hydroxyphenyl)methylene]-3,5-dihydro-2-methyl-3-(2,2,2-trifluoroethyl)-4H-imidazol-4-one (DFHBI-1T), 3,5-difluoro-4-hydroxybenzylidene imidazolinone-2-oxime (DFHO), thiazole orange dyes; and Malachite Green.

Embodiment 33. The composition, system, or kit of any of the foregoing embodiments further comprising (d) one or more components for preparing a reaction mixture for RNA transcription.

Embodiment 34. The composition, system, or kit of any of the foregoing embodiments, wherein the components are mixed and form an aqueous solution for performing RNA transcription.

Embodiment 35. The composition, system, or kit of any of the foregoing embodiments, wherein the components are mixed and form a dried mixture which may be reconstituted to form a reaction mixture for performing RNA transcription.

Embodiment 36. A method for detecting an analyte in a sample, the method comprising contacting the sample with one or more components of the composition, system, or kit of any of the foregoing claims and detecting a detectable signal.

EXAMPLES

The following examples are illustrative and should not be interpreted to limit the scope of the claimed subject matter.

Example 1

Title—Detection of Analytes and Target Molecules Using Regulated In Vitro Transcription
Technical Field
The technical field relates to sensors for detecting molecules and metals in aqueous solution. In particular, the technical field relates to low-cost and rapid sensors for detecting molecules such as toxins, drugs, contaminants and the like, and metals such as zinc, lead, copper and the like in aqueous solutions.
Applications
Applications of the disclosed technology include, but are not limited to: (i) Chemical testing; (ii) Chemical screening; (iii) Water quality testing; (iv) Environmental sensing; (v) Health marker sensing in human fluids (blood, urine, saliva, breast milk); (vi) Micronutrient diagnostics in water, soils, plants and animals; (vii) Drug testing; (viii) Drug discovery; (ix) Heavy metal testing; (x) Contaminant testing; (xi) Diagnostics; (xii) High-throughput screening; (xiii) Research (transcription factor screening, protein engineering); (xiv) food testing; (xv) beverage testing; (xvi) agriculture; (xvii) aquaculture; and (xviii) animal health.
Advantages
The advantages of the disclosed technology include, but are not limited to: (i) speed, where the methods can be performed within minutes; (ii) low cost, where the cost for performing the methods is less than a few dollars to pennies per sample; (iii) robustness, where the methods can be performed using a variety of samples; (iv) reproducibility, where the technology utilizes biochemically defined reactions; (v) ease of use, where the methods may be performed using handheld and portable components; (vi) methods are performed in vitro and do not involve replicating components (e.g., cells); and (vii) extensibility and adaptability, where the methods may be performed to detect a variety of target molecules and analytes.
Brief Summary of the Technology
The technology disclosed herein relates to in vitro transcription reaction that are regulated by allosteric transcription factors. The technology is further described in Example 2 of this disclosure below.
Technical Description
Our Regulated In Vitro Transcriptional Sensor (RIViTS) system includes an RNA polymerase, a transcription template, and an allosteric transcription factor (ATF). The RNA polymerase is a single-subunit phage polymerase, which enables robust transcription. The transcription template contains a promoter for transcription by the phage polymerase, followed by an operator site for binding of the ATF, and a transcription product that can directly activate a reporter without requiring protein synthesis. When an ATF is bound to the transcription template, transcription is repressed.

When a specific ligand is present, the ATF becomes unbound, allowing transcription to proceed and resulting in a detectable output.

We have demonstrated that this platform can be used for biosensing through the use of a fluorescence-activating RNA aptamer and a DNA strand-invasion/strand-displacement mechanism that unlocks fluorescence of an otherwise quenched fluorophore.

We have demonstrated modularity of the system by utilizing different input polymerases, analytes, operator sequences, and outputs. Furthermore, we have demonstrated that RIViTS can be utilized with different genetic circuit processing elements that extend the platform to the use of different types of ATFs, processing of multiple input analytes, and circuits that enable quantification of input analyte concentration.

Commercialization

Currently, there are only a handful of methods to perform chemical analysis on-site and they are limited to crude analysis like pH, salinity, total dissolved solids, total nitrates, etc. Off-site, several technologies exist but they require sophisticated chemical analysis equipment and techniques (chromatography, mass spectrometry, etc.), as well as the requisite expertise to perform the analysis. The unmet need is the ability to rapidly (minutes) test for analytes of interest at low-cost at any desired field location.

REFERENCES

Pardee, K. et al. Paper-Based Synthetic Gene Networks. *Cell* 1-22 (2014). doi:10.1016/j.cell.2014.10.004

Pardee, K. et al. Rapid, Low-Cost Detection of Zika Virus Using Programmable Biomolecular Components. *Cell* 165, 1-25 (2016).

Salehi, A. S. M. et al. Biosensing estrogenic endocrine disruptors in human blood and urine: A RAPID cell-free protein synthesis approach. *Toxicol. Appl. Pharmacol.* 345, 19-25 (2018).

Peter L Voyvodic, Amir Pandi, Mathilde Koch, Jean-Loup Faulon, Jerome Bonnet. Plug-and-Play Metabolic Transducers Expand the Chemical Detection Space of Cell-Free Biosensors. Nat Commun 10, 16974 (2019).

Soltani, M., Davis, B. R., Ford, H., Nelson, J. A. D. & Bundy, B. C. Reengineering cell-free protein synthesis as a biosensor: Biosensing with transcription, translation, and protein-folding. *Biochemical Engineering Journal* 138, 165-171 (2018).

Heili, J. M. et al. Real-Time Visualization of in Vitro Transcription of a Fluorescent RNA Aptamer: An Experiment for the Upper-Division Undergraduate or First-Year Graduate Laboratory. *Journal of Chemical Education* 95, 1867-1871 (2018).

Hofer, K., Langejürgen, L. V. & Jäschke, A. Universal aptamer-based real-time monitoring of enzymatic RNA synthesis. *J. Am. Chem. Soc.* 135, 13692-13694 (2013).

Paige, J. S., Wu, K. Y. & Jaffrey, S. R. RNA mimics of green fluorescent protein. 333, 642-646 (2011).

Filonov, G. S., Moon, J. D., Svensen, N. & Jaffrey, S. R. Broccoli: rapid selection of an RNA mimic of green fluorescent protein by fluorescence-based selection and directed evolution. *J. Am. Chem. Soc.* 136, 16299-16308 (2014).

Dolgosheina, E. V. et al. RNA mango aptamer-fluorophore: a bright, high-affinity complex for RNA labeling and tracking. *ACS Chem Biol* 9, 2412-2420 (2014).

Gootenberg, J. S. et al. Nucleic acid detection with CRISPR-Cas13a/C2c2. *Science* 356, 438-442 (2017).

Example 2

Title—Biosensing with Regulated In Vitro Transcription Reactions

Abstract

Allosteric transcription factors (ATFs) regulate the synthesis of RNA in response to ligand binding. ATFs have been utilized in whole-cell, reconstituted transcription-translation, and cell-extract biosensors to detect toxins, drugs, pesticides, heavy metals, and other analytes of interest. Existing whole-cell, reconstituted transcription-translation, and cell-extract biosensors rely upon the downstream synthesis of protein to convert the ligand binding ("sensing") event to an observable output, typically a fluorescent protein (e.g. GFP) or protein enzyme capable of producing a colorimetric or luminescent compound. However, the use of whole-cell biosensors raises concerns about the practicality of field-deployment, biocontainment of organisms, scalability and long-term genomic stability of the organism, and regulatory challenges arising from the use of genetically-modified organisms. Although reconstituted transcription-translation and cell-extract biosensors overcome some of these challenges, the use of reconstituted transcription-translation systems is costly, and cell-extract systems are biochemically not defined and have variable batch-to-batch performance.

Here we show, using minimal in vitro transcription reactions, that transcriptional outputs (e.g. RNA) can directly activate fast and visible reporters and that these reactions can be regulated by ATFs and an appropriately designed DNA template. By eliminating the need to translate the RNA product, regulated in vitro transcriptions also reduce the time, cost and variability associated with whole-cell, reconstituted transcription-translation and cell-extract biosensors. Regulated in vitro transcription reactions also contain minimal components consisting of a DNA template, RNA polymerase, transcription factors, buffer and an optional output producing nucleic acid. This is in contrast to all other approaches that have at least several dozen components.

Here, we describe a modular platform for the construction of biosensors based on regulated in vitro transcription reactions called RIViTS (Regulated In Vitro Transcriptional Sensors). RIViTS consist of three core elements (FIG. 1): transcription templates, RNA polymerase and an allosteric transcription factor. We demonstrate RIViTS, starting with the well-characterized TetR ATF, and describe methods for which it can be used. We also demonstrate the generalizability and modularity of the system with different input polymerases, different RNA-activated outputs (including downstream genetic processing elements), and with ATFs from a range of transcription factor families that are responsive to a variety of antimicrobial, small molecule and metal ion ligands. We also show how the RIViTS system is compatible with downstream genetic processing elements that allow information processing of biosensor inputs to create conditional and quantitative outputs.

Background

Allosteric Transcription Factors. Biological systems have evolved the ability to sense and respond to the changing conditions of their environments. In prokaryotes, these survival and proliferation mechanisms are often coordinated through allosteric transcription factors (ATFs), which are proteins that bind to ligands and consequently undergo an allosteric conformational change that involves binding, unbinding, or physical rearrangement of a DNA transcription template. The DNA binding site for an ATF is a region of sequence known as the operator and is typically found upstream of the gene(s) to be regulated and overlapping with the promoter sequence recognized by RNA polymerases to initiate transcription. Occupancy of the operator sequence by an ATF can either prevent transcription by occluding RNA polymerase binding to the promoter, or enable transcription by undergoing a conformational change that serves to recruit transcriptional machinery or make the promoter accessible to RNA polymerase. Operator binding therefore allows ATFs to directly regulate the expression of genes that encode diverse functions such as metabolism, transport, or even their own synthesis.

Due to their ability to regulate gene expression, ATFs from natural systems have been repurposed for both research and biotechnology. For synthetic biologists, ATFs enable ligand-mediated control of biological systems. Here, we focus on the use of ATFs in biosensing applications, where biomolecular or biological systems are engineered to sense and report on the presence of an analyte or analytes of interest. Rather than construct a whole-cell biosensor or rely upon undefined lysate extracts or costly biochemically-defined reconstituted transcription-translation systems, we focused on the core mechanism of transcriptional regulation (synthesis of RNA in the presence or absence of a ligand) and RNA-level outputs.

Allosteric Transcription Factors in Whole-Cell, Reconstituted Transcription-Translation, or Cell-Extract Biosensors. Whole-cell biosensors (WCBs) are unicellular organisms— either prokaryotes or more complex eukaryotic organisms like yeast—that are engineered to sense the presence or absence of an analyte of interest.' Examples include whole-cell biosensors against metals, toxins, drugs, pesticides, etc. In each of those examples, ATFs are utilized to regulate gene expression to "report" the presence of an analyte through a detectable readout, such as fluorescence or colorimetry. Reporting in a WCB is often performed through translation of a protein. Typically, these proteins either directly serve as the reporter themselves (e.g. fluorescent proteins like GFP) or indirectly report through enzymatic conversion of substrates to colorimetric or chemiluminescent compounds. Examples of the latter include luciferase (which acts upon the substrate luciferin to produce chemiluminescence), β-galactosidase (which acts upon the substrate X-gal to produce a blue color), and catecholase (which acts upon the substrate catechol to produce a blue color).

However, whole-cell biosensors are living organisms that can replicate and evolve in their application environment, which raises additional concerns regarding the regulation of genetically-modified organisms and their biocontainment. Furthermore, although these whole-cell biosensors can be generated at extremely low-cost through cell culture and fermentation processes, there remain concerns about the scalability and long-term genomic stability of engineered cells. Expression of non-native genes burdens the host organism, and single mutations in newly-introduced genes can inactivate the biosensing mechanism. In addition, the range of compounds that can be sensed by WCBs are inherently limited by cell physiology or transport. In particular, compounds that are toxic to the cell or that cannot be transported efficiently to or across the cellular membrane cannot be sensed.

Cell-extract systems (CES) or reconstituted transcription-translation systems (RTTs) based on purified transcription and translation machinery have been employed for biosensing applications. While promising and less concerning than WCBs within a regulatory context, these systems have several limitations: utilization of protein outputs causes detection to be rate-limited by translation (~1 hour), and the use of undefined cellular extracts or reconstituted systems with dozens of codependent components in a sensor can lead to batch-batch variability and limited sensitivity due to nucleases.[2] Simplifying these cell-free systems to core biosensor elements can lower their cost, decrease their variability, and improve predictability and modularity.

Transcriptional Reporters. Fluorescence-activating aptamers, such as the Malachite Green Aptamer,[3,4] the Mango aptamer,[5] and the Spinach/Broccoli family of aptamers,[6-9] are functional RNAs that bind and activate the fluorescence of otherwise non-fluorescence dyes. Both the Spinach and Broccoli aptamers have been engineered into RNA biosensors by fusing them with other ligand binding aptamers.[10,11] In this approach, ligand binding causes an allosteric structural change in a pre-synthesized RNA molecule that allows ligand binding and fluorescence, making it distinct from an approach in which ligand binding triggers RNA synthesis.

The Spinach aptamer has also been engineered into a reporter for the real-time monitoring of in vitro transcription reactions by transcribing the aptamer downstream of an RNA of interest along with a cis-cleaving hammerhead ribozyme.[12] Full-length synthesis of the RNA results in a "universal fluorescence module" that can be used to monitor and quantify the transcription reaction. A related approach utilized a variant of the Spinach aptamer (iSpinach) to measure ribozyme activity cotranscriptionally.[13] Similarly, transcription and real-time visualization of the Broccoli aptamer and a split-variant have been developed into educational kits for undergraduate and graduate education,[14,15] demonstrating the accessibility and value of monitoring of transcription reactions in real-time.

Alternatively, toehold-mediated DNA strand displacement techniques can be utilized to visualize RNA read outs in real-time. Strand displacement RNA read outs are built from an output DNA 'gate'—a double-stranded DNA consisting of a quencher strand and a fluorophore strand with a single-stranded domain called a toehold. When transcribed, an invading RNA strand with sequence complementary to the toehold can displace the quencher strand from the fluorophore strand, unlocking the fluorescent signal. DNA strand displacement is a promising way of increasing speed, since rate constants of strand displacement are two orders of magnitude greater than that of aptamer-dye binding.[16,17] They can also be used in an approach that increases the sensitivity of the system to ligand concentration, as previous work has devised autocatalytic strand displacement cascades that provide signal amplification.[18]

Results

We sought to create a new in vitro biosensing platform— RIViTS (Regulated In Vitro Transcriptional Sensors)—that creates analyte-dependent visible nucleic acid reporters. The basis of the approach is to utilize the ability of ATFs to regulate transcription as a function of specific ligand concentration to create visible nucleic acid reporters. Here, we show that simple prokaryotic repressor ATFs can be used to regulate in vitro transcription reactions through reversible binding of the DNA transcription template in response to the analyte to be sensed. The ability to regulate in vitro transcription reactions enables the use of such reactions as simple biosensors. RIViTS is composed of three core elements: transcription templates, RNA polymerase and a transcription factor. In the following sections, we show that these three components are modular and therefore can be extended to a range of polymerases, input analytes, ATFs, outputs and downstream transcriptional circuits that allow further manipulation of the output signal useful for practical biosensing applications.

In vitro transcription can be visualized in real time with fluorescence-activating RNA outputs. To demonstrate that transcription can generate a visible output in real time we utilized a commercially-available in vitro transcription kit to transcribe the Three-Way Junction dimeric Broccoli aptamer (3WJdB). 3WJdB is an engineered variant of the Broccoli aptamer and contains two discrete monomers of the Broccoli aptamer embedded within separate arms of a 3WJ scaffold (FIG. 2A).[19] Each Broccoli monomer is capable of binding a single 4-hydroxybenzlidene imidazolinone (HBI)-derivative dye, such as DFHBI-1T[20] (FIG. 2B), and activating the dye's fluorescence when irradiated with the appropriate wavelength of light.

Figure 2:
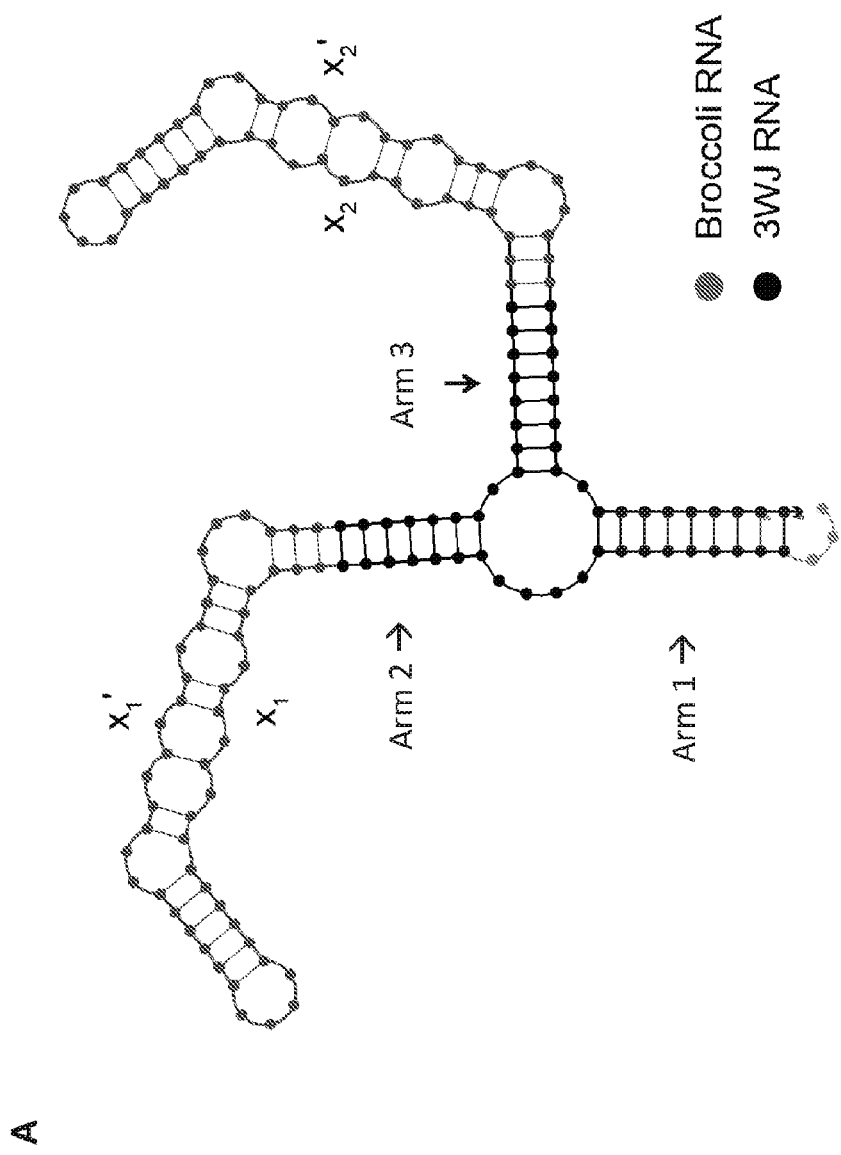
FIG. 2. Demonstration that in vitro transcription of a fluorescence-activating aptamer (3WJdB) can be visualized in real-time within minutes. In Panels D and E, the reactions have 5 pmol of transcription template in a 20 µL in vitro transcription reaction with 2.5 mM DFHBI-1T.
Figure 2:
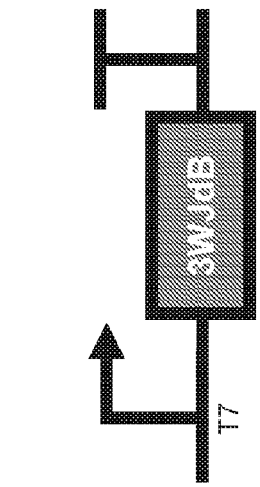
Figure 2:
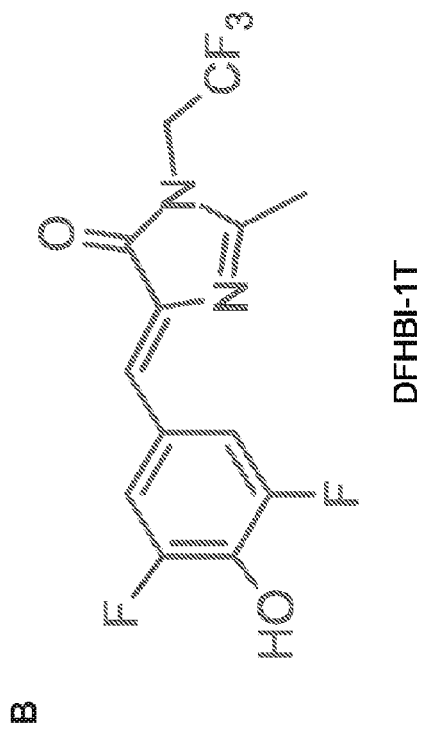
Figure 2:
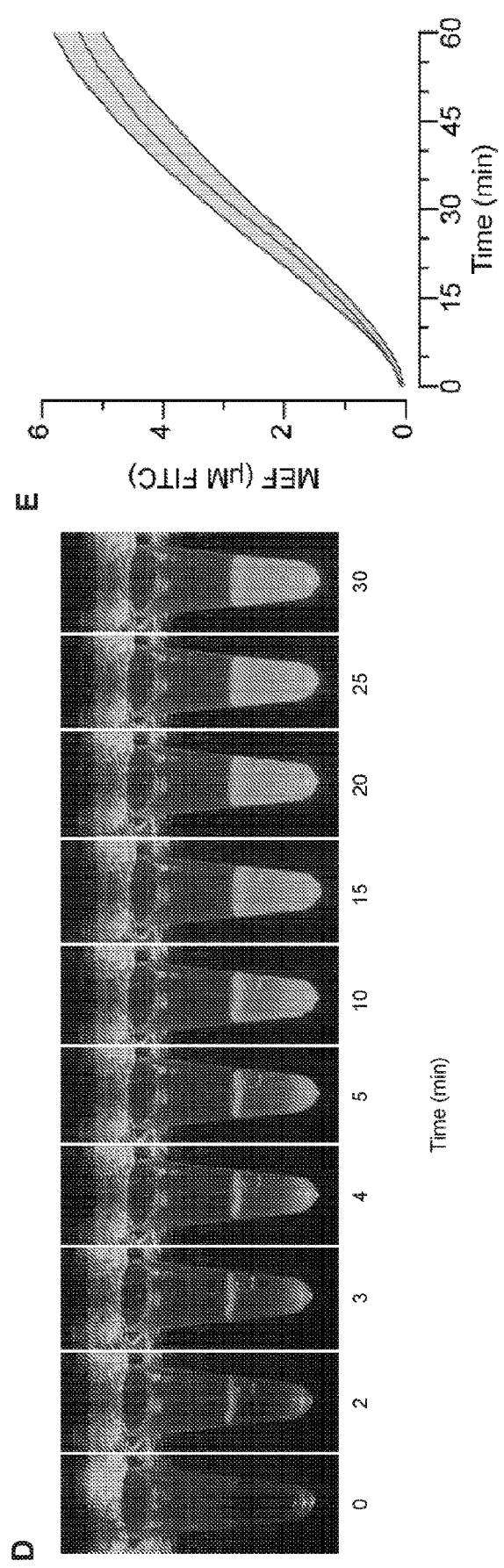

The linear double-stranded DNA transcription template for 3WJdB included a T7 promoter sequence (FIG. 2C) to enable transcription by the highly-processive, single-subunit bacteriophage T7 RNA polymerase (T7 RNAP). Transcription at 37° C. and in the presence of DFHBI-1T resulted in visible fluorescence within minutes when illuminated with a blue light source (FIG. 2D). Kinetic measurement in an incubated plate reader showed fast fluorescent signal generation, equivalent to micromolar amounts of soluble fluorescein isothiocyanate (FITC) measured under identical excitation and emission conditions (FIG. 2E).

We next transcribed a strand-invading RNA ("InvadeR") to illustrate that an alternative RNA output can also be visualized in real-time. The InvadeR system works through toehold-mediated strand displacement of a DNA output gate. The DNA output gate consists of 2 annealed and complementary strands ("reporter" and "quencher," boxed in FIG. 3A). The reporter strand consists of 24 nucleotides and a 3' fluorophore, while the quencher strand contains 16 complementary nucleotides and a 5' quencher. When annealed, the two strands leave an 8-nucleotide single-stranded "toehold" region on the 5' end of the reporter strand. Spatial proximity of the 3' fluorophore and 5' quencher results in fluorescence quenching (the "OFF" state). For the InvadeR system described here, we utilized a 3' terminal single isomer derivative of fluorescein (6-FAM) and a quencher strand with a 5' terminal Iowa Black FQ quencher. Sequences for the reporter and quencher strands were modified from Bhadra & Ellington,[21] though many other sequence designs are possible.[22] Unlike the original sequences used in Bhadra & Ellington's work, which has a toehold on the 3' end of the reporter strand, our sequences were adjusted to place the toehold on the 5' end of the reporter strand. This was done intentionally to minimize non-templated transcription of the DNA output gate by T7 RNAP.[23]

Figure 3:
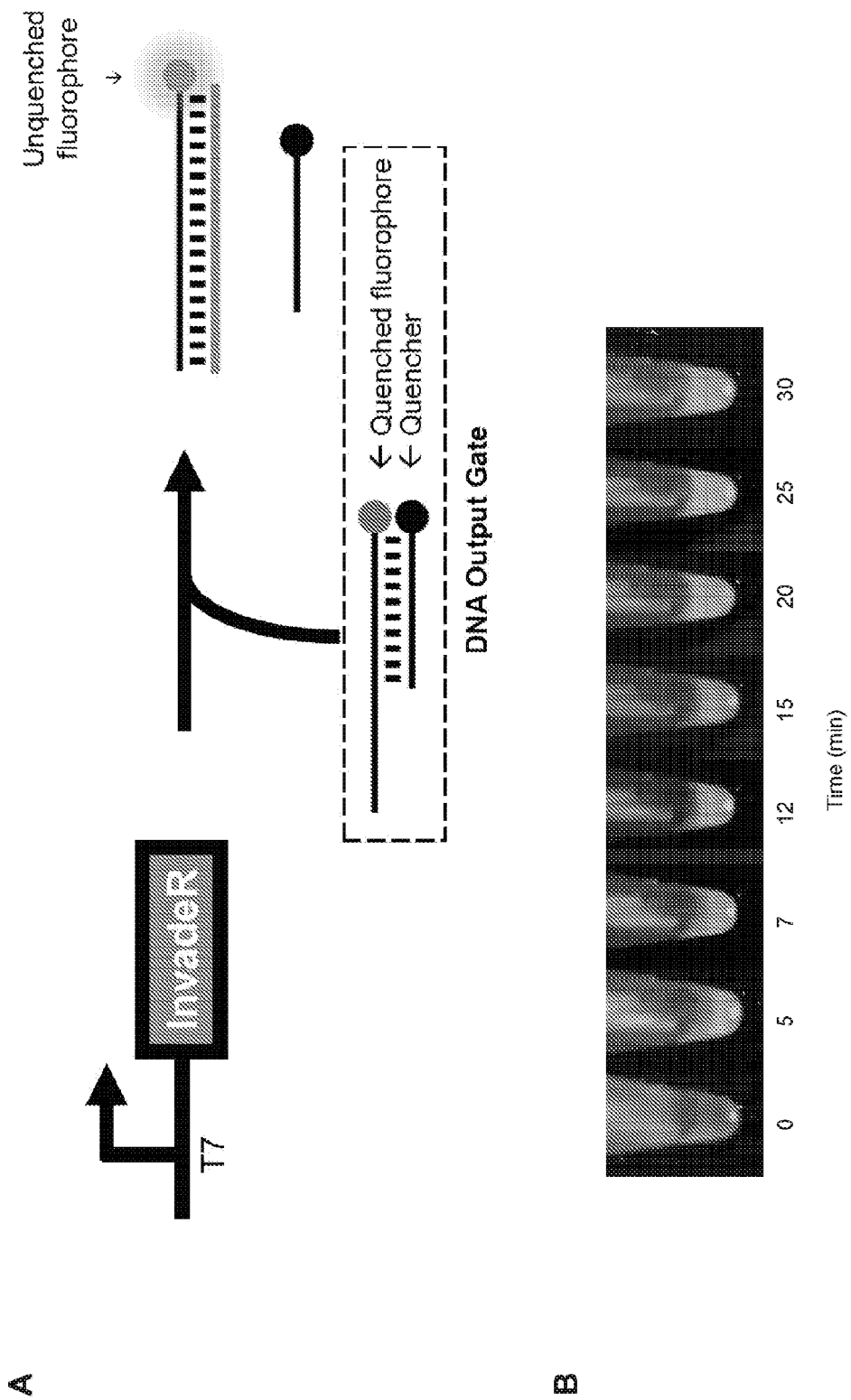
FIG. 3. Demonstration that in vitro transcription of a strand-invading RNA ("InvadeR") can be visualized in real-time within minutes.
Figure 3:
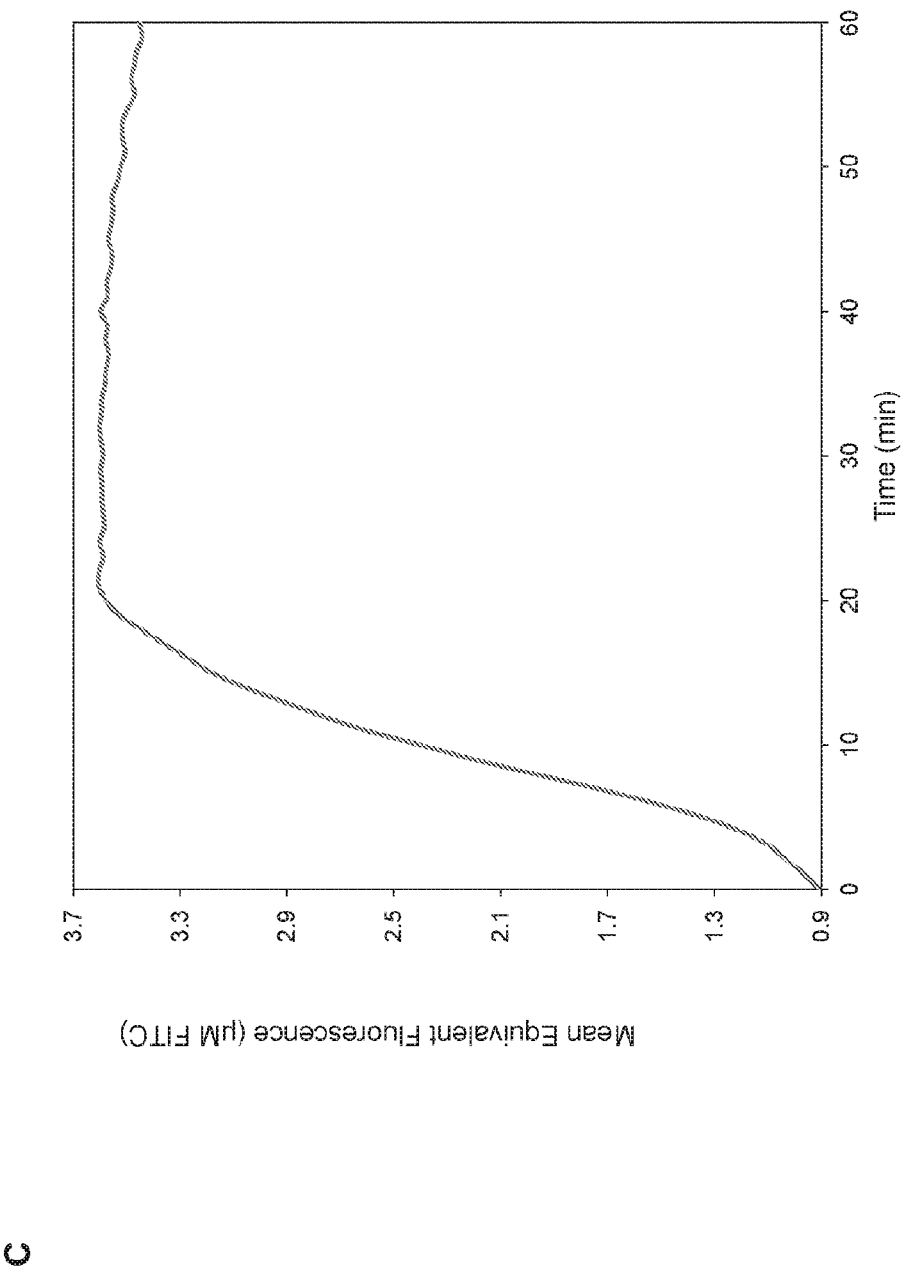

Upon transcription of the InvadeR sequence, which contains 24 nucleotides of perfect complementarity to the reporter strand, the RNA product hybridizes to the single-stranded toehold region of the DNA output gate. This initiates a strand invasion reaction that eventually displaces the quencher strand and alleviates fluorescence quenching (the "ON" state). The "ON" state is thermodynamically more stable than the "OFF" state due to the extra 8 nucleotides of complementarity between the reporter strand and the InvadeR sequence driving the strand displacement reactions forward. Similar to the design of the 3WJdB transcription template, the linear dsDNA template for InvadeR included a T7 promoter sequence to facilitate rapid transcription by T7 RNAP. As expected, transcription at 37° C. in the presence of the DNA output gate resulted in visible fluorescence within minutes when illuminated with blue light (FIG. 3B) and when measured on a plate reader (FIG. 3C).

Taken together, these results demonstrate that in vitro transcription of two different fluorescence-activating RNAs by T7 RNAP can rapidly generate a visible output within a few minutes, and that these outputs are capable of producing fluorescence equivalent to micromolar amounts of soluble fluorescein isothiocyanate. These features of fluorescence-activating RNAs make them attractive outputs for biosensing applications.

Figure 4:
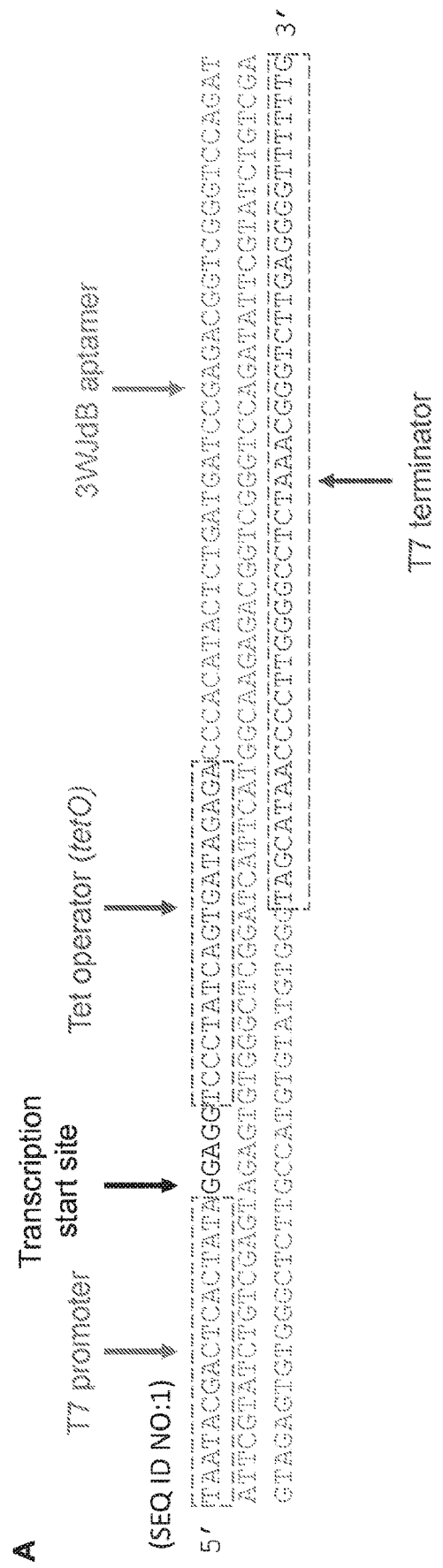
FIG. 4. Sample engineered DNA template design for TetR-regulated in vitro transcription of a fluorescence-activating aptamer.
Figure 4:
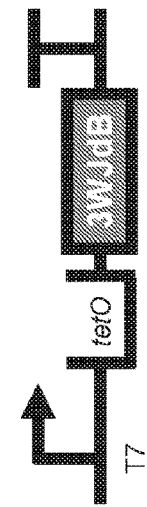
Figure 5:
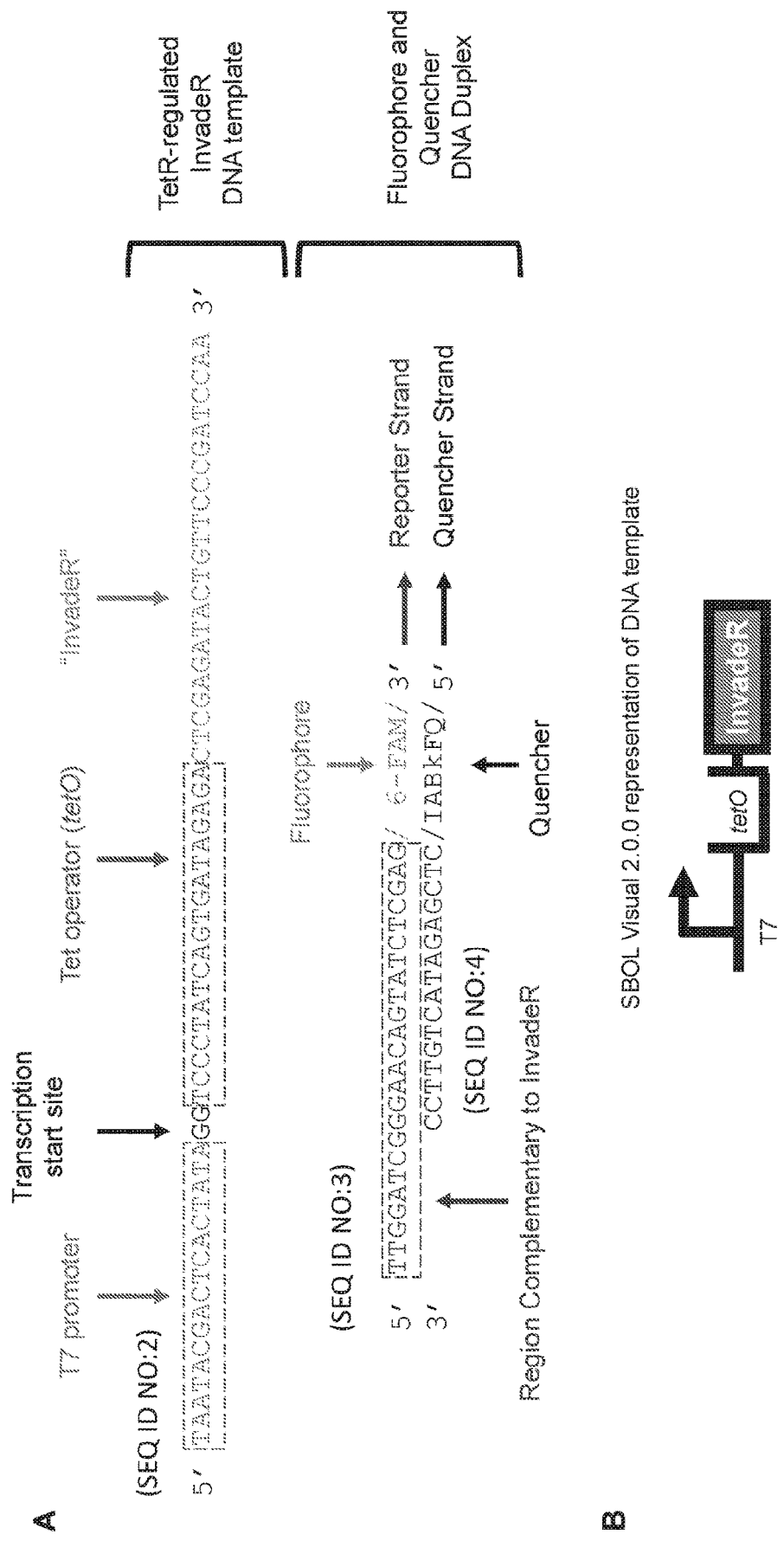
FIG. 5. Sample engineered DNA template design for TetR-regulated in vitro transcription of a strand-invading RNA (InvadeR).

In vitro transcription can be regulated by inclusion of an ATF. We next sought to establish proof-of-principle that in vitro transcriptions can be regulated using allosteric transcription factors (ATFs) and could therefore be used for biosensing applications. We reasoned that because RNA polymerases undergo a conformational change from initiation to elongation within ~10 nucleotides,[24] we could effectively block the transition to the elongation conformation by using ATFs as a roadblock to RNA polymerase and instead favor abortive initiation/transcription that would not result in fluorescence activation. To test this hypothesis, we chose to start with the well-characterized TetR repressor.[25] TetR natively controls transcription of the TetA efflux pump and has been extensively utilized as a gene regulator in both prokaryotes and eukaryotes. We designed the transcription templates to include the following: (1) an operator sequence recognized by TetR (tetO) downstream of the T7 transcription start site, (2) the preferred initiating nucleotides for T7 RNA polymerase ("GG") to ensure efficient transcription initiation, and (3) a short spacer between the transcription start site and the operator site to prevent the polymerase from switching into the more processive "elongation" conformation before transcription of the operator sequence. Transcription templates are shown in FIG. 4 for the 3WJdB reporter and FIG. 5 for the InvadeR reporter.

Figure 6:
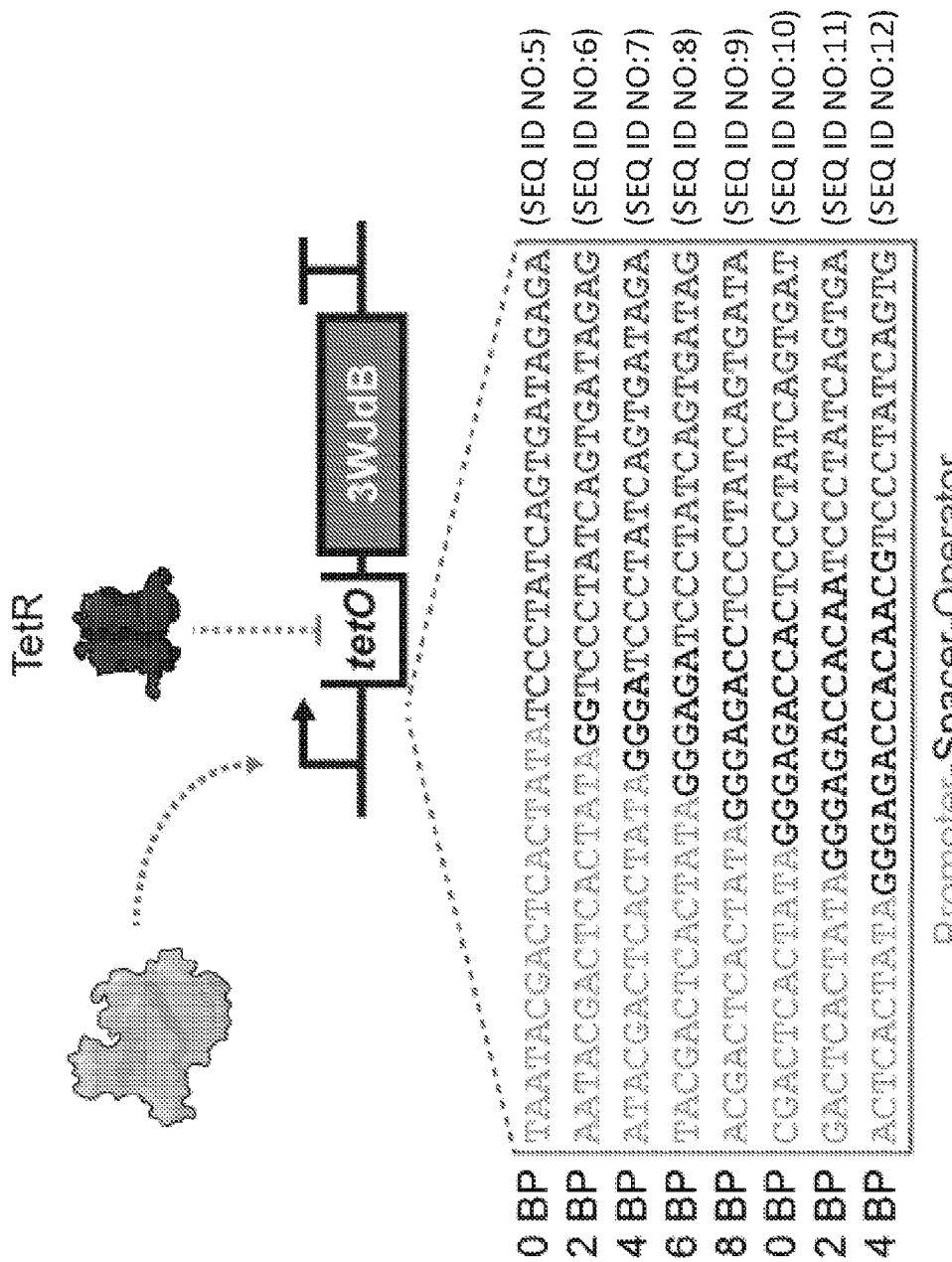
FIG. 6. Demonstration that in vitro transcription of a fluorescence-activating aptamer (3WJdB) can be allosterically regulated by engineering a synthetic transcription template configured to bind a transcription factor via the operator sequence placed downstream of the T7 promoter. In Panel B, each transcription reaction contains 0.5 pmol of transcription template in a 20 µL volume, and repressed conditions include 100 pmol of TetR. In Panel C, the kinetics traces of 4BP promoter-operator spacing are illustrated in the presence or absence of TetR.
Figure 6:
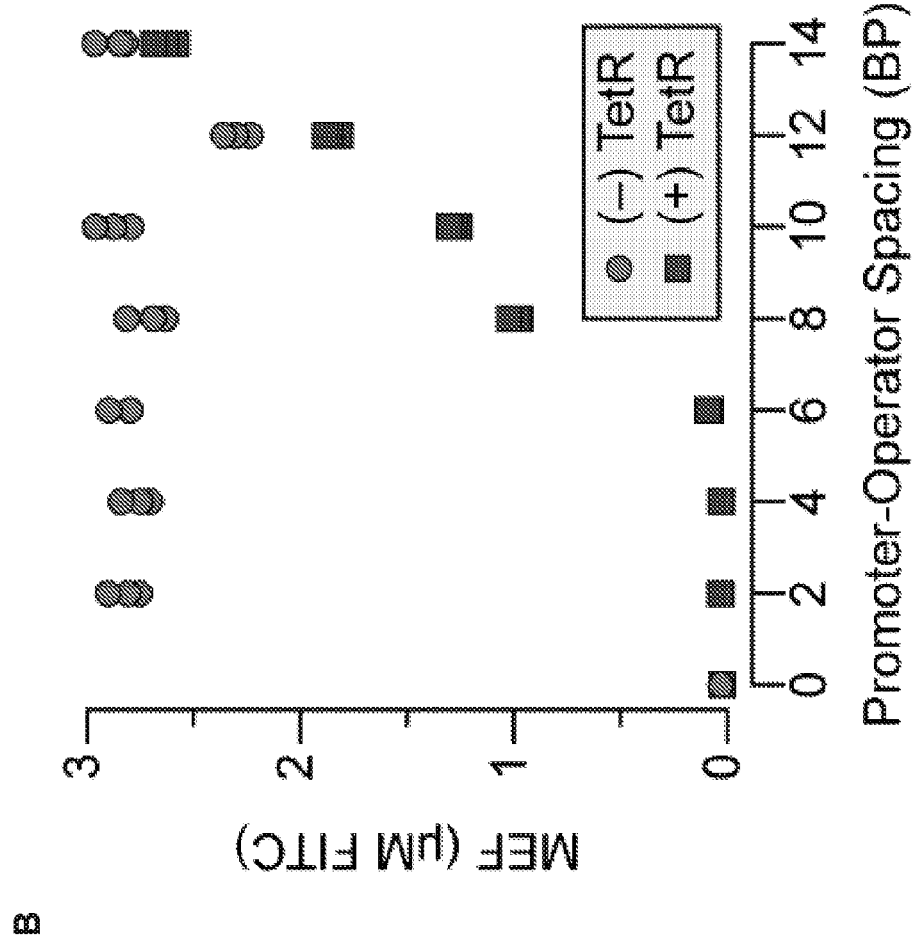
Figure 6:
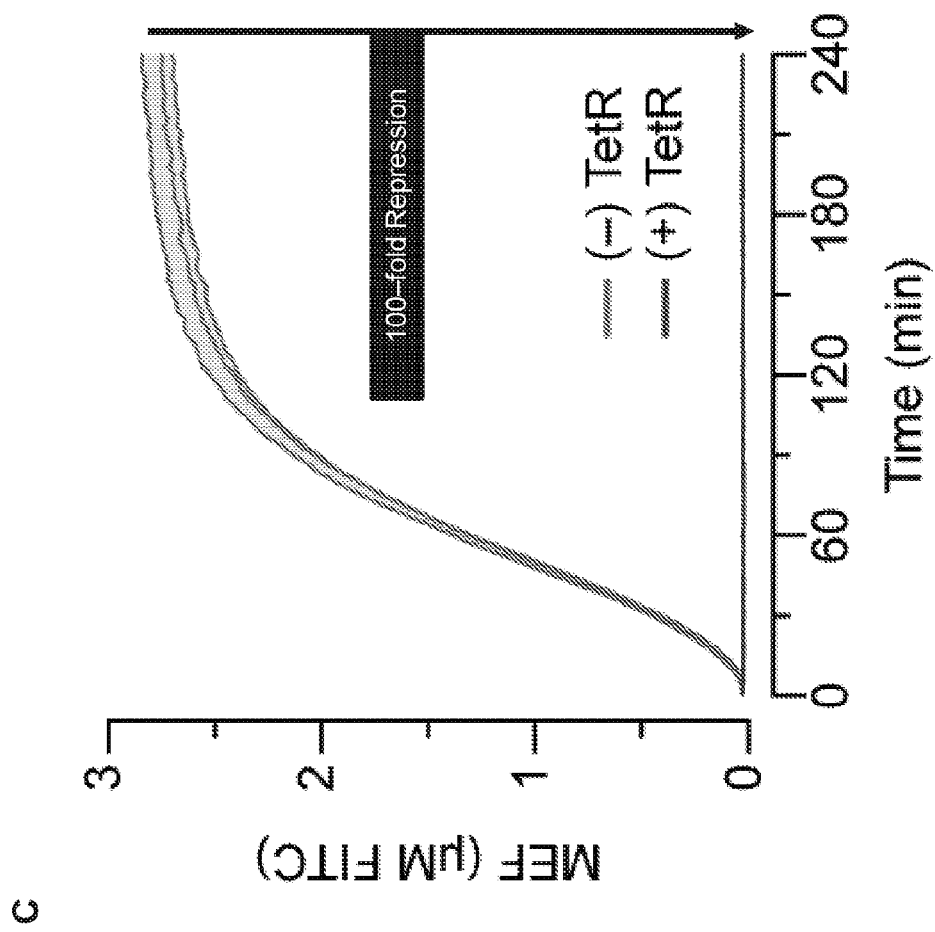

For ensuing experiments, we setup transcription reactions such that the RNA polymerase was the last addition to the reaction and was added immediately prior to incubation and measurement of fluorescent output at 37° C. In a 20 µL reaction, addition of 100 pmol of the purified TetR ATF to 1 pmol of the 3WJdB transcription reaction resulted in >10-fold repression within 15 minutes when compared to an unregulated "No TetR" control (FIG. 6). In FIG. 6, the T7 promoter was separated from the tetO binding sequence with 2, 4, or 6 basepairs. Beyond 6 BP the RNAP switches to elongation confirmation as described herein and overcomes the transcriptional repression.

Strong repression continued for the duration of the reaction and reached 62-fold reduction by 90 minutes. This result demonstrates that in vitro transcriptions can be efficiently repressed by an ATF.

Figure 7:
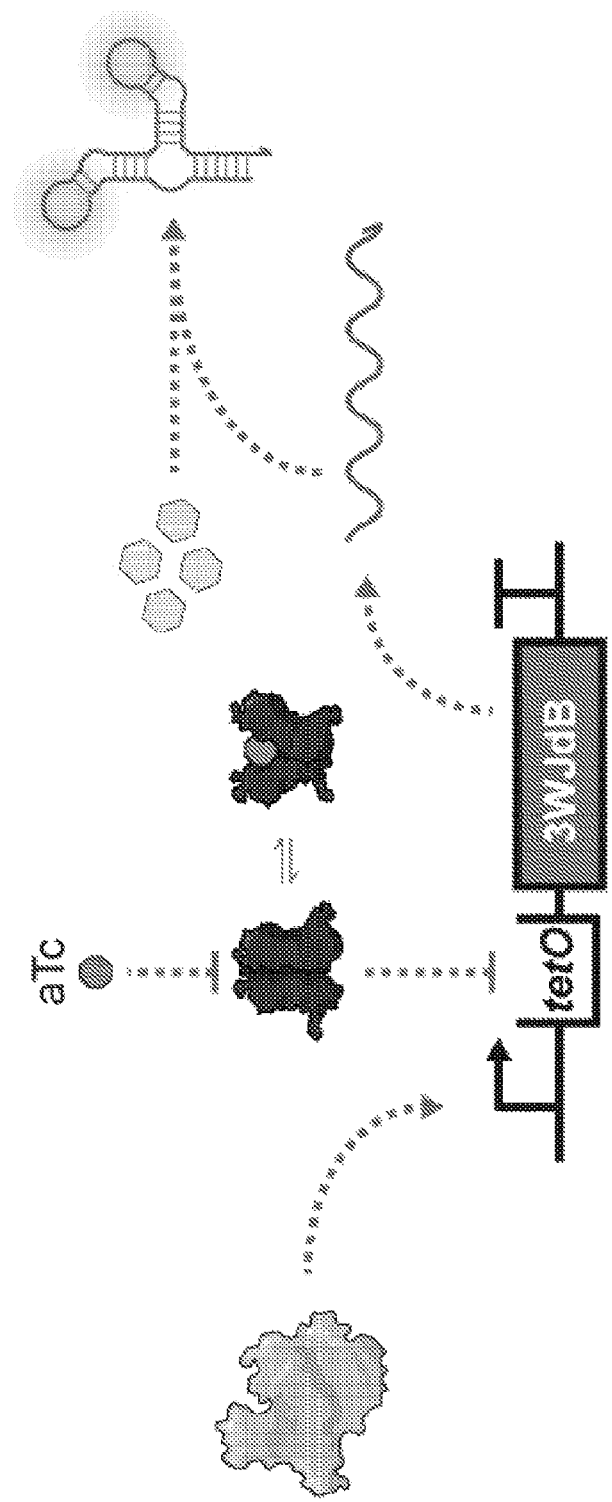
FIG. 7. Demonstration that repressed in vitro transcription of a fluorescence-activating aptamer (3WJdB) can be derepressed by including a cognate ligand of the allosteric transcription factor. In Panel B, each transcription reaction contains 1 pmol of transcription template. Induced conditions include 200 pmol of specified antibiotic. All reactions were performed in a total volume of 20 µL.
Figure 7:
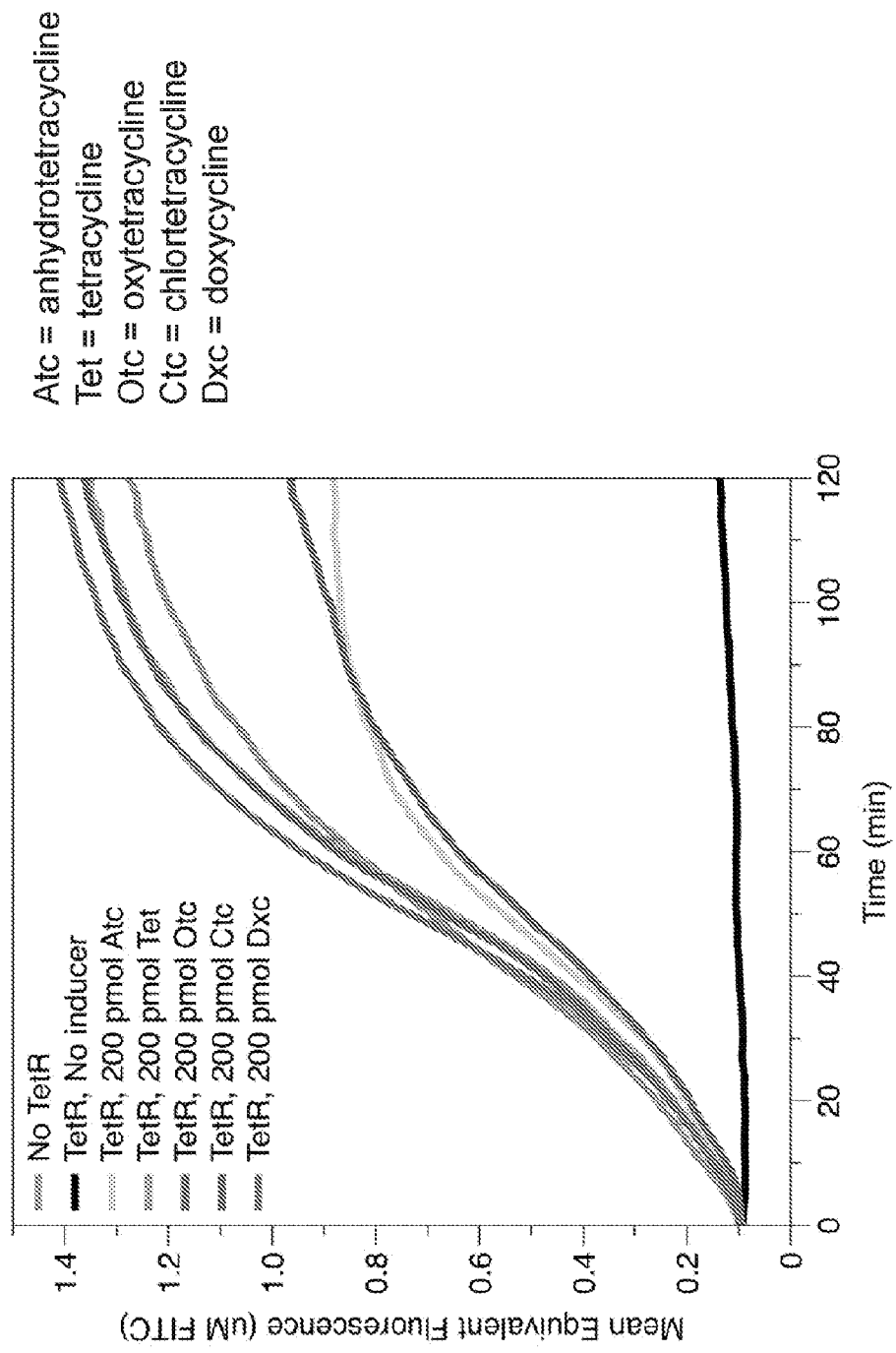
Figure 8:
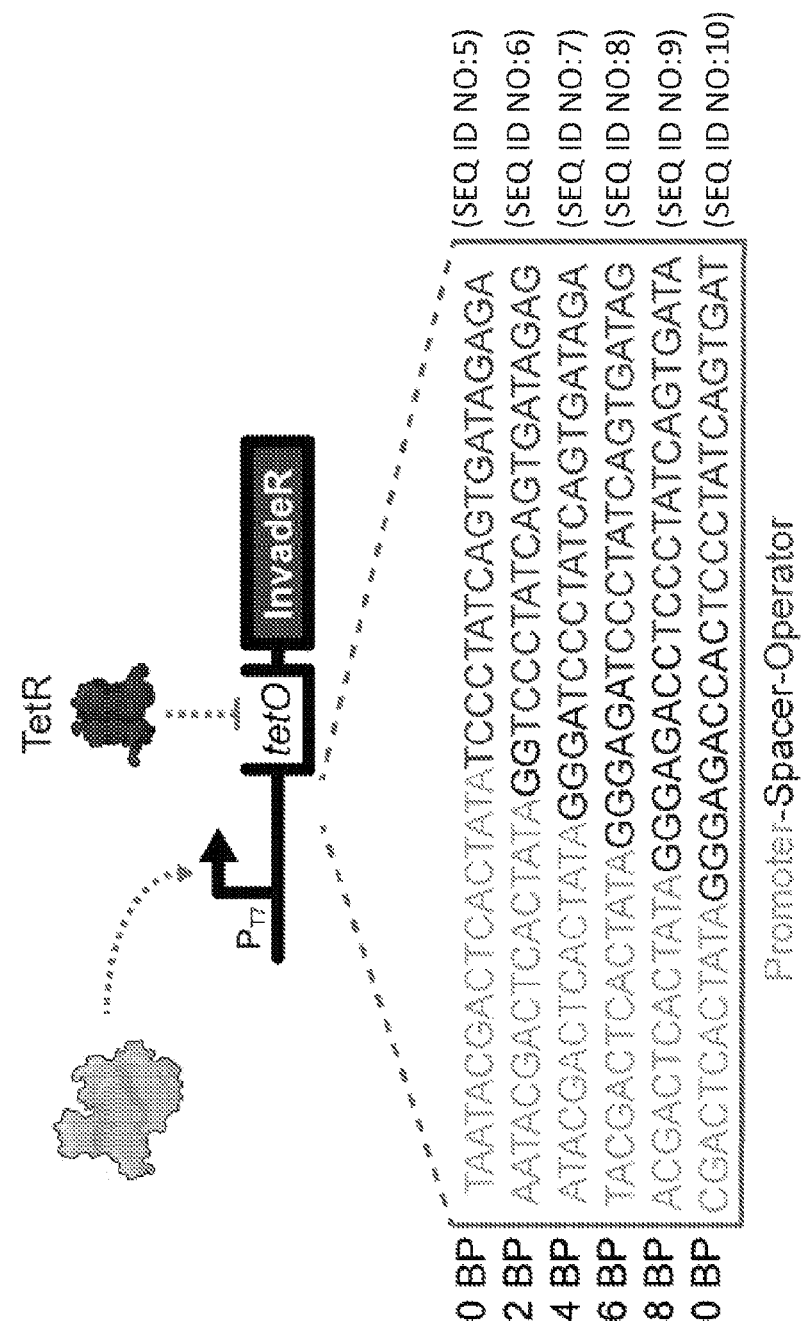
FIG. 8. Demonstration that in vitro transcription of a fluorescence-activating strand-invading RNA (InvadeR) can be allosterically regulated by engineering a synthetic transcription template configured to bind a transcription factor via the operator sequence placed downstream of the T7 promoter. In Panel B, each reaction contains 1 pmol of transcription template and 100 pmol of the DNA output gate, and repressed conditions include 200 pmol of TetR. All reactions were performed in a total volume of 20 µL. In Panel C, the kinetics traces of 2BP promoter-operator spacing are illustrated.
Figure 8:
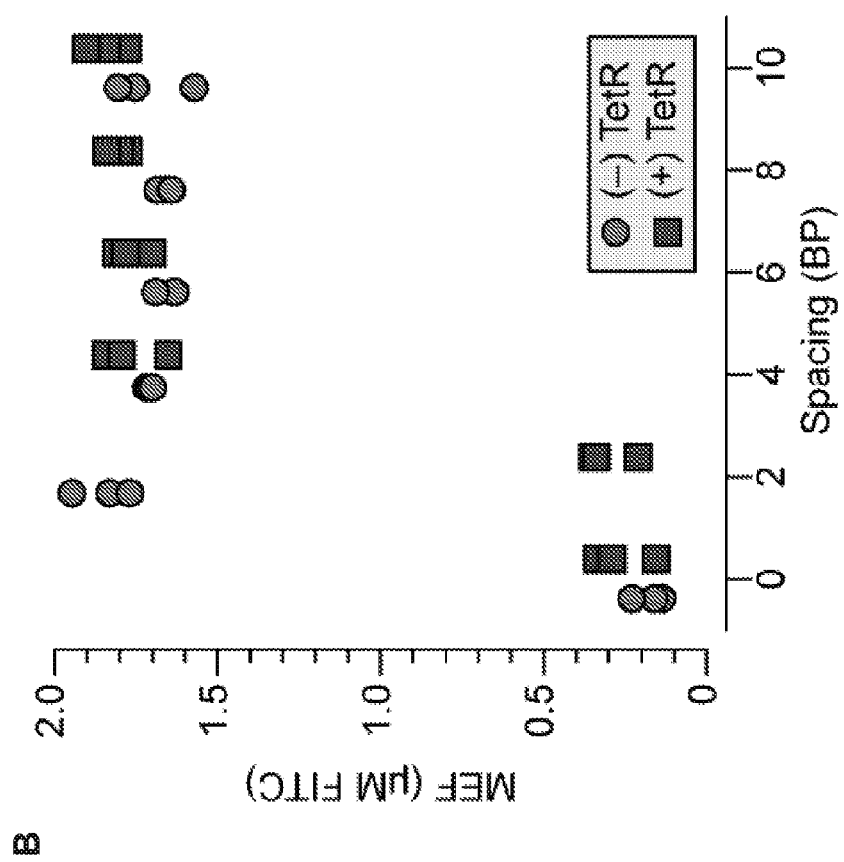
Figure 8:
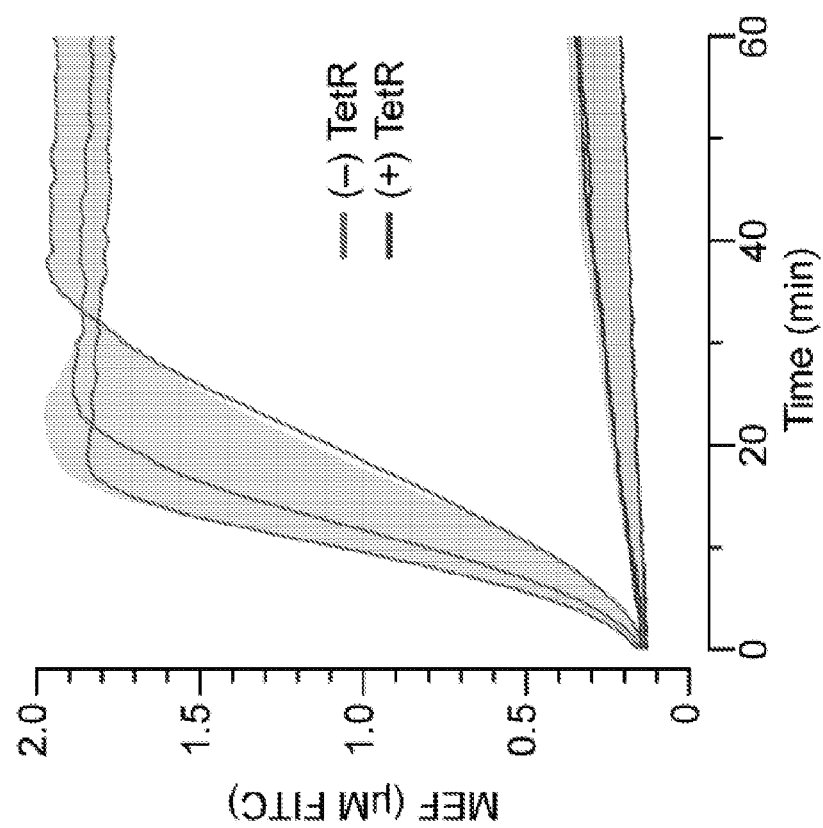
Figure 9:
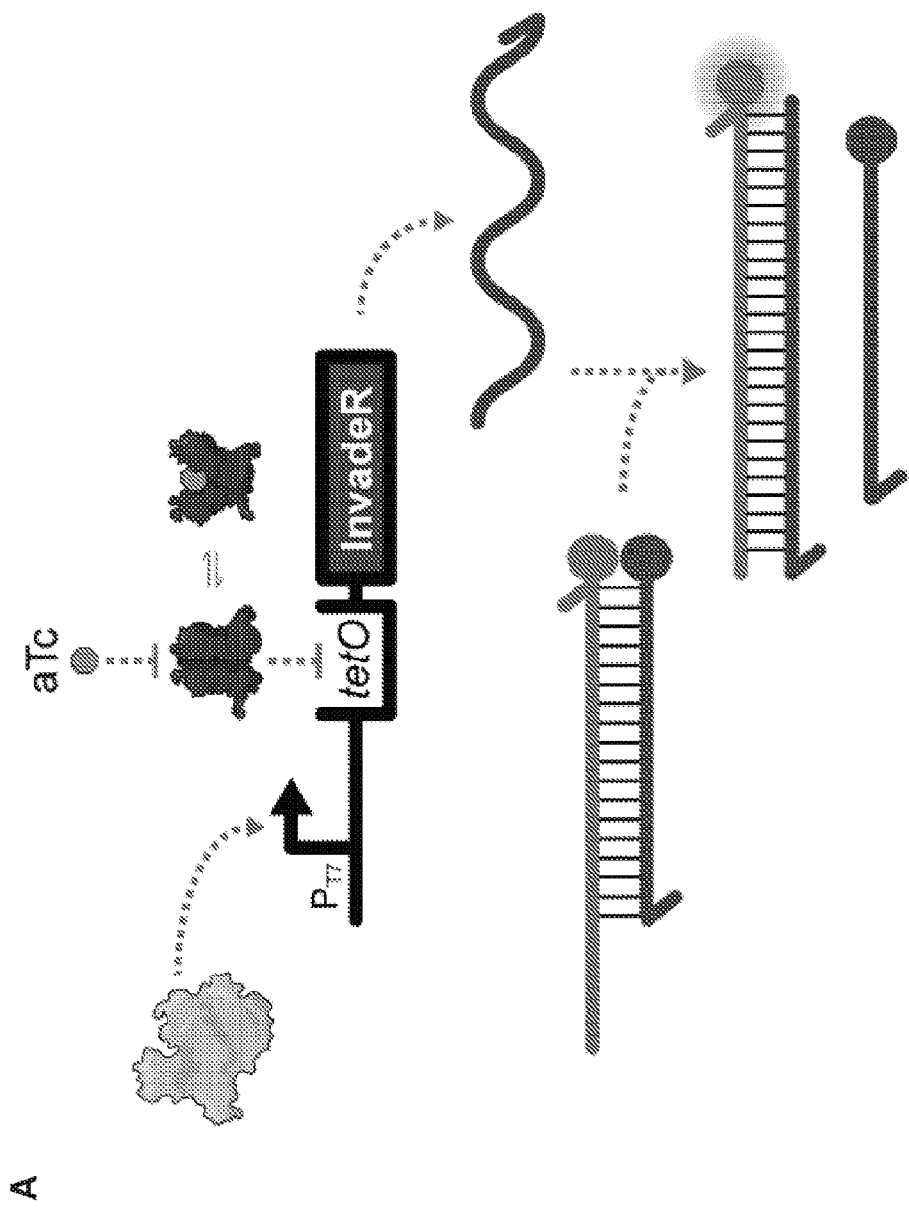
FIG. 9. Demonstration that repressed in vitro transcription of a fluorescence-activating strand-invading RNA (InvadeR) can be derepressed by including the cognate ligand of the allosteric transcription factor. In Panel B, a dose response curve, each transcription reaction contains 1 pmol of transcription template with a 2 BP spacer between promoter and operator, 100 pmol of the DNA output gate, and 200 pmol of TetR. In Panel C, the kinetics traces of 1 pmol and 100 pmol (5 µM) of aTc) are illustrated.
Figure 9:
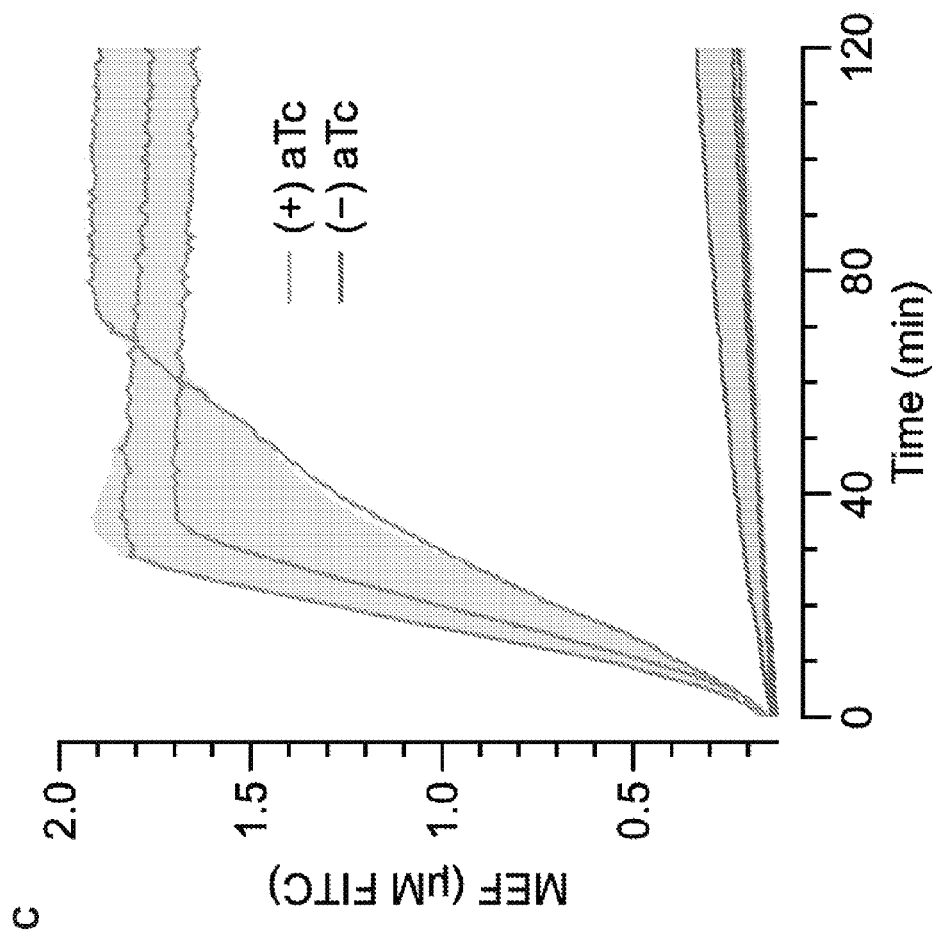

The family of tetracycline antibiotics are known ligands of the TetR repressor—they can induce an allosteric conformational change in TetR that results in a lowered affinity for the DNA operator sequence. Importantly, TetR repression of in vitro transcription is relieved if a cognate ligand is included immediately prior to measurement and coincident with the addition of T7 RNAP. Addition of 200 pmol of any of tetracycline-family antibiotics we tested in the reaction restored aptamer-activated fluorescence close to or exceeding the level of fluorescence observed for the "No TetR" control (FIG. 7). This included anhydrotetracyline, tetracycline, oxytetracycline, chlortetracycline, and doxycycline. The InvadeR system also demonstrated repression with TetR (FIG. 8) and derepression/induction upon the addition of anhydrotetracycline (FIG. 9). The results in FIG. 8 demonstrate that a 2 bp spacer between promoter and operator is ideal for achieving repression with the InvadeR system. The 2 BP spacer ("GG") promotes efficient transcription initiation with T7 RNAP. The results in FIG. 9 illustrates induction the appropriate ligand (a) and includes a dose response curve (b) and the kinetics for a fully induced condition. These results illustrate that in vitro transcriptions can be repressed in the presence of an ATF, that they can be derepressed ("induced") with an appropriate amount of cognate ligand, and that the regulation is compatible with different RNA reporter systems.

Figure 10:
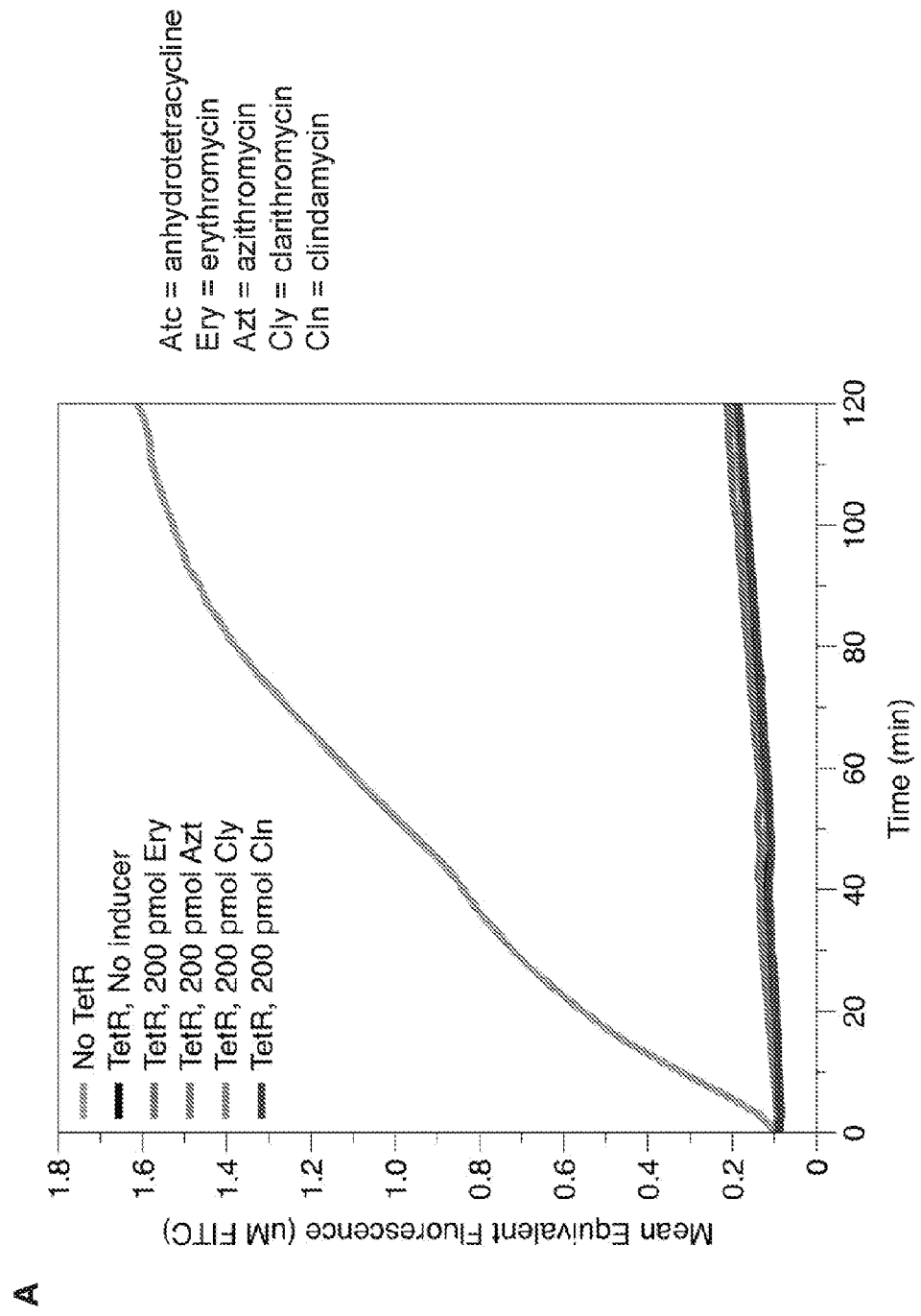
FIG. 10. Demonstration that derepression of in vitro transcription is specific for the cognate ligand and not other, related compounds. In Panel A, each transcription reaction contains 1 pmol of transcription template, and except for the "No TetR" control, each reaction also contains 100 pmol of TetR. In Panel B, each transcription reaction contains 0.5 pmol of transcription template, and except for the "No TetR" control, each reaction also contains 45 pmol of TetR.

Finally, to validate that the TetR regulated in vitro transcription reactions were specifically responsive to tetracycline antibiotics and that fluorescence was not due to nonspecific activity, we tested the TetR regulated in vitro transcription reaction of the 3WJdB output against macrolide antibiotics (FIG. 10A) as well as other common antibiotics used in biological research (FIG. 10B). None of the non-tetracycline antibiotics tested here is known to induce a conformational change in TetR. In all cases, strong repression of transcription was observed over the course of 2 hours except when tested against the positive control (anhydrotetracyline), or in the absence of the repressor (the unregulated reaction). This result demonstrated that RIViTS can be configured with a high degree of specificity for their target ligand.

The RIViTS platform responds to a range of ligand concentrations. Different RIViTS reactions were assembled using different combinations of ATFs and their corresponding engineered transcription templates that encoded 3WJdB reporters. Each reaction was then subjected to a range of concentrations of the cognate ligands of each ATF including antibiotics (FIG. 13) and small molecules and metal ions (FIG. 14). In all cases we observed an increase in signal upon increasing ligand concentration until a saturation point was achieved. In many cases we observed a sharp transition in these dose-response-curves indicating that RIViTS could be used, though not exclusively, to identify ligand concentrations above some defined threshold value.

Figure 15:
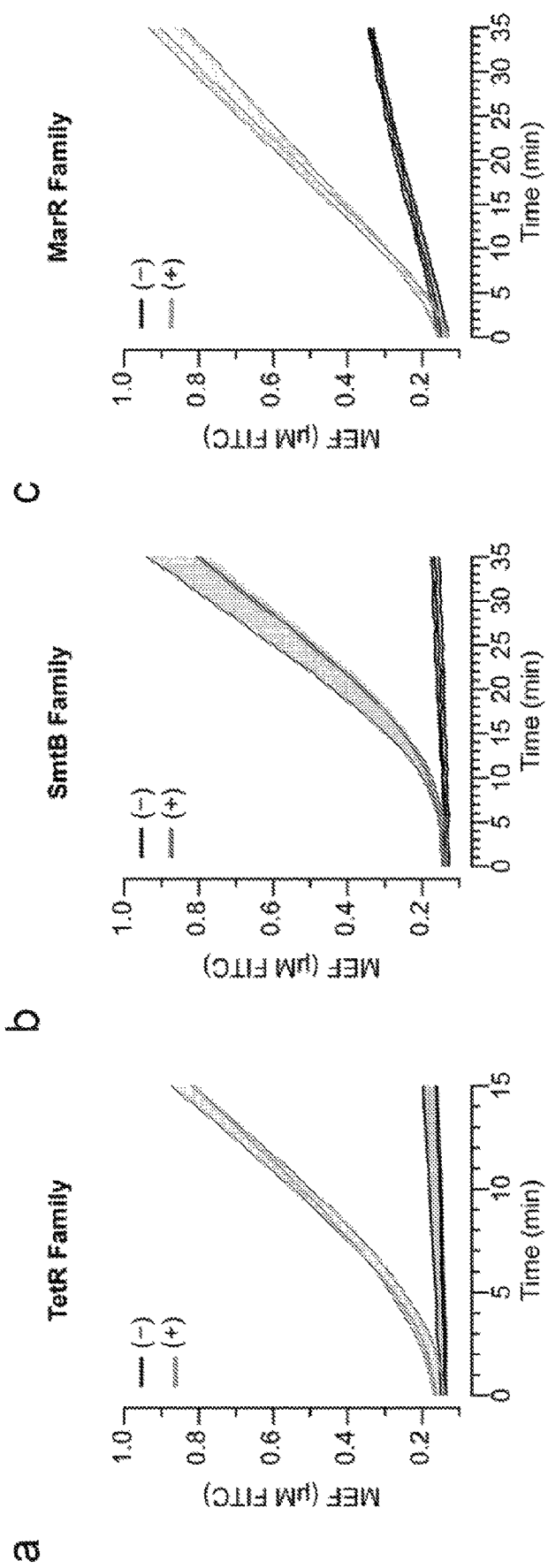
FIG. 15. Demonstration that in vitro transcriptions of fluorescence-activating strand invading RNA (InvadeR) can be regulated with a variety of transcription factors and their cognate ligands. TetR-regulated reaction (panel a) has 1 pmol of transcription template, 200 pmol of TetR, and 200 pmol of tetracycline in the (+) condition. SmtB-regulated reaction (panel b) has 1 pmol of transcription template, 100 pmol of SmtB, and 500 pmol of zinc sulfate in the (+) condition. MarR-regulated reaction (panel c) has 1 pmol of transcription template, 1000 pmol of SAR2349, and 200 nmol of salicylate in the (+) condition. All reactions have 100 pmol of the DNA output gate.

We also confirmed that RIViTS reactions configured to use DNA strand displacement as an output were able to be activated in the presence of a range of ligands. Different RIViTS reactions were assembled using different combinations of ATFs and their corresponding engineered transcription templates that generated InvadeR sequences that activated included quenched and fluorescently labeled double stranded DNA. Three different ATFs were used (TetR, SmtB, MarR) and each reaction was subjected to the cognate ligand or a no ligand control. In all cases we observed activation of signal only in the presence of the cognate ligand (FIG. 15).

Figure 11:
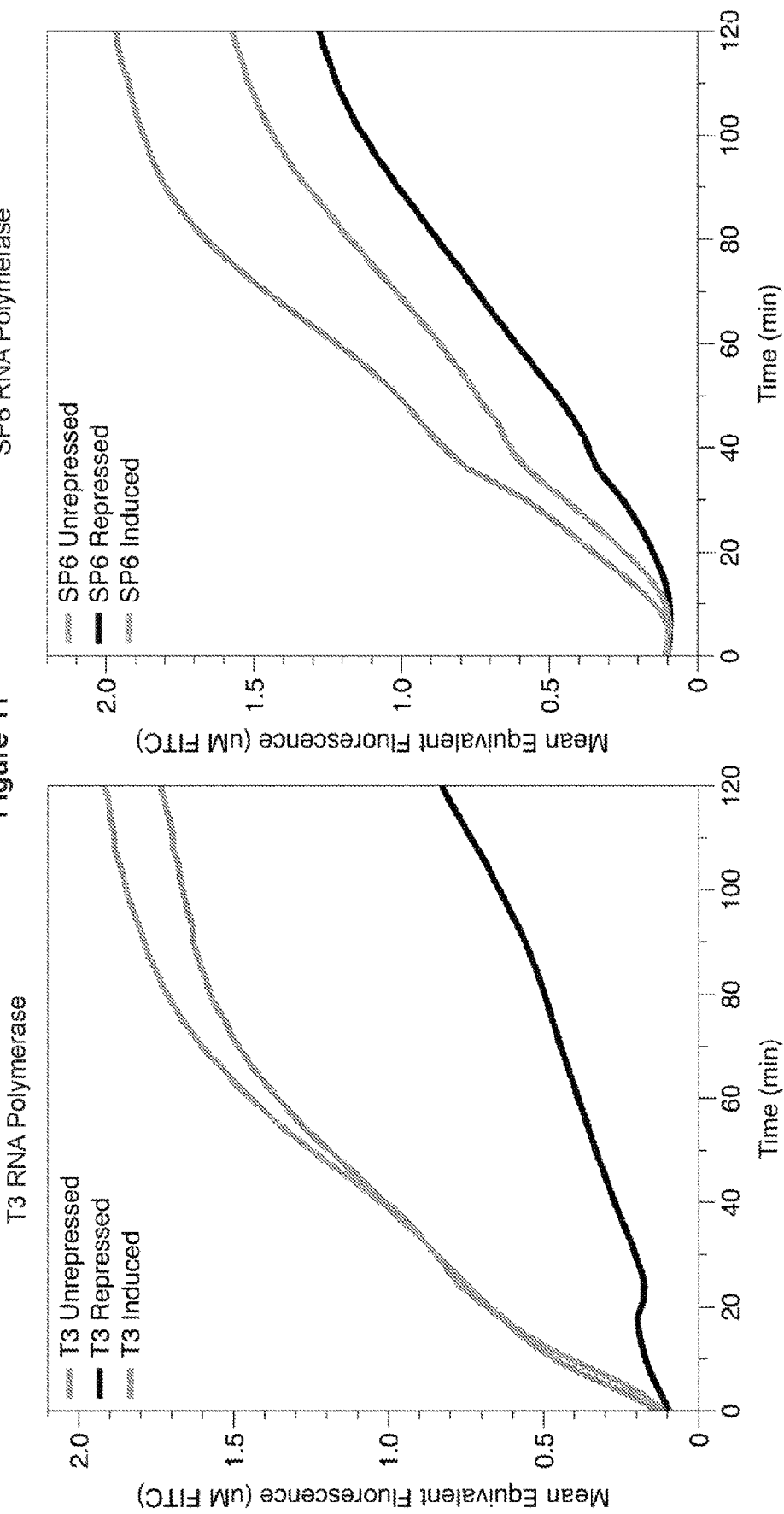
FIG. 11. Demonstration that regulated in vitro transcriptions can be performed with a variety of polymerases. Each transcription reaction contains 1 pmol of transcription template. Each induced reaction contains 200 pmol of anhydrotetracycline.

RIViTS are modular with respect to RNA polymerase. T7 RNA polymerase is a single-subunit RNA polymerase from the T7 bacteriophage. It is closely related to the T3 and SP6 bacteriophages and their RNA polymerases are homologous. We reasoned that we could swap the T7-specific promoter from the TetR regulated in vitro transcription of 3WJdB for an SP6 or T3-specific promoter, and maintain the ability to repress and induce transcription by using the appropriate RNAP. Using unoptimized transcription reactions, we show that both T3 RNAP (FIG. 11A) and SP6 RNAP (FIG. 11B) are partially repressed in the presence of TetR, and that repression is partially relieved upon addition of anhydrotetracycline. We suspect that further optimization of the transcription reaction conditions (e.g. buffer composition) will substantially improve the fold-change between the repressed and derepressed states. These data indicate that RIViTS can be engineered to be modular with respect to RNA polymerase.

Figure 12:
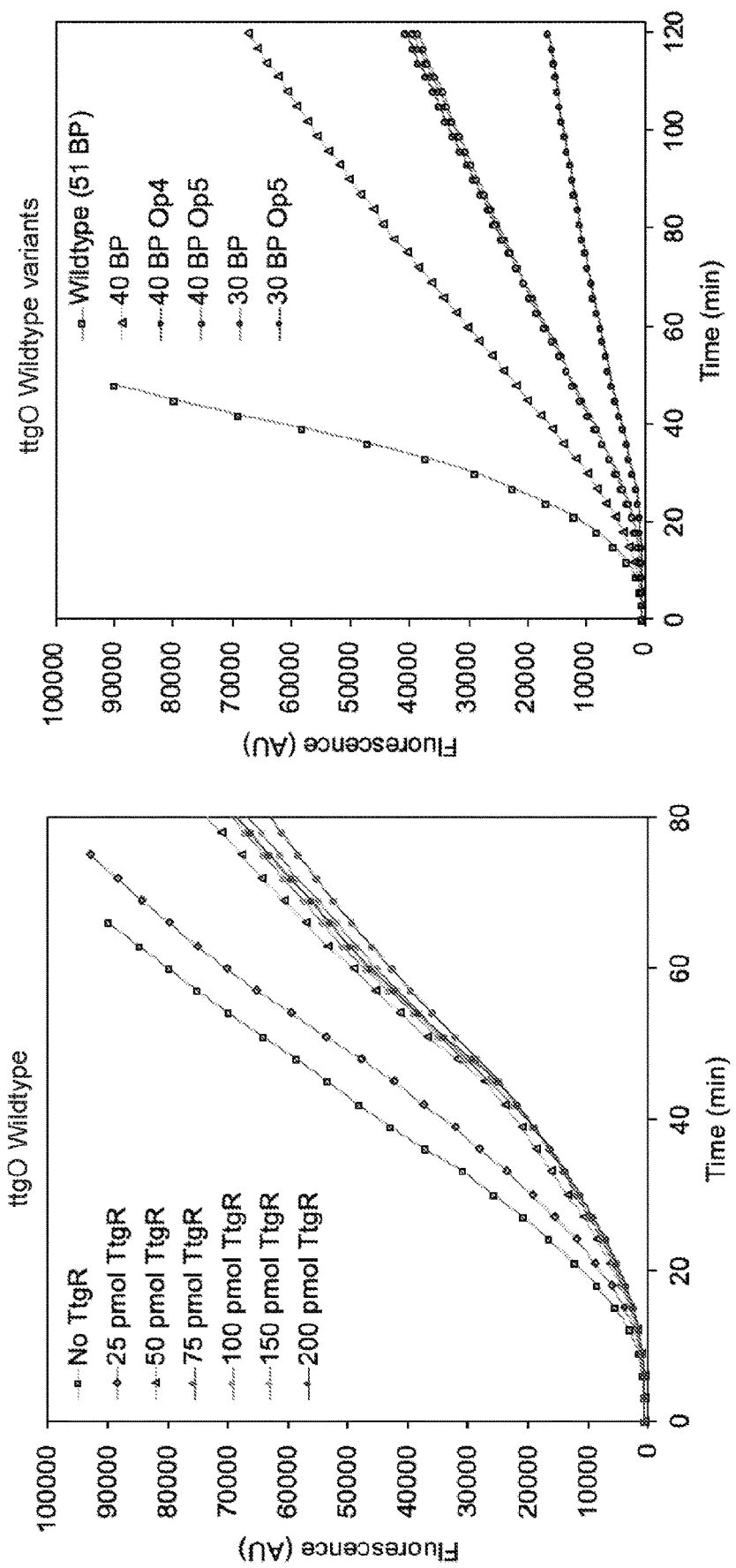
FIG. 12. Demonstration that operator sequences engineered for length and sequence can be used to increase the repression efficiency of an allosteric transcription factor.
Figure 12:
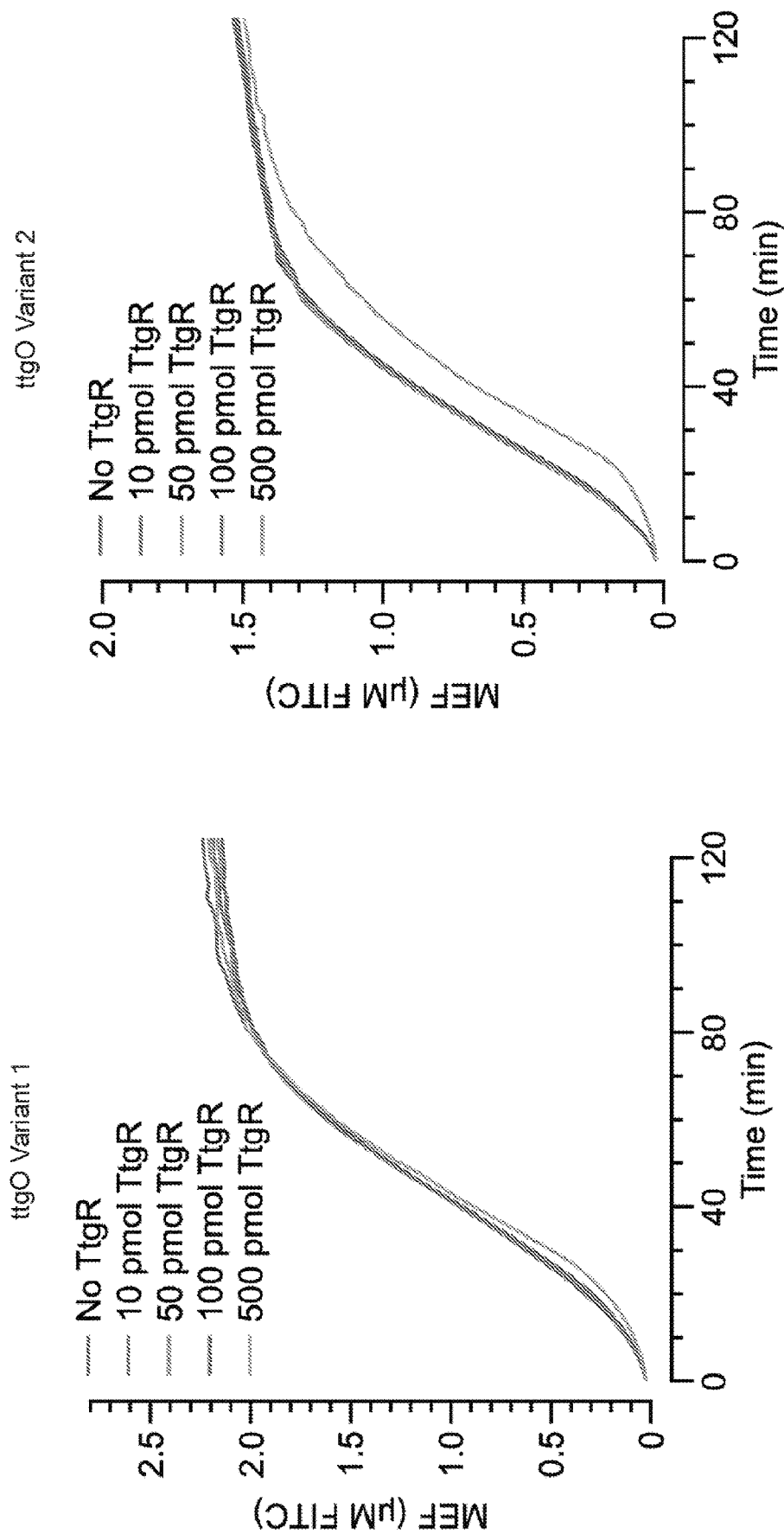
Figure 12:
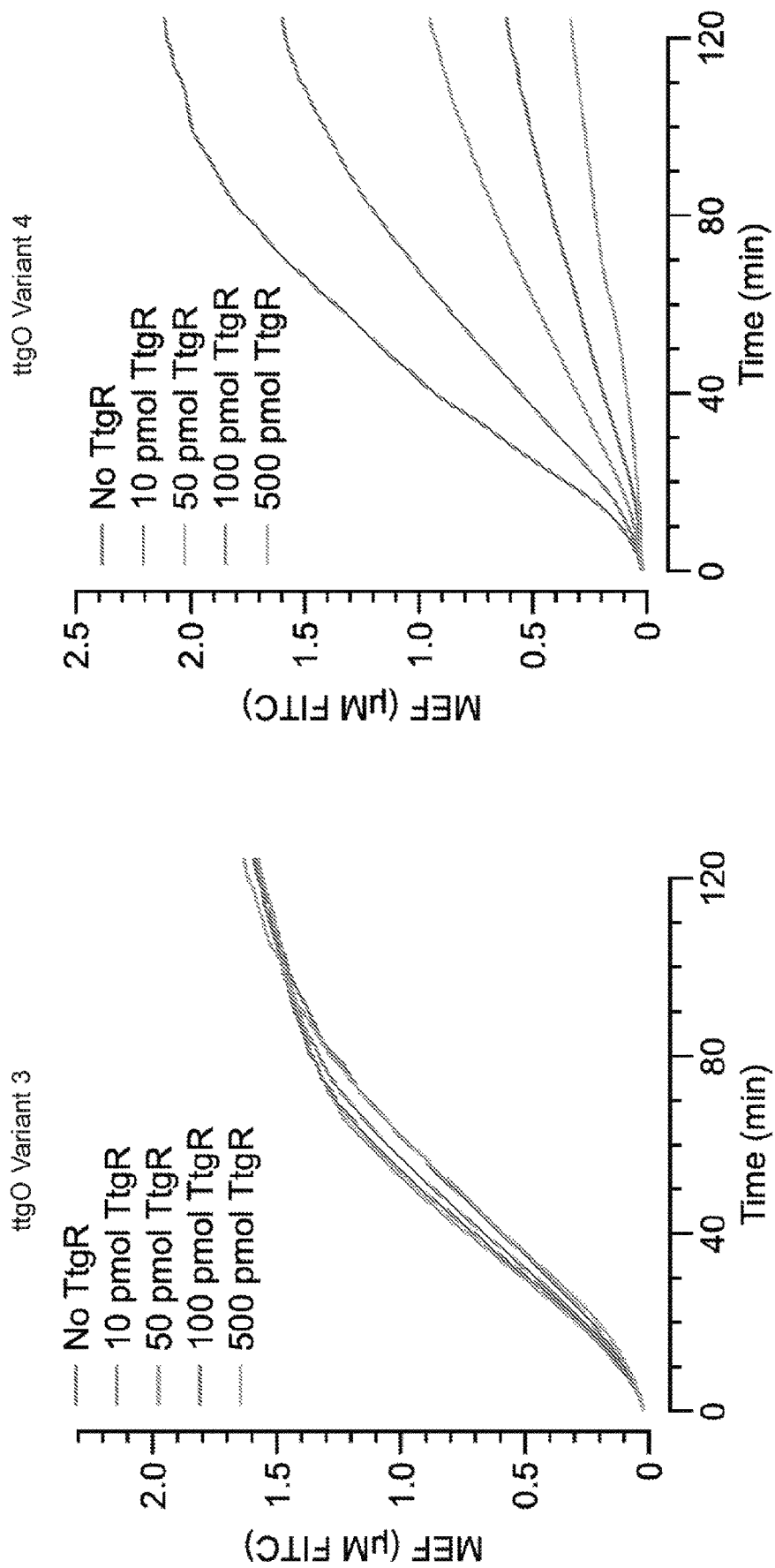

FIG. 12 illustrates that further engineering of the DNA transcription template can improve RIViTS performance. We identified the allosteric transcription factor TtgR, which can be induced in the presence of the plant metabolite naringenin. The corresponding operator sequence (ttgO) we identified was a 51 basepair sequence that we were unable to strongly repress with the addition of TtgR. We therefore generated several operator variants that minimized the length of the operator (40 BP and 30 BP) to prevent the transition of T7 RNAP from initiation to elongation mode, as well as variants designed to optimize the palindromic order of the operator sequence (Op4 and Op5). We found that both minimizing the operator sequence and optimizing towards a perfect palindrome resulted in sufficiently robust repression in the presence of TtgR.

Figure 13:
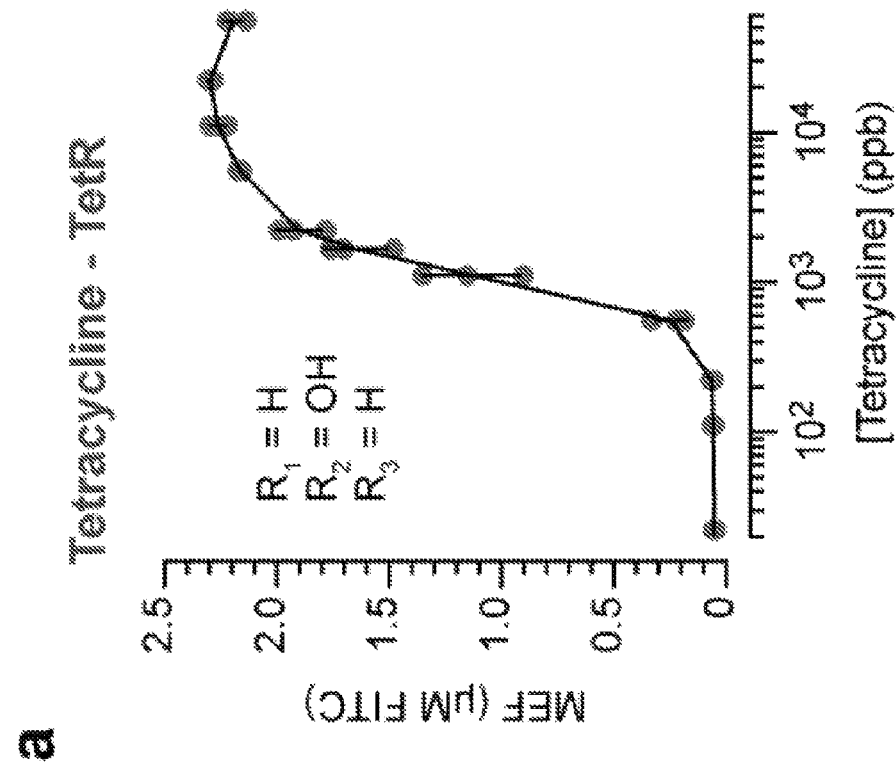
FIG. 13. Demonstration that in vitro transcriptions of fluorescence-activating aptamer (3WJdB) can be regulated with a variety of tetracycline-responsive and macrolide-responsive transcription factors and their cognate ligands. Each transcription reaction contains 0.5 pmol of transcription template. TetR regulated reactions contain 50 pmol of TetR. OtrR regulated reactions contain 100 pmol of OtrR. CtcS regulated reactions contain 50 pmol of CtcS. MphR regulated reactions contain 25 pmol of MphR.
Figure 13:
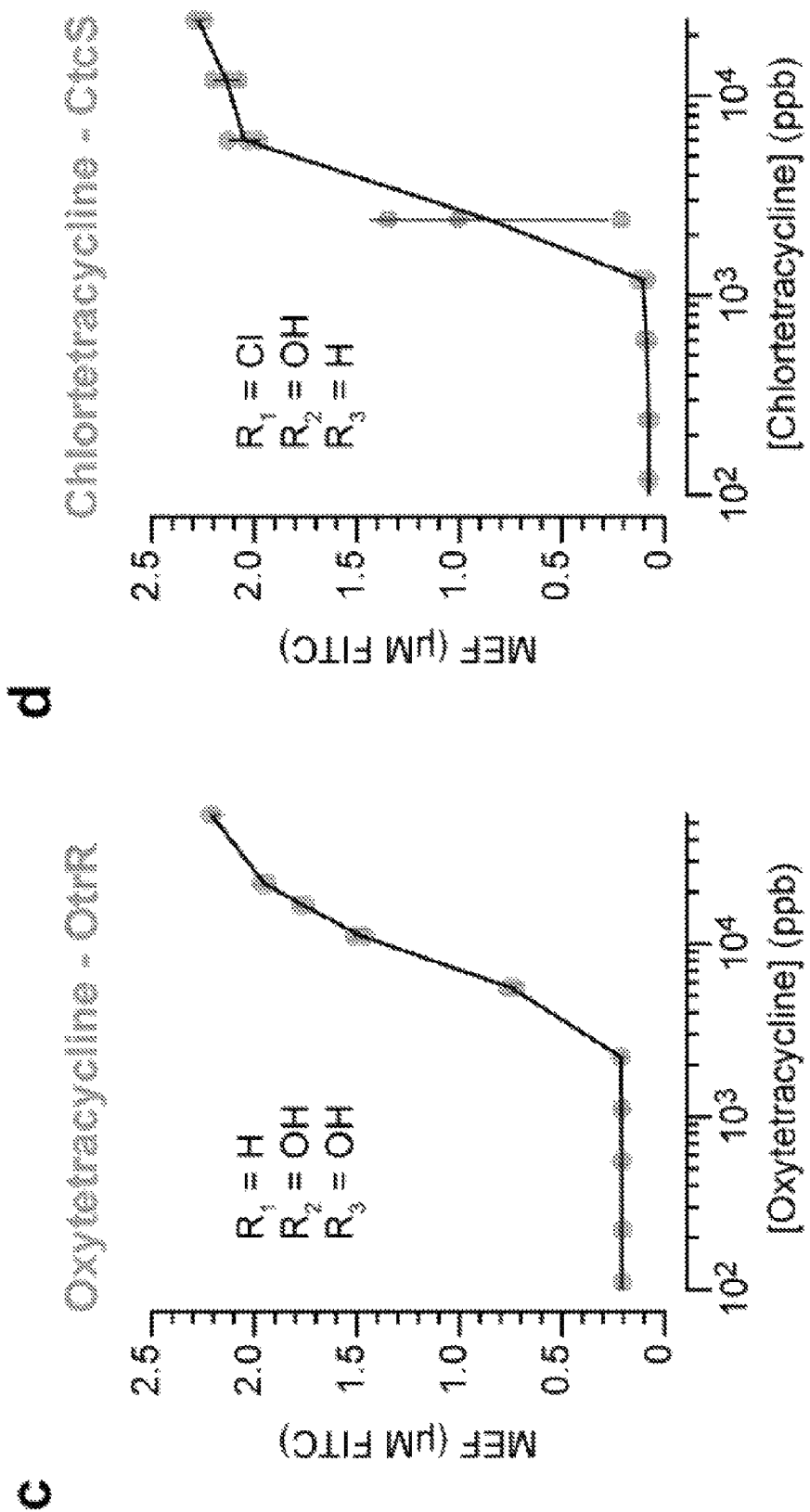
Figure 13:
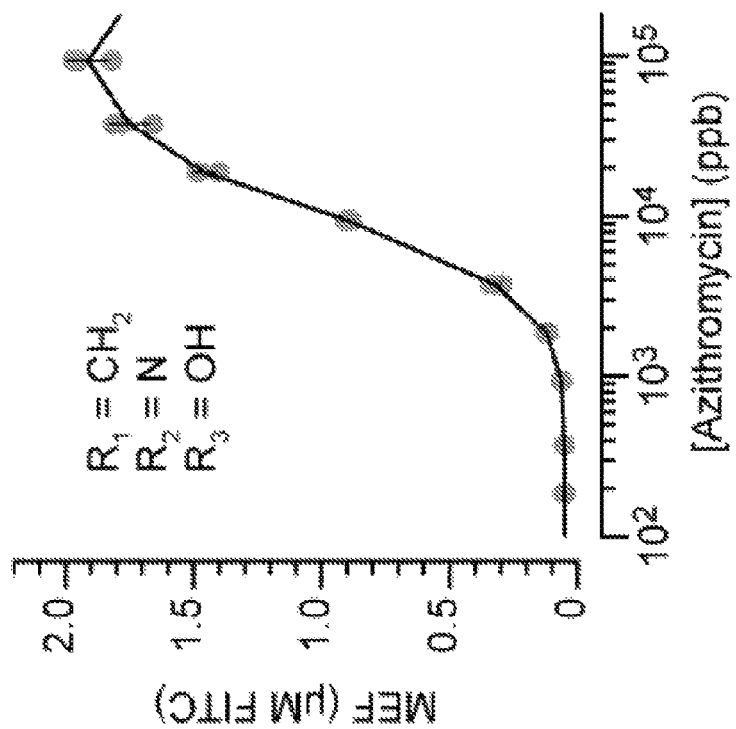
Figure 13:
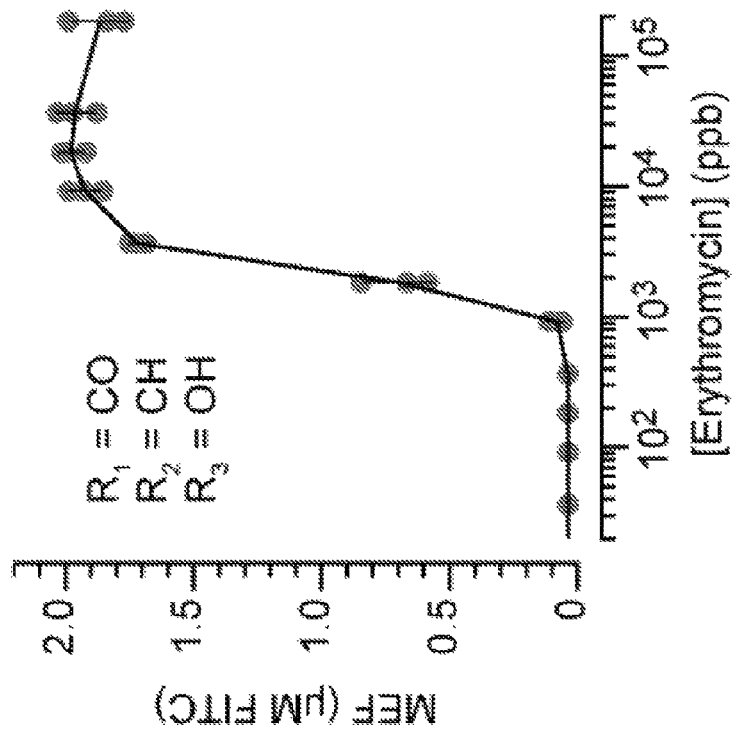
Figure 13:
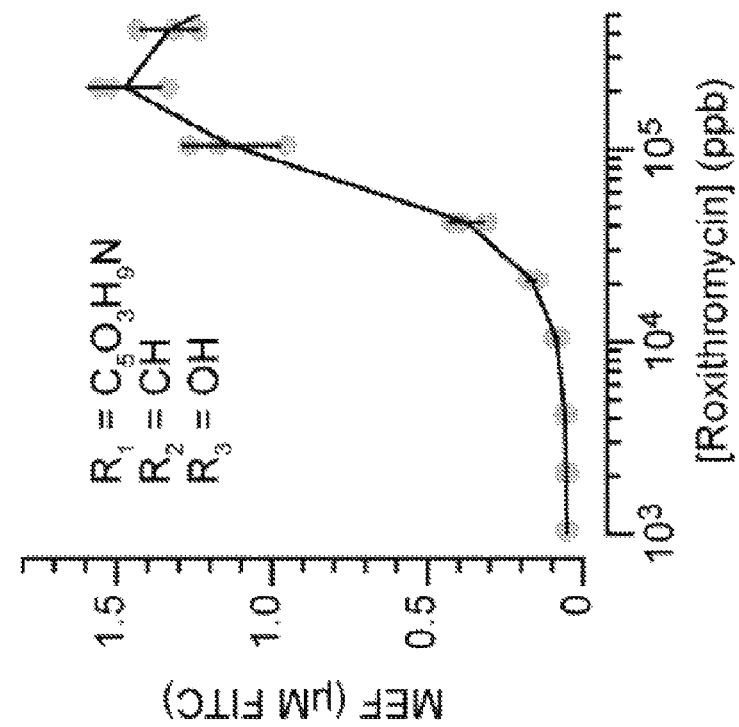
Figure 13:
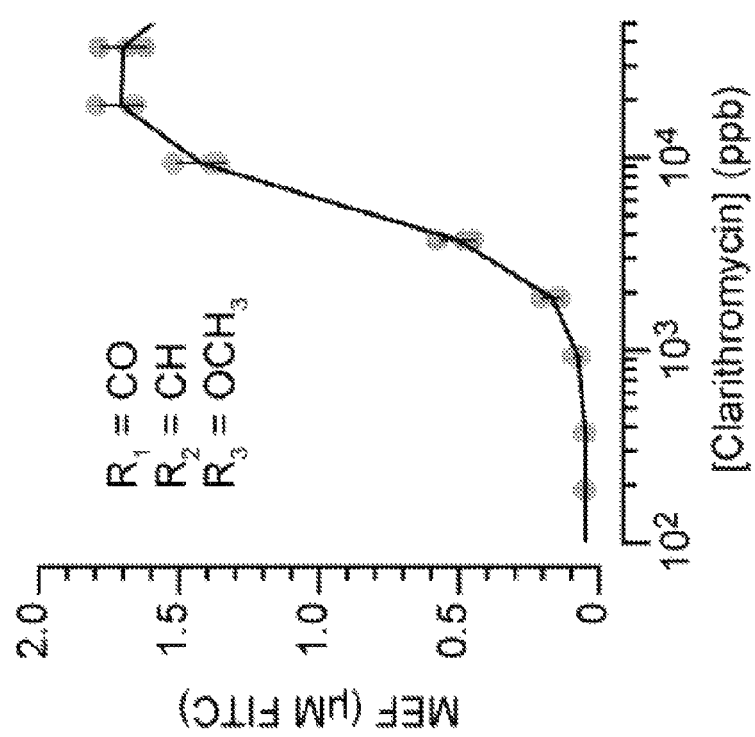
Figure 14:
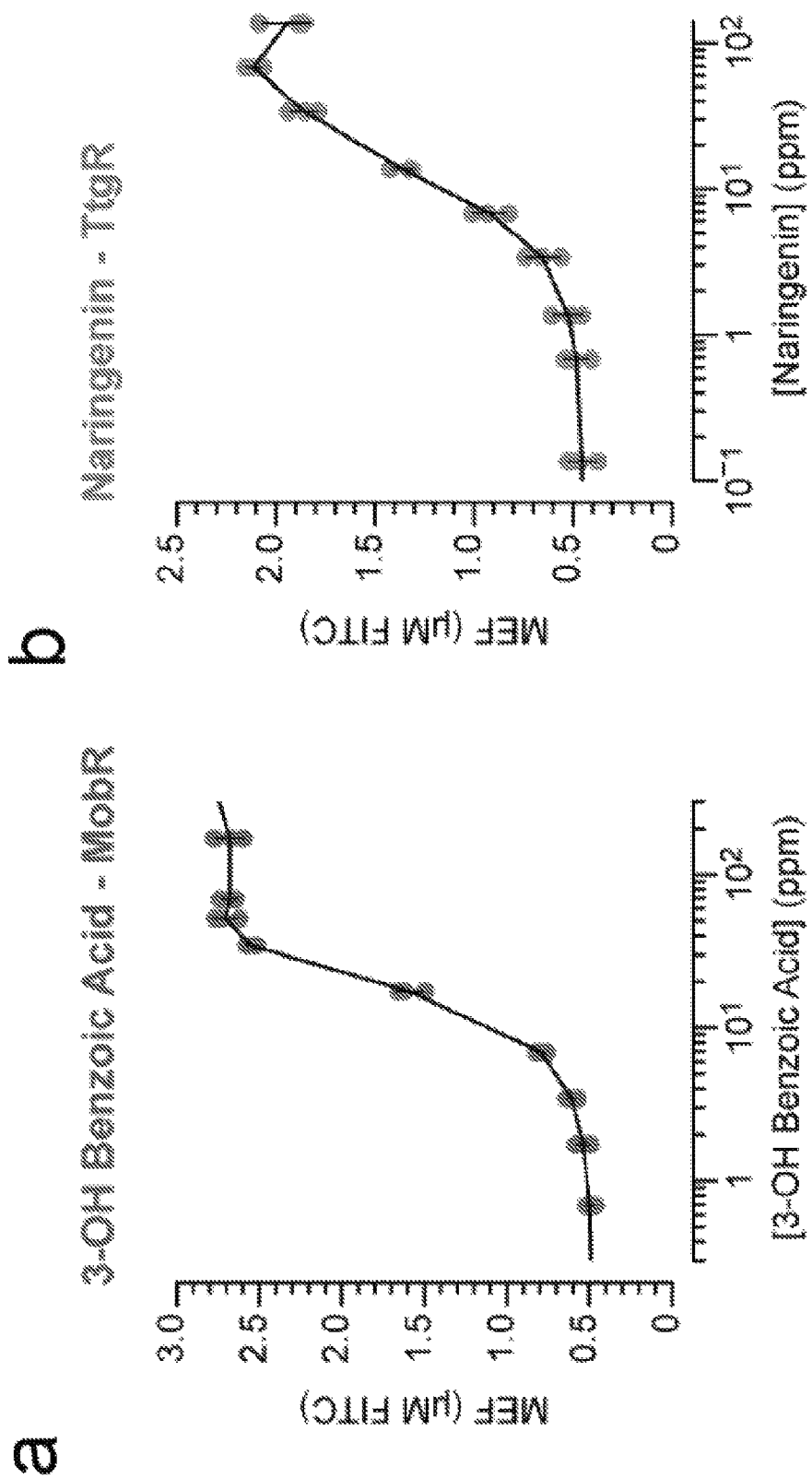
FIG. 14. Demonstration that in vitro transcriptions of fluorescence-activating aptamer (3WJdB) can be regulated with a variety of small molecule and metal ion transcription factors and their cognate ligands. Each reaction has 0.2 pmol of transcription template in panel a, b, and e, 0.25 pmol of transcription template in panel c and d, and 0.5 pmol of transcription template in panel f-i. The concentrations of transcription factors in each panel are 4000 pmol of MobR, 500 pmol of TtgR, 100 pmol of QacR, 50 pmol of HucR, 1000 pmol of SAR2349 200 pmol of SmtB, 200 pmol of CsoR, and 60 pmol of CadC.
Figure 14:
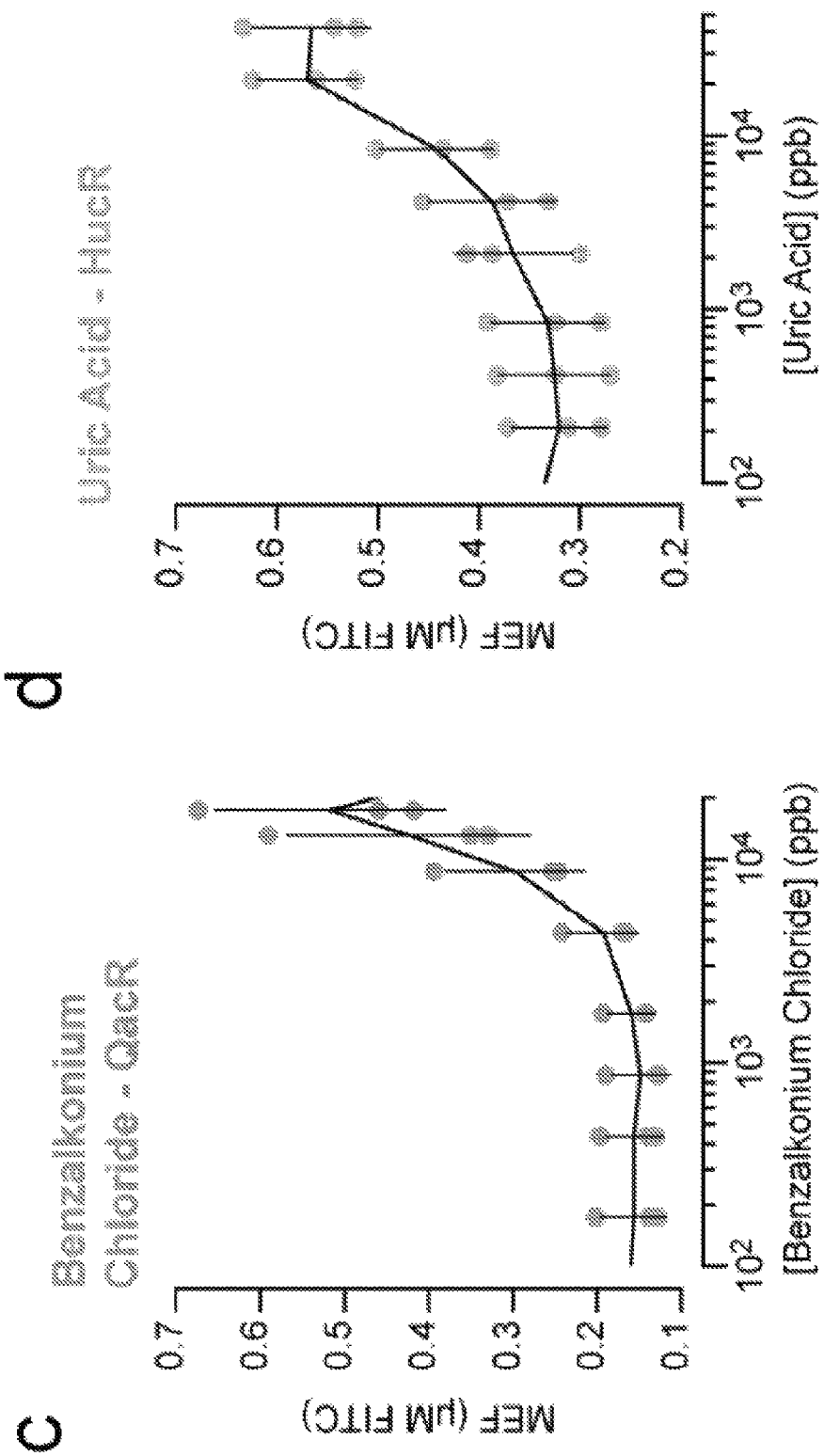
Figure 14:
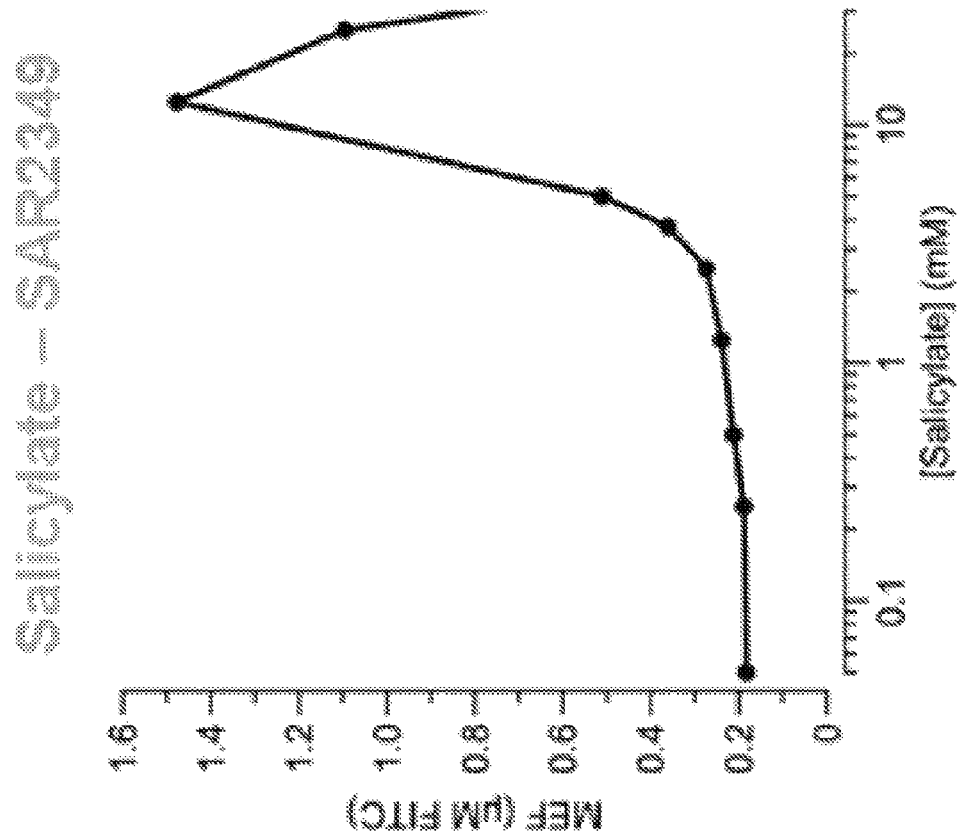
Figure 14:
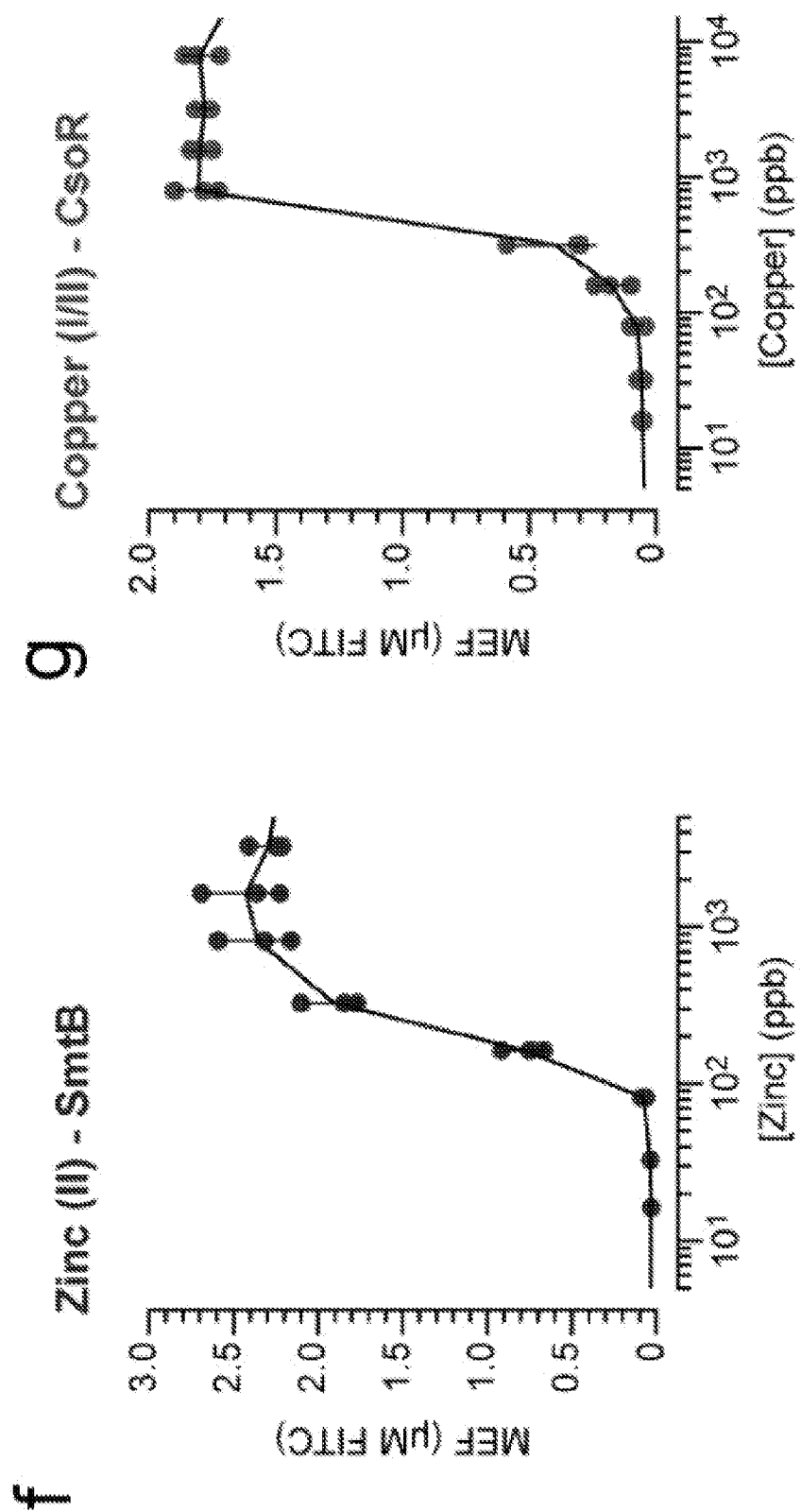
Figure 14:
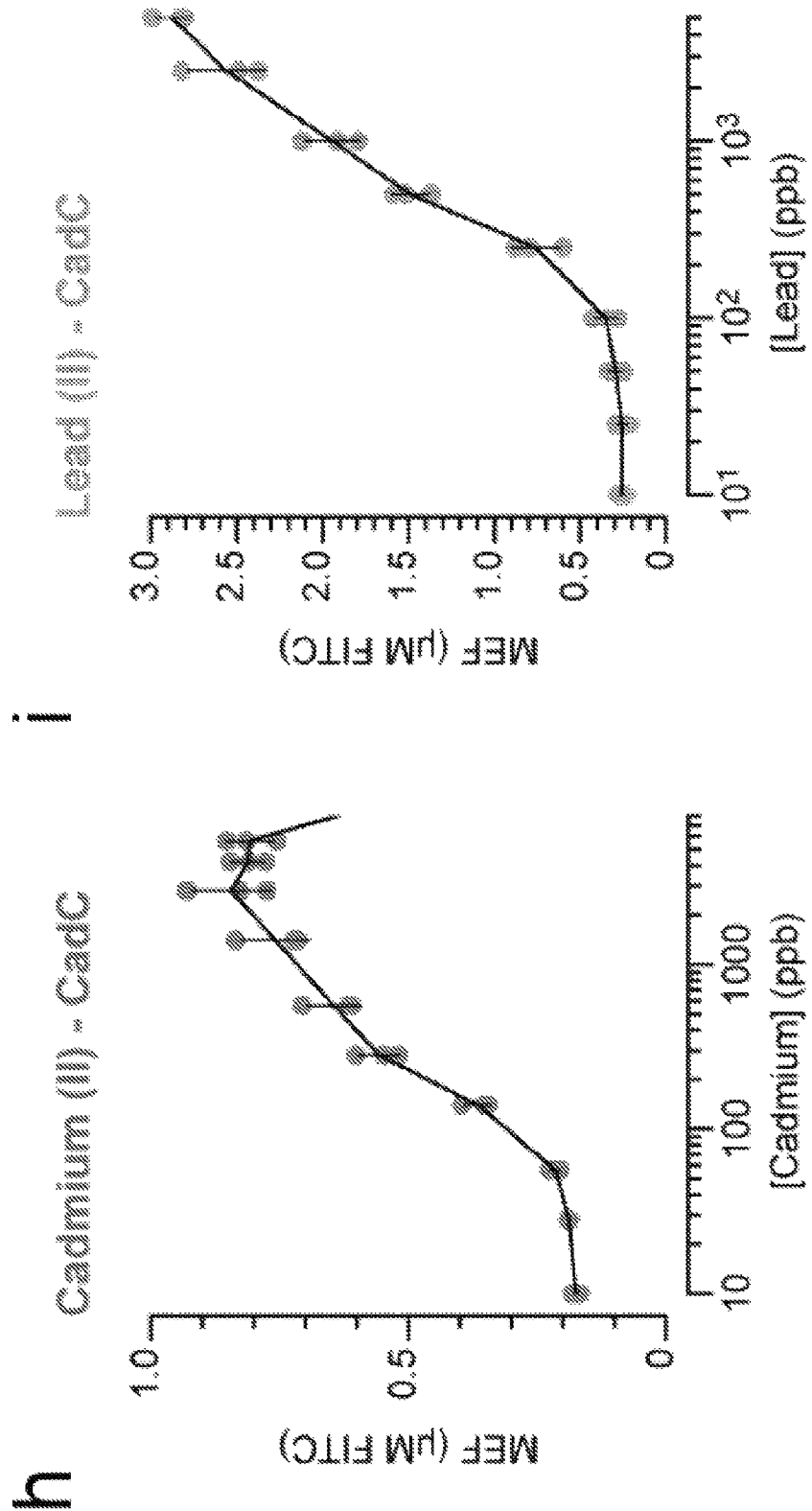

FIGS. 13 and 14 illustrate that the RIViTS platform responds to a range of ligand concentrations. Different RIViTS reactions were assembled using different combinations of ATFs and their corresponding engineered transcription templates that encoded 3WJdB reporters. Each reaction was then subjected to a range of concentrations of the cognate ligands of each ATF including antibiotics (FIG. 13) and small molecules and metal ions (FIG. 14). In all cases we observed an increase in signal upon increasing ligand concentration until a saturation point was achieved. In many cases we observed a sharp transition in these dose-response-curves indicating that RIViTS could be used, though not exclusively, to identify ligand concentrations above some defined threshold value.

We also confirmed that RIViTS reactions configured to use DNA strand displacement as an output were able to be activated in the presence of a range of ligands. (See FIG. 15). Different RIViTS reactions were assembled using different combinations of ATFs and their corresponding engineered transcription templates that generated InvadeR sequences that activated included quenched and fluorescently labeled double stranded DNA. Three different ATFs were used (TetR, SmtB, MarR) and each reaction was subjected to the cognate ligand or a no ligand control. In all cases we observed activation of signal only in the presence of the cognate ligand (FIG. 15).

Figure 16:
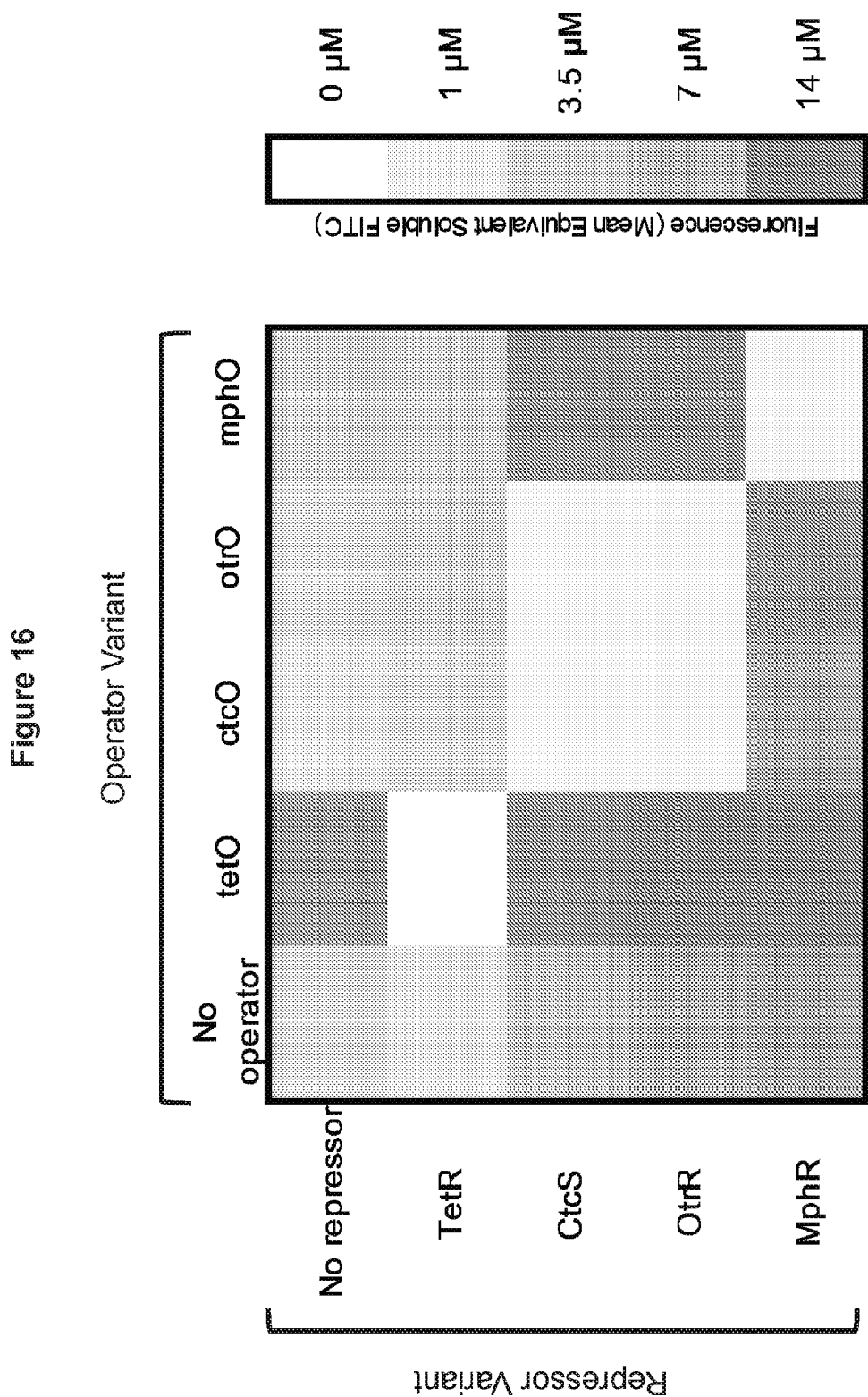
FIG. 16. Demonstration that regulated in vitro transcription is orthogonal with respect to repressors. Each transcription reaction contains 1 pmol of transcription template and 100 pmol of repressor (except for "No repressor" samples). Data was generated after two hours at 37° C.

RIViTS are orthogonal with respect to ATF and ligand. The potential for biosensing using regulated in vitro transcription reactions can be improved by utilizing genetic circuitry to further process information from different analyte inputs. We tested the orthogonality (lack of cross-regulation between ATFs and operator sites) of the TetR, MphR, OtrR and CtcS ATFs with templates containing their respective operator sites (FIG. 16). In the absence of an operator sequence in the template, transcription of 3WJdB was productive regardless of which ATF was added to the reaction and may have even improved signal generation relative to the "no operator" and "no repressor control" through molecular crowding effects. Both TetR-family ATFs (TetR and MphR) were orthogonal with each other (no cross repression) and with the transcription templates specific to other ATFs. Although CtcS and OtrR exhibited significant cross-repression with each other, this was expected as they are homologous repressors that control the biosynthesis of compounds that differ by a single functional group.

Figure 17:
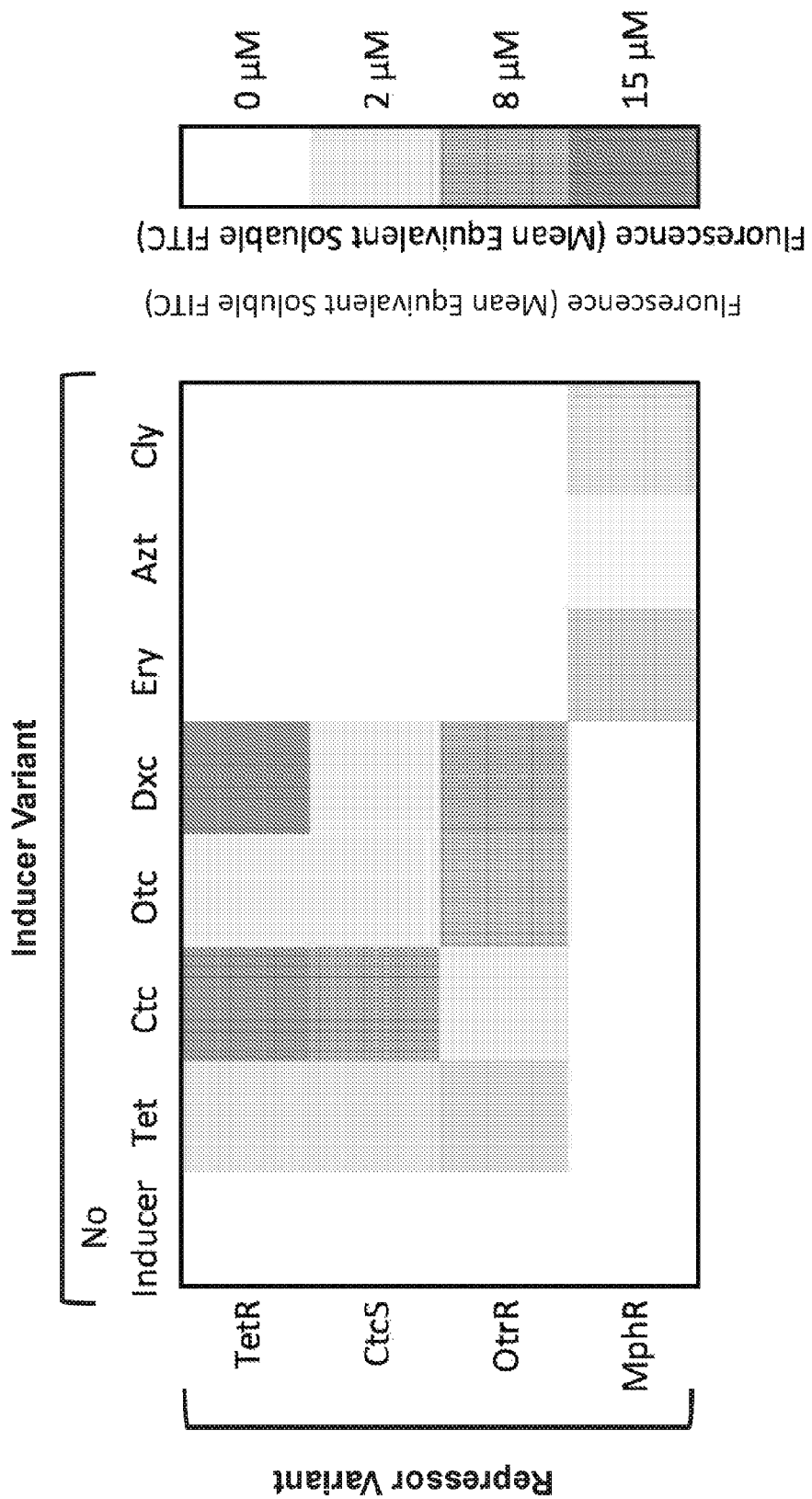
FIG. 17. Demonstration that regulated in vitro transcription is orthogonal with respect to inducers. Each transcription reaction contains 1 pmol of transcription template, 200 pmol of repressor, and 1 nmol of inducer (except for "No Inducer" samples). Data was generated after two hours at 37° C.

Similarly, we tested the orthogonality of the TetR, OtrR, CtcS, and MphR with their respective ligands (FIG. 17). In the absence of the ligands or inducers, there was a strong repression of transcription by the ATFs as expected. Only the tetracycline antibiotics tested were able to cause an allosteric conformational change in TetR, OtrR, and CtcS and restore fluorescence signal equivalent to micromolar amounts of soluble FITC, confirming the results presented in FIG. 10A. Similarly, MphR was responsive to macrolide antibiotics, but not to any tetracycline antibiotics tested.

These results demonstrate that within the RIViTS system, ATFs and their respective ligands remain the same specificity relationships.

Figure 18:
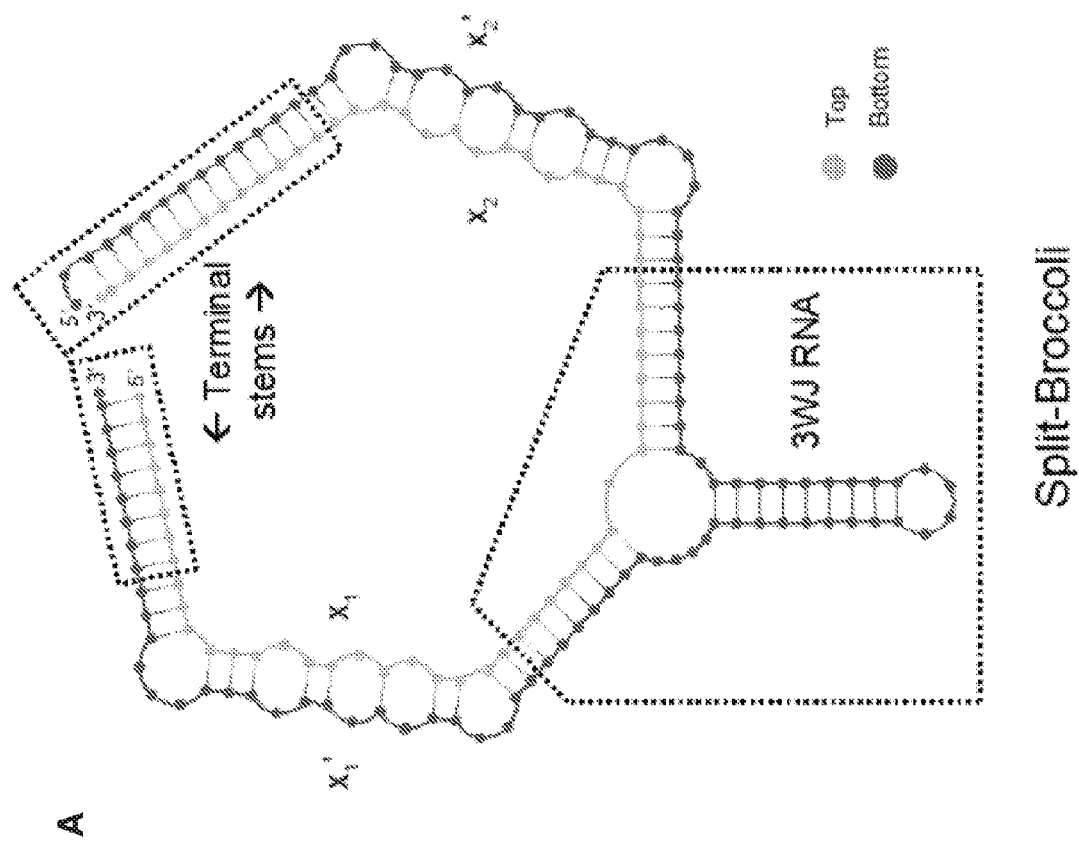
FIG. 18. Demonstration that regulated in vitro transcriptions can be used to perform logical operations. Using two different allosteric transcription factors to control the synthesis of two different halves of the 3WJdB reporter molecule only allows a detectable signal in the presence of both cognate ligands (an AND gate).

RIViTS can perform logical operations. Given that regulated in vitro transcriptions can be orthogonal with respect to both ATFs and ligands, we reasoned that an orthogonal pairing (e.g. TetR/tetO with MphR/mphO) could be combined into a single in vitro transcription reaction to perform a logical operation. We illustrate this point with the Split-Broccoli fluorescence-activating aptamer system.[19] Split-Broccoli is a two-stranded variant of the 3WJdB aptamer and requires that two separately synthesized strands ("Top" and "Bottom") assemble together to activate fluorescence (FIG. 18A). When Top and Bottom are independently regulated by TetR/tetO and MphR/mphO respectively, then fluorescence-activation by Split-Broccoli is only possible if both ligands (e.g. tetracycline and erythromycin) are present at concentrations sufficient to derepress transcription. In the absence of one or both ligands, transcription of Top and Bottom is repressed, resulting in no Split-Broccoli fluorescence activation. This function is known as an "AND" logic gate (FIG. 18B) and is further diagrammed in FIG. 18C. A truth table, representing the Boolean values of each input and the output, is shown in FIG. 18D. Logic gates are an important component of biosensors as they allow the conditional production of output signals as a function of specific input molecule concentrations. In this way they can be used to test for combinations of input compounds, rather than just single compounds.

Figure 19:
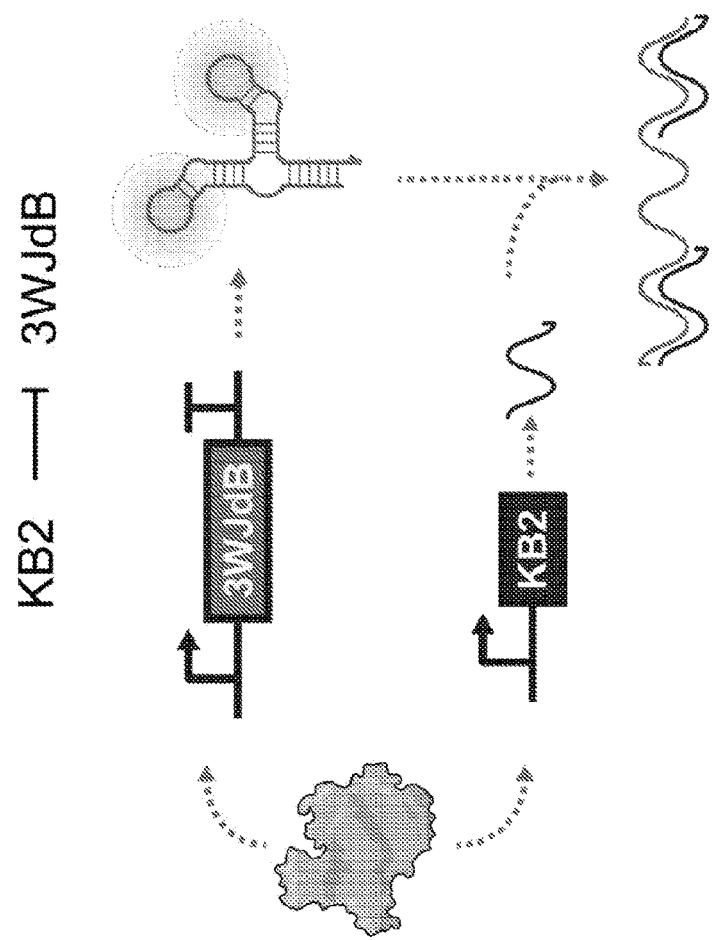
FIG. 19. Demonstration that fluorescence activation of 3WJdB can be repressed by a kleptamer ("KB2"). Each transcription reaction contains 0.5 pmol of 3WJdB transcription template.
Figure 19:
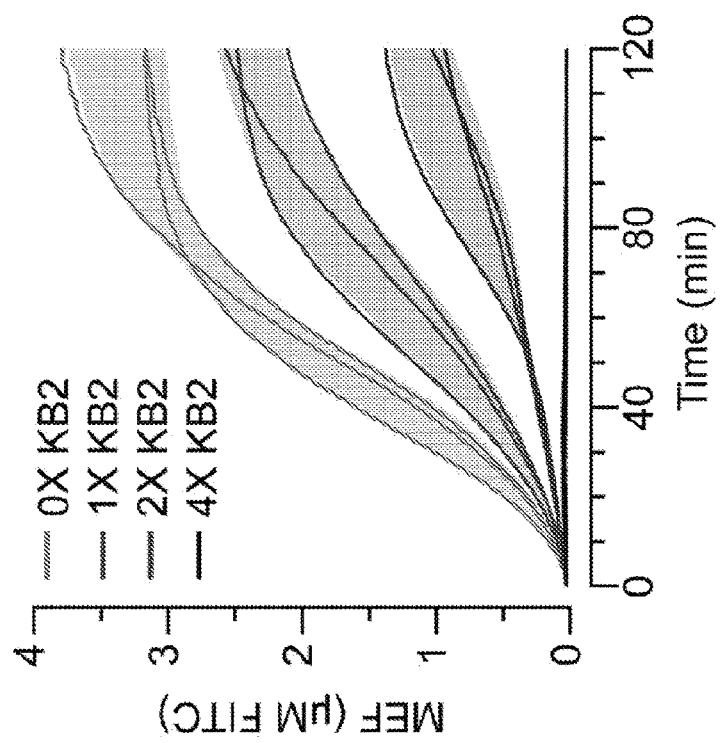

ATF ligand-mediated transcriptional activation can be inverted to ligand-mediated repression with RNA genetic circuitry. All of the previous results showed that ATFs can be used to activate transcriptional outputs in response to ligand binding, through derepression of the operator binding site. We next sought to see if we could invert this into ligand-mediated repression to give further flexibility in designing biosensors. To achieve this goal, we implemented the KB2 "kleptamer"—a simple antisense RNA molecule that is complementary to the broccoli aptamer.[35] This molecule can displace the aptamer from the dye by preventing the aptamer from folding into a conformation needed to bind the dye and thereby switch off the fluorescence signal. We reasoned that by regulating the transcription of the KB2 kleptamer with the ATF, we can easily turn on or off the fluorescence signal from the 3WJdB aptamer. To test this hypothesis, we first examined whether we could effectively repress the fluorescence-activation of the 3WJdB aptamer by transcribing the KB2 kleptamer with T7 RNA polymerase. As expected, titration of increasing amounts of the KB2 kleptamer resulted in increased repression of fluorescence-activation (FIG. 19). At an 8:1 ratio of kleptamer over 3WJdB transcription templates, signal generation is effectively off for 1.5 hours.

Figure 20:
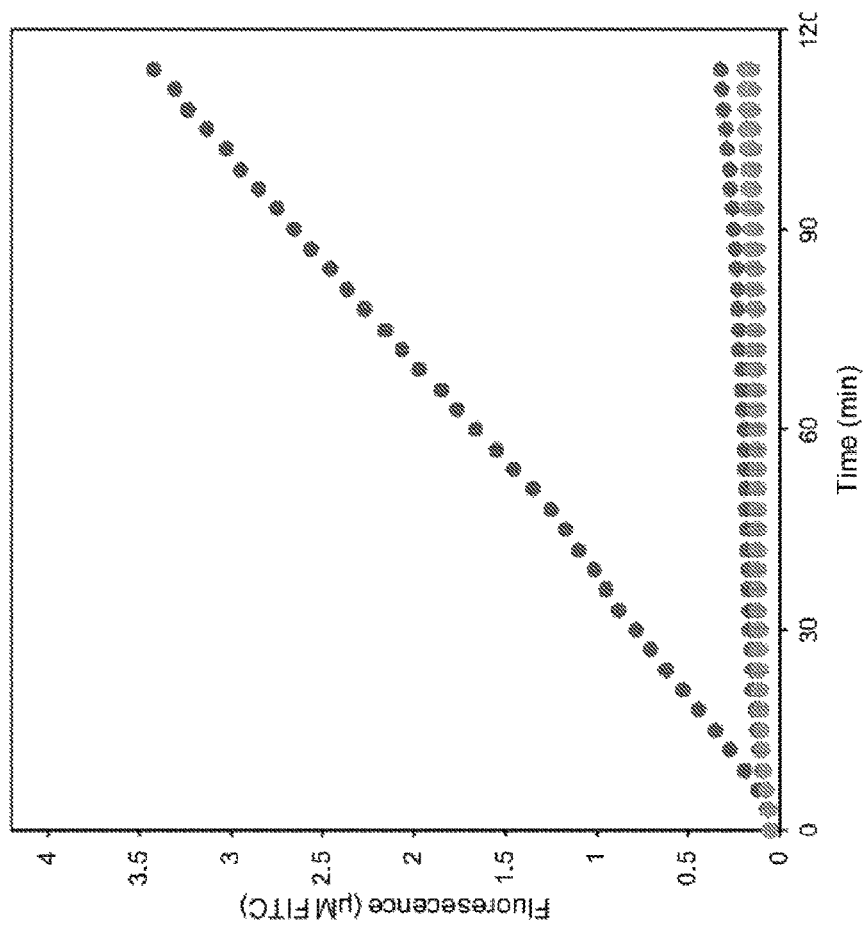
FIG. 20. Demonstration that kleptamer transcription is compatible with transcription of an operator. Each transcription reaction contains 0.5 pmol of a 3WJdB transcription template.
Figure 20:
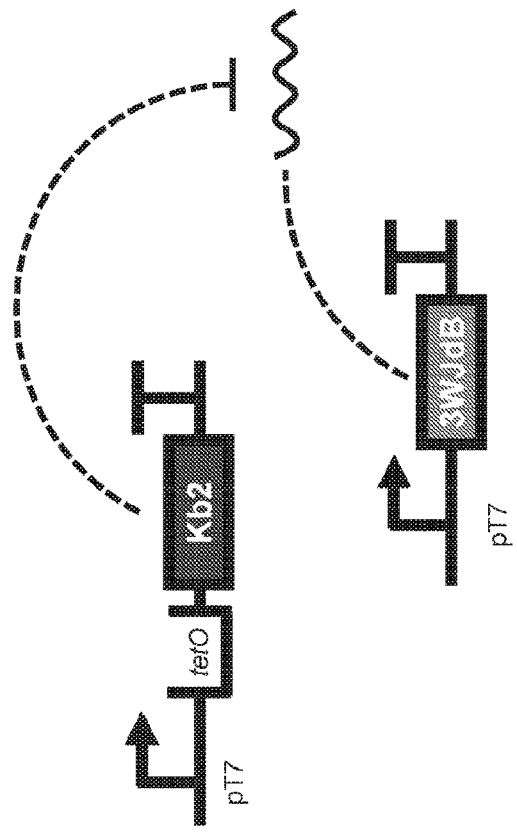

Next, we sought to see if we can regulate the transcription of the KB2 kleptamer by including an operator site recognized by ATFs upstream of the KB2 kleptamer sequence. Including an additional operator sequence upstream of the kleptamer that would be transcribed by a regulated template did not interfere with kleptamer activity (FIG. 20).

Figure 21:
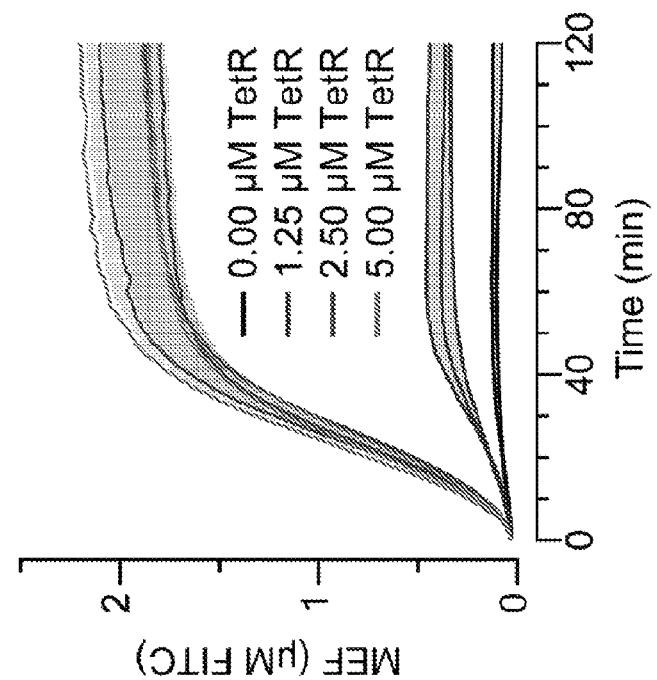
FIG. 21. Demonstration that transcription of a kleptamer repressed by TetR allows us to invert regulator response. Each transcription reaction contains 0.5 pmol of a 3WJdB transcription template and 3 pmol of tetO KB2 transcription template.
Figure 21:
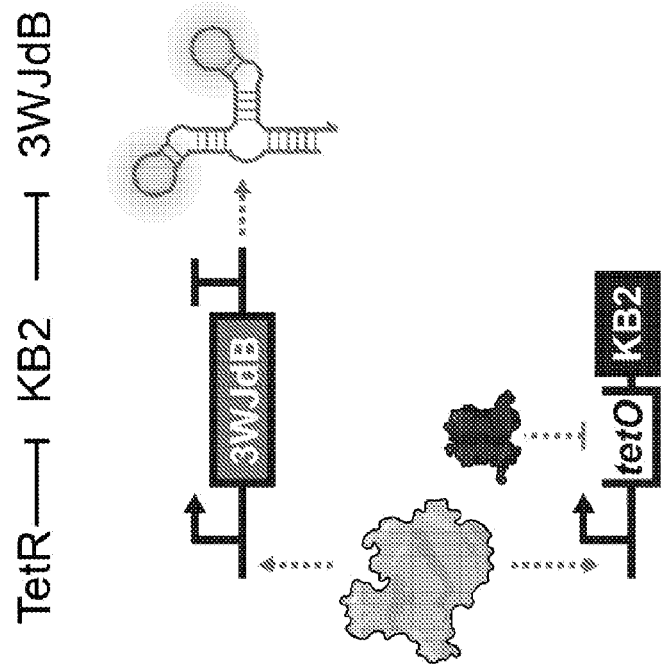
Figure 22:
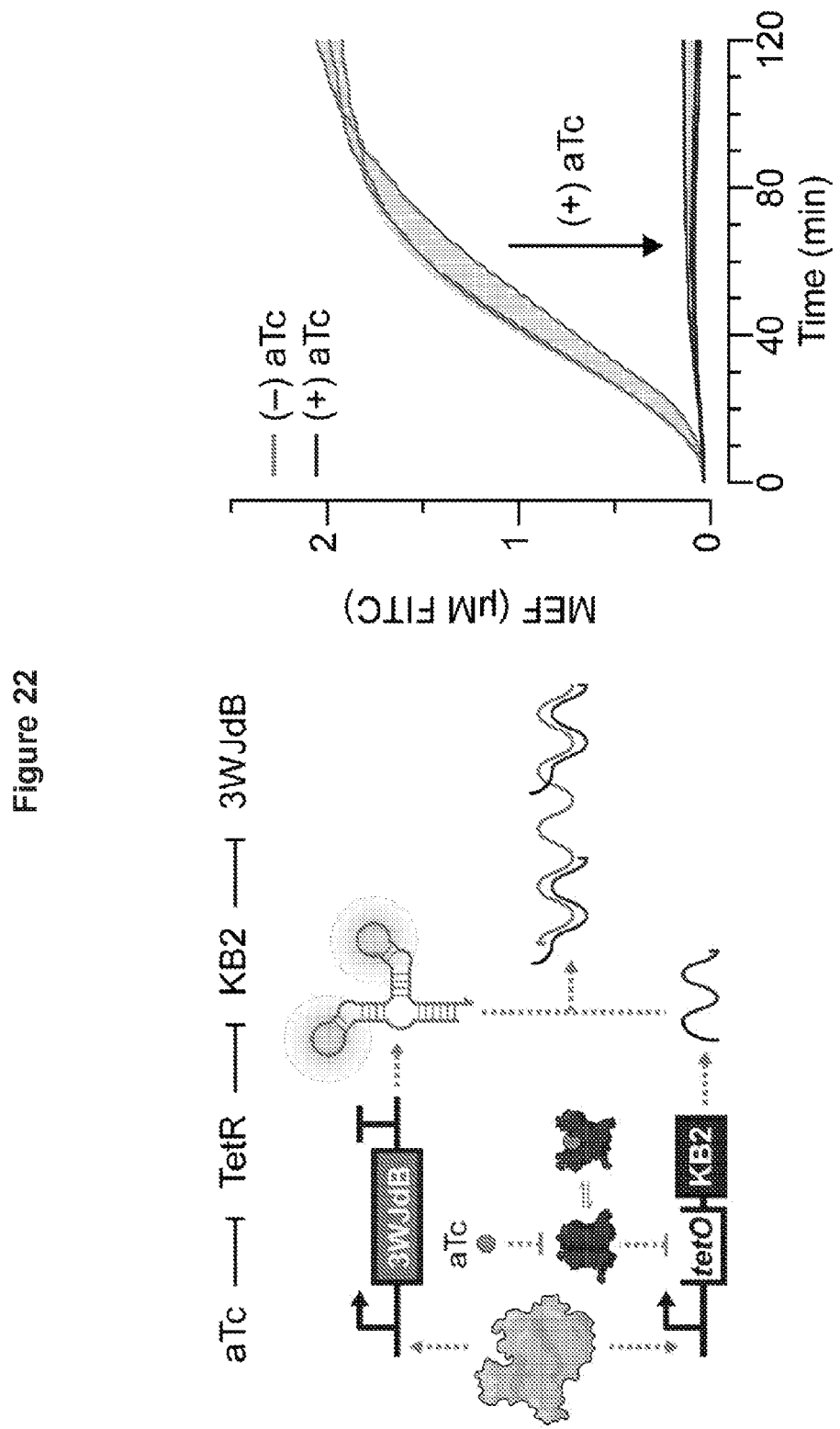
FIG. 22. Demonstration that transcription of a kleptamer induced by a ligand allows us to invert regulator response. Each transcription reaction contains 0.5 pmol of 3WJdB transcription template, 3 pmol of tetO KB2 transcription template, and 50 pmol of TetR. (+) aTc condition has 50 pmol of aTc.

When we placed the tetO sequence upstream of the KB2 kleptamer and titrated increasing amounts of TetR, fluorescence-activation was restored, confirming the inversion of TetR repression into activation (FIG. 21). Adding tetracycline to the reaction conditions caused a decreased fluorescence-activation as expected from this inversion (FIG. 22).

These results demonstrate that RNA genetic circuits can be used to invert ATF functional responses.

Figure 23:
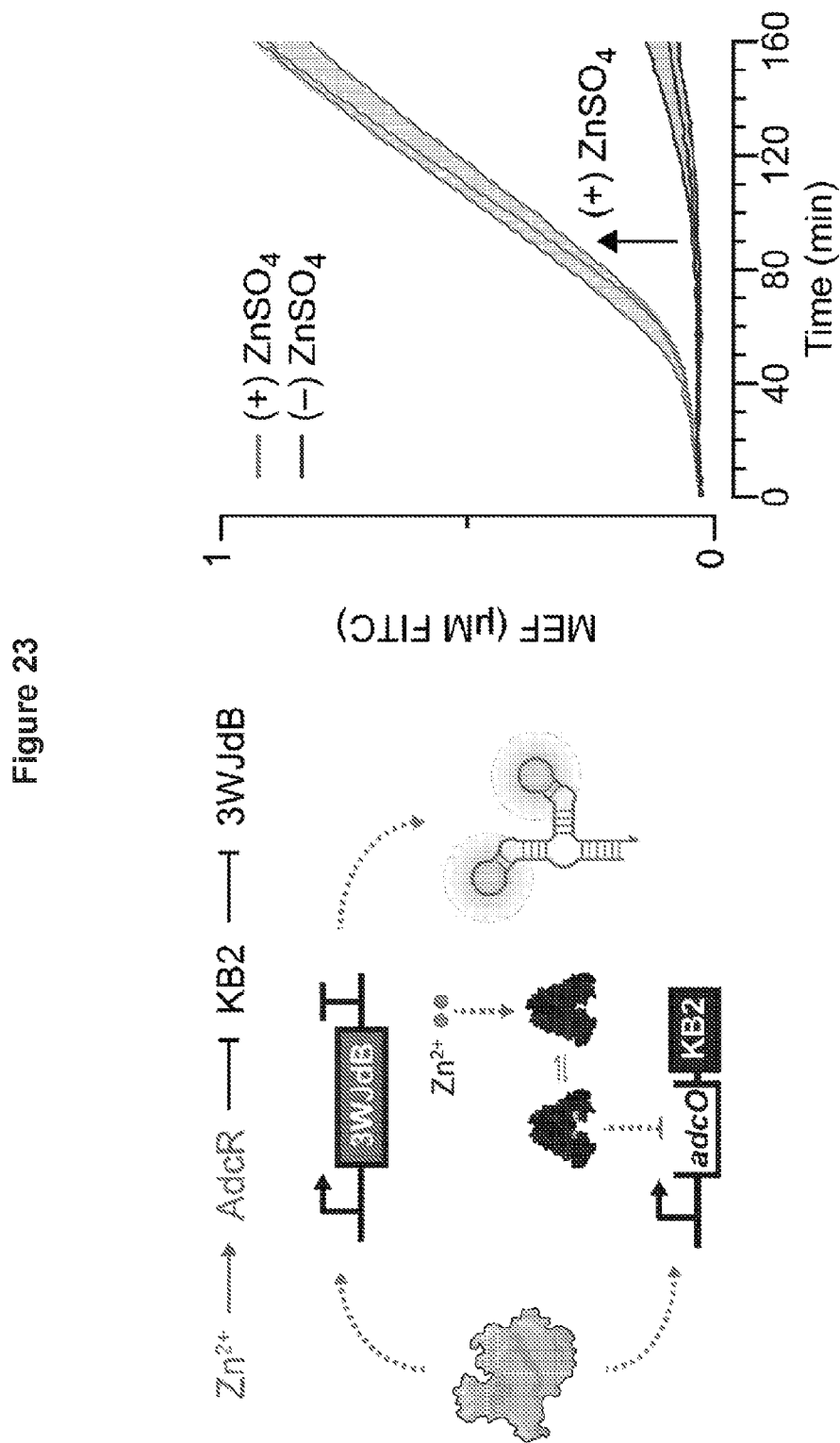
FIG. 23. Demonstration that ATF ligand-induced repression can be inverted to ligand-mediated activation with a kleptamer. Each transcription reaction contains 0.5 pmol of the 3WJdB template. 3 pmol of the adcO KB2 template, and 60 pmol of AdcR. (+) zinc sulfate condition has 600 pmol of zinc sulfate.

ATF ligand-mediated transcriptional repression can be inverted to ligand-mediated activation with RNA genetic circuitry. We next tested the kleptamer system with an ATF that is known to bind to its operator site in the presence of its cognate ligand and therefore cause ligand-mediated repression. AdcR is a MarR-family ATF and known to regulate genes encoding a high-affinity ABC uptake system for zinc and cell-surface zinc-binding pneumococcal histidine triad proteins.[36] Unlike the ATFs we tested previously, apo-AdcR is unbound to its operator site. Upon binding Zn(II), AdcR undergoes a conformational change that results in binding to the operator site. We placed an operator site recognized by AdcR (adcO) upstream of the KB2 kleptamer so that when zinc is present, the transcription of the KB2 kleptamer is repressed by the AdcR-zinc complex and the fluorescence-activating 3WJdB aptamer is produced. Titration of increasing amounts of Zn(II) in the presence of the unregulated 3WJdB template and the adcO regulated KB2 kleptamer template resulted in increased fluorescence-activation (FIG. 23).

These results further demonstrate that RNA genetic circuits can be used to invert ATF functional responses during in vitro transcription.

Figure 24:
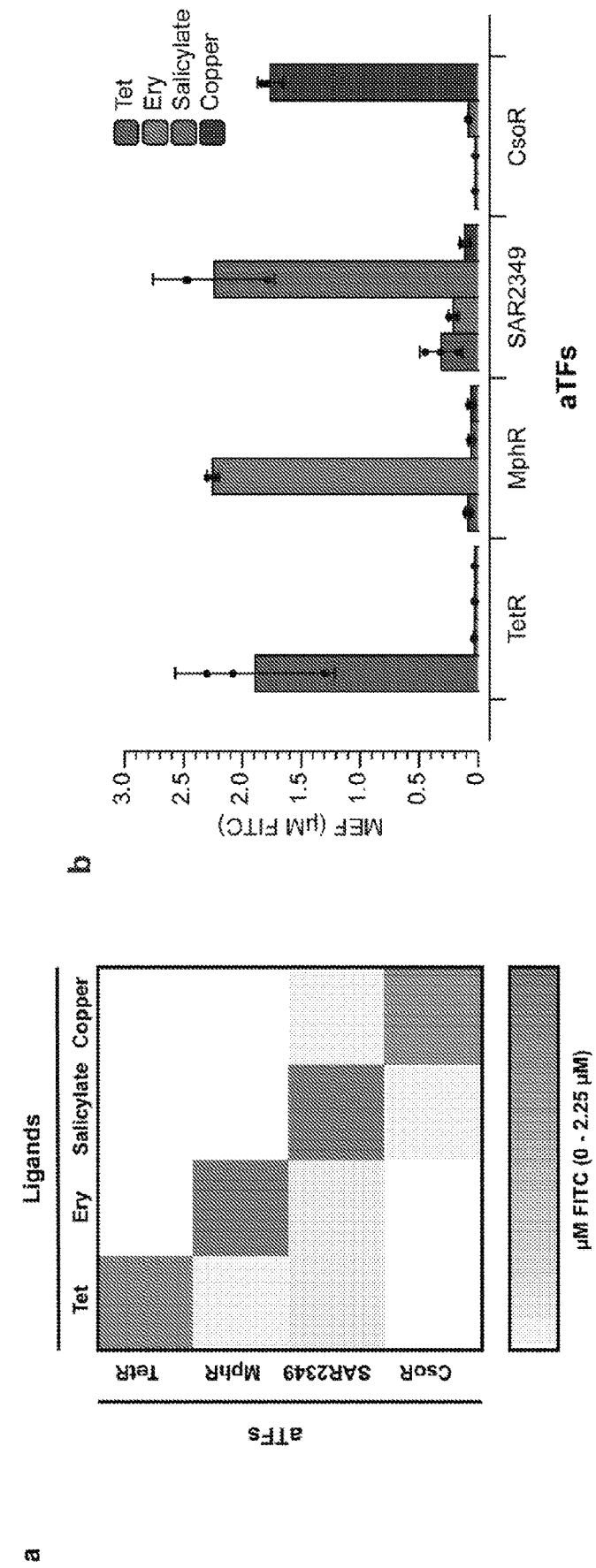
FIG. 24. Demonstration that a RIViTS reaction is orthogonal across different families of ligands. Each reaction includes 0.5 pmol of 3WJdB transcription templates except for the SAR2349-regulated reactions, which have 0.35 pmol of template each. TetR-regulated reactions have 50 pmol of TetR, MphR-regulated reactions have 25 pmol of MphR, SAR2349-regulated reactions have 2000 pmol of SAR2349, and CsoR-regulated reactions have 200 pmol of CsoR. Concentrations of ligands tested are 500 pmol of tetracycline, 1000 pmol of erythromycin, 240 nmol of salicylate, and 200 pmol of copper sulfate.
Figure 25:
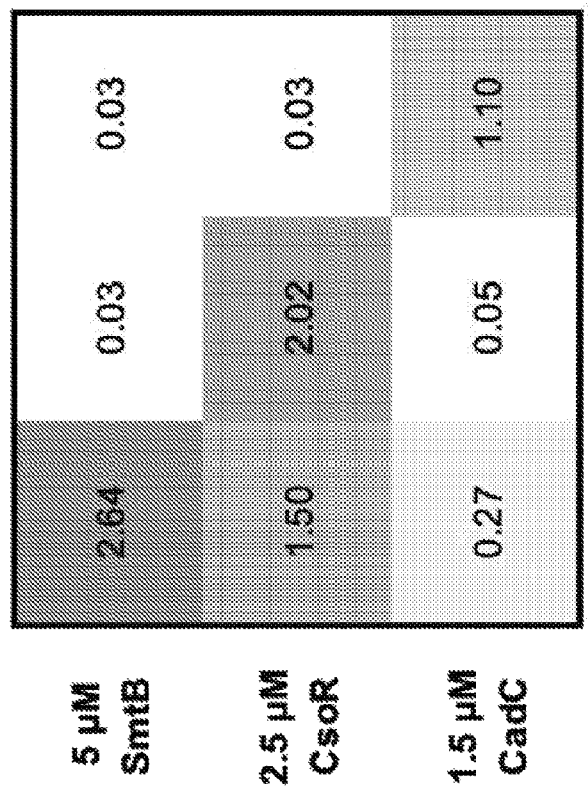
FIG. 25. Demonstration that crosstalk between sensors can be reduced using a kleptamer when implemented as a Ligand 1 NIMPLY Ligand 2 (Ligand 1 AND NOT Ligand 2) logic gate. Each reaction has 0.5 pmol of 3WJdB template and 200 pmol of CsoR. In addition to these components, the NIMPLY condition has 3 pmol of KB2 template and 200 pmol of SmtB.
Figure 25:
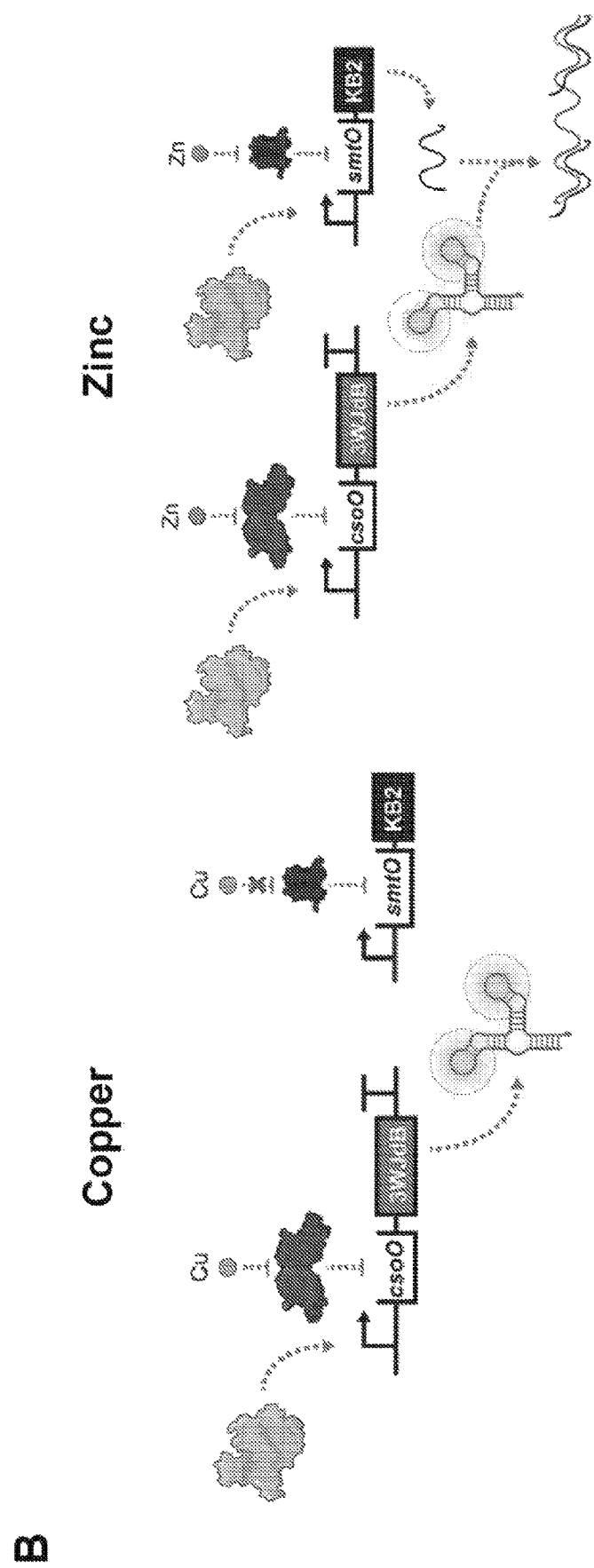
Figure 25:
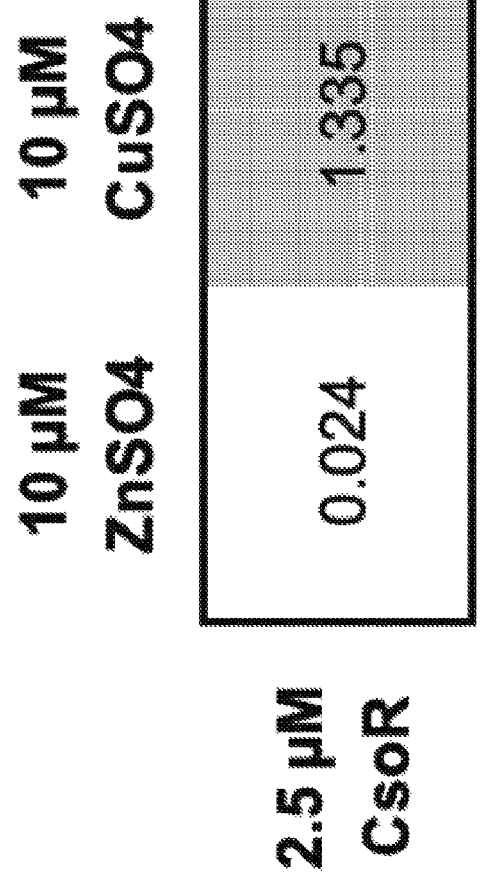
Figure 25:
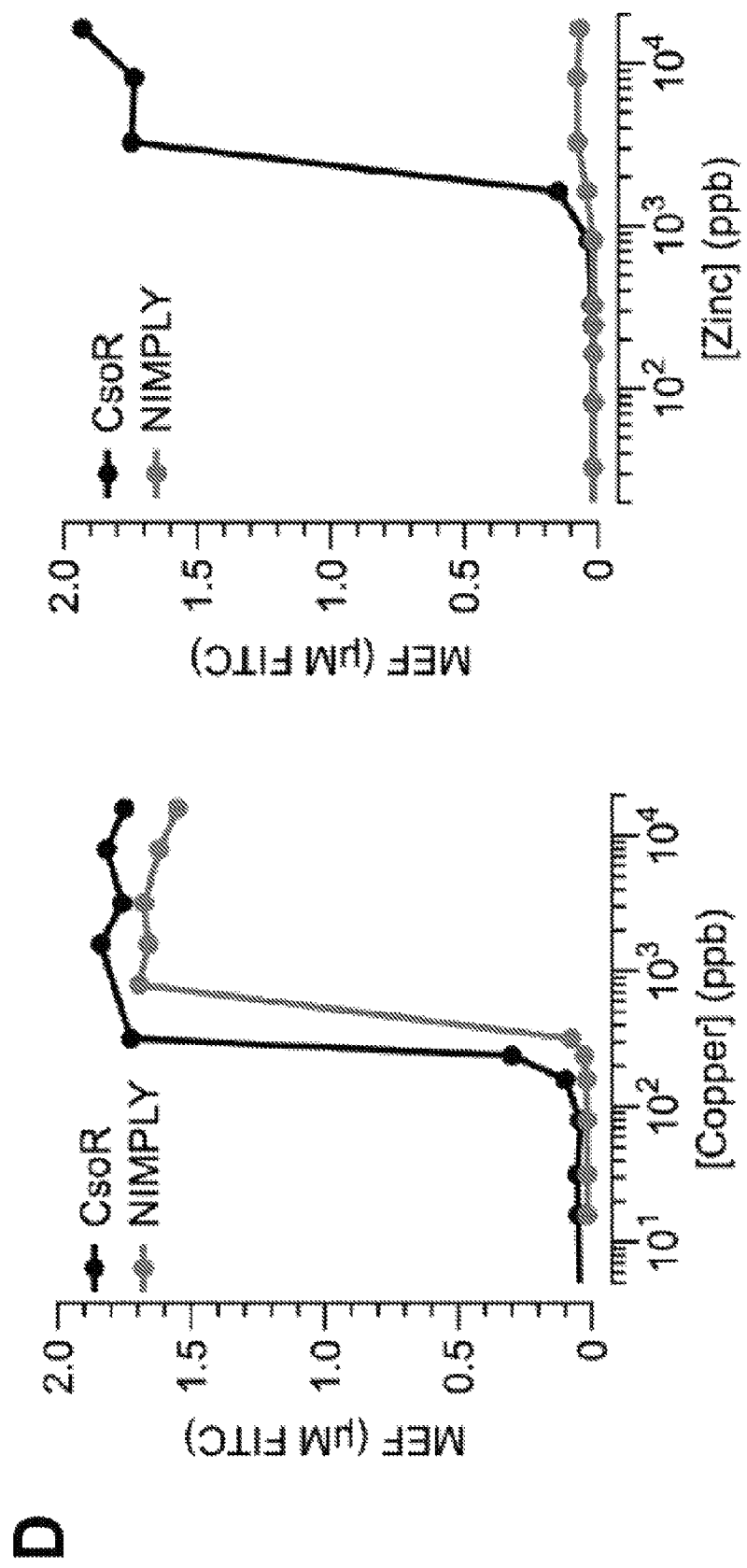

When a representative transcription factor from each family of ligands (TetR, MphR, SAR2349, and CsoR) was tested with representative ligands from each family (tetracycline, erythromycin, salicylate, and copper), we found strong signals from cognate ligands with minimal crosstalk (FIG. 24). However, when metal transcription factors are tested for their reactivities against metals other than their cognate one, we found that the copper sensor, CsoR, can respond to copper as well as zinc (FIG. 25A). In order to fix this crosstalk of CsoR, we built a copper NIMPLY zinc logic gate (copper AND NOT zinc) using a kleptamer regulated by the zinc sensor, SmtB (FIG. 25B). In this circuit, the copper sensor controls the 3WJdB output, while the zinc sensor controls the kleptamer output. Since the zinc sensor, SmtB, is specific to zinc only, when copper is present, there is no expression of kleptamer, allowing the 3WJdB aptamer produced by the copper-induced CsoR to fluoresce. However, when zinc is present, both the 3WJdB and the kleptamer molecules are expressed, and the kleptamer output is able to sequester 3WJdB molecules away from the dye, shutting off the signal. When implemented, this circuit was able to fix the crosstalk not only at a single concentration of zinc (FIG. 25C), but also across a wide range of zinc concentrations (FIG. 25D).

Figure 26:
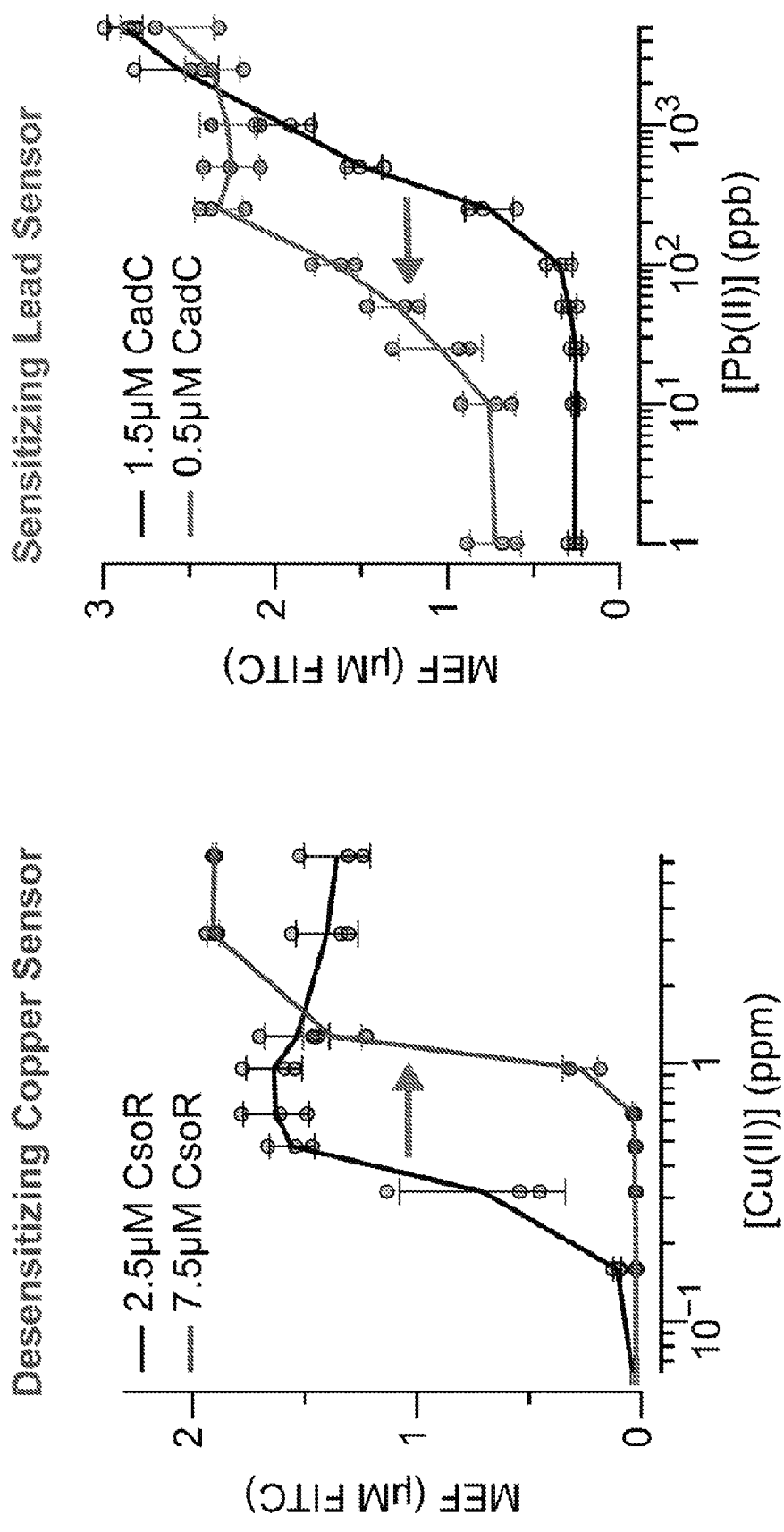
FIG. 26. Demonstration that the sensitivities of a ROSA-LIND sensor can be tuned by adjusting the amount of transcription factors. Panel a: Each reaction has 0.5 pmol of 3WJdB template. Panel b: 1.5 μM condition has 0.5 pmol of 3WJdB template, and 0.5 μM condition has 0.2 pmol of 3WJdB template.

Next, we sought to tune the sensitivity of the copper sensor to meet the EPA regulated limit of copper in drinking water (1.3 ppm). Without any tuning, the sensor detects 0.3 ppm of copper and above (FIG. 26a). To desensitize the sensor to respond near the EPA regulated limit of copper, we reasoned that excess CsoR could be added to the reactions to act as a copper chelator. As expected, when CsoR tetramer concentration was increased from 2.5 μM to 7.5 μM, the sensitivity of the copper sensor was shifted from hundreds of ppb to 1 ppm (FIG. 26a). To further implement this strategy of tuning the amount of transcription factors to shift the sensitivity of a sensor, we determined if the lead sensor can be sensitized by decreasing the amount of CadC dimer. When the concentration was decreased from 1.5 μM to 0.5

µM of CadC, we were able to shift the dose response curve to be more sensitive in order to detect tens of ppb of lead (FIG. 26b). However, this strategy also increased the expression of 3WJdB in the absence any lead.

Figure 27:
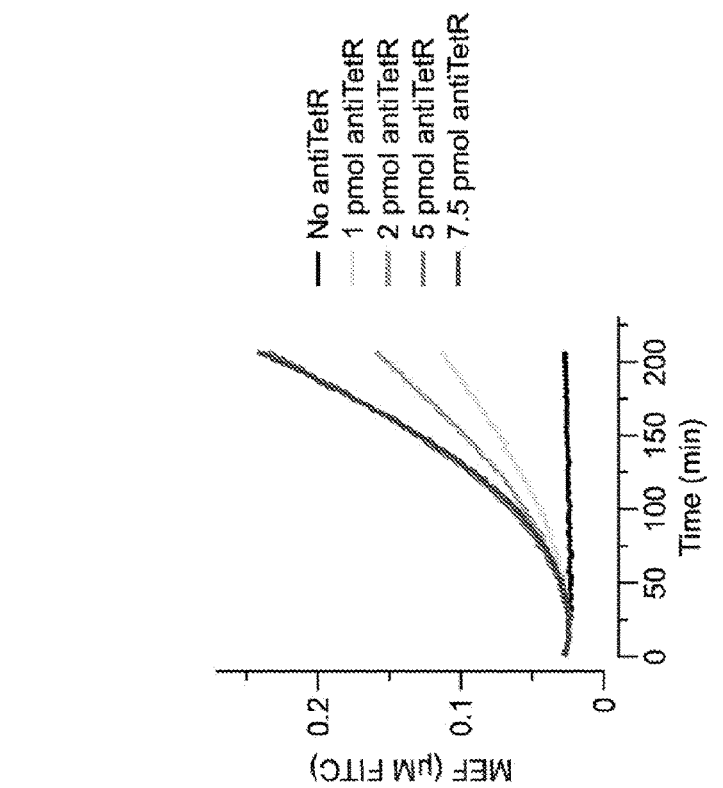
FIG. 27. Demonstration that TetR-binding RNA aptamer (antiTetR) can be used to de-repress TetR-regulated 3WJdB. Each reaction has 0.5 pmol of 3WJdB template and 50 pmol of TetR.
Figure 27:
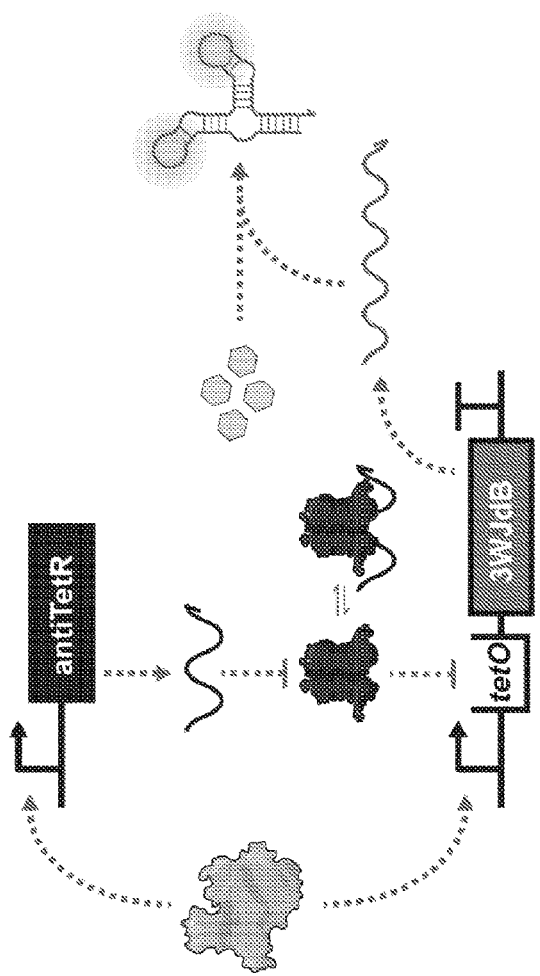
Figure 28:
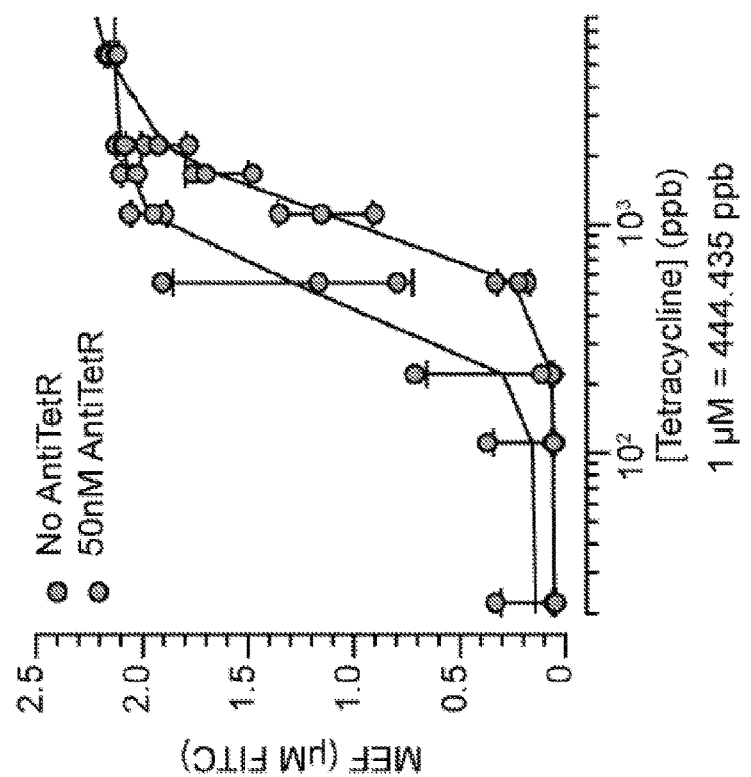
FIG. 28. Demonstration that antiTetR can be used to sensitize TetR-regulated sensors. Each reaction has 0.5 pmol of 3WJdB template and 50 pmol of TetR.
Figure 28:
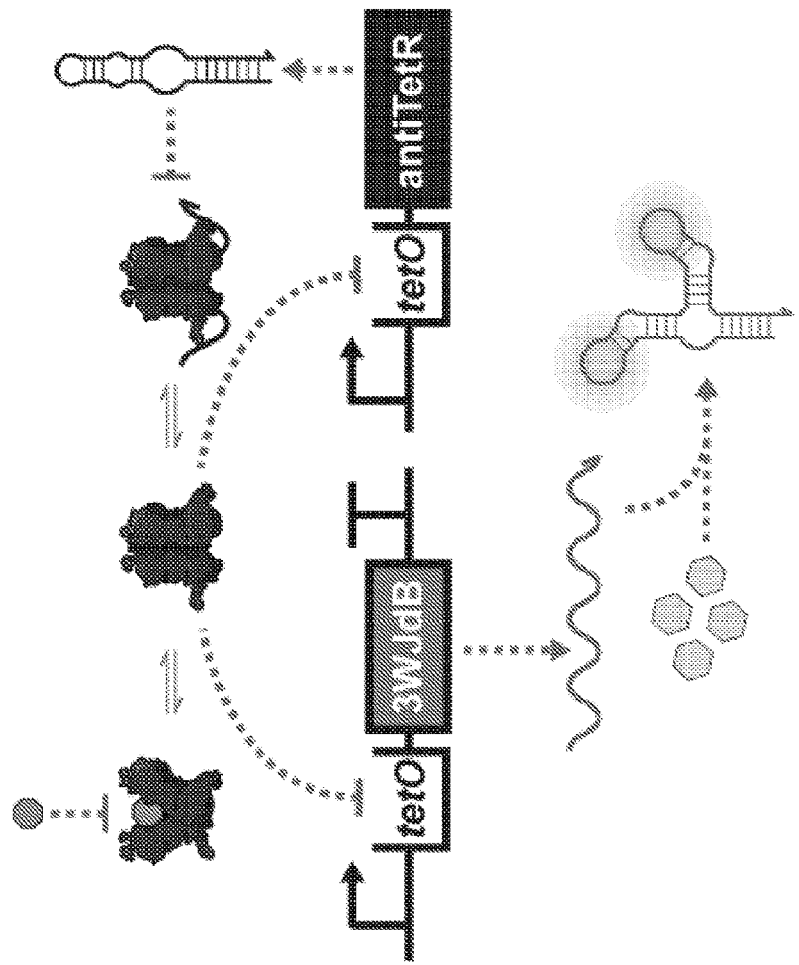

To address the issue of sensitization strategy discussed above, we sought to implement a different method to increase the sensitivity of a sensor. As a proof of concept, we tested this new sensitization method using an antibiotic sensor to meet the threshold concentrations of antibiotics typically found in environment. The new strategy utilizes a TetR-binding RNA aptamer called "antiTetR," which de-represses TetR from its cognate operator site tetO.[37] When the T7 RNAP driven antiTetR DNA template was included in the TetR-regulated 3WJdB transcription reaction, TetR was de-repressed without any of its cognate ligand present (FIG. 27). Taking advantage of this feature of antiTetR, we implemented a feedback loop that can amplify the expression of 3WJdB at a low concentration of tetracyclines. To do so, we included the DNA template of antiTetR that is regulated by TetR by including the tetO sequence upstream of the antiTetR sequence. In this feedback loop, TetR regulates the expression of both 3WJdB and antiTetR. Once a small amount of its cognate ligand such as tetracycline is present, it de-represses TetR and initiates the expression of 3WJdB as well as antiTetR. Once transcribed, antiTetR is then able to further de-repress any TetR that is blocking the transcription of 3WJdB. With this circuit, we were able to improve the sensitivity of a tetracycline sensor down to hundreds of ppb (FIG. 28).

These results demonstrate that RNA genetic circuits can be used not only to fix the crosstalk of a sensor, but also to tune the sensitivity of a sensor.

Figure 29:
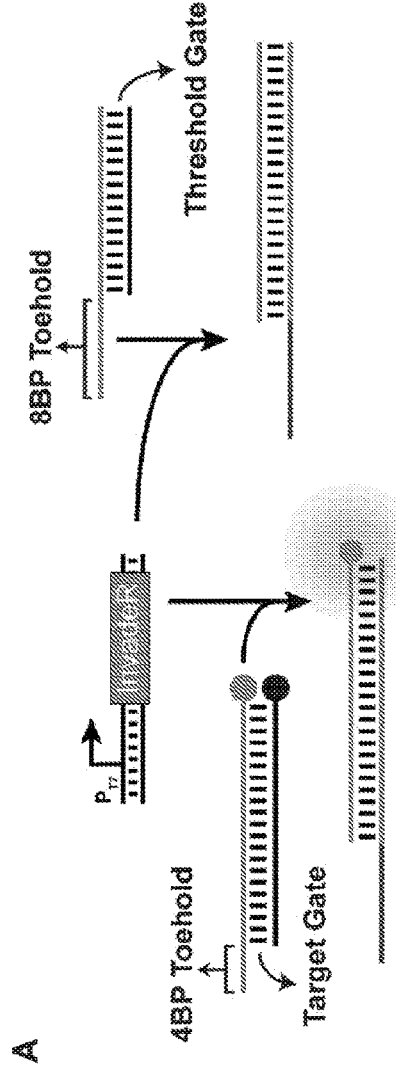
FIG. 29. Demonstration that RNA genetic circuitry can be used to determine the threshold amount of the output RNA needed to generate signal. Panel A: Rate of 4BP Strand Displacement: $5.1 \times 10^4$ 1/M-sec; Rate of 8BP Strand Displacement: $3 \times 10^6$ 1/M-sec. Panel B: Simulations of the schematic in panel A. Panel C: Each reaction has 1 pmol of 3WJdB template and 100 pmol of the target gate.
Figure 29:
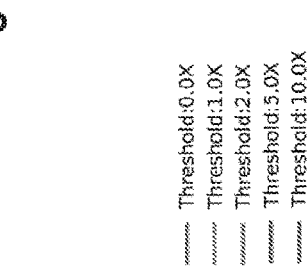
Figure 29:
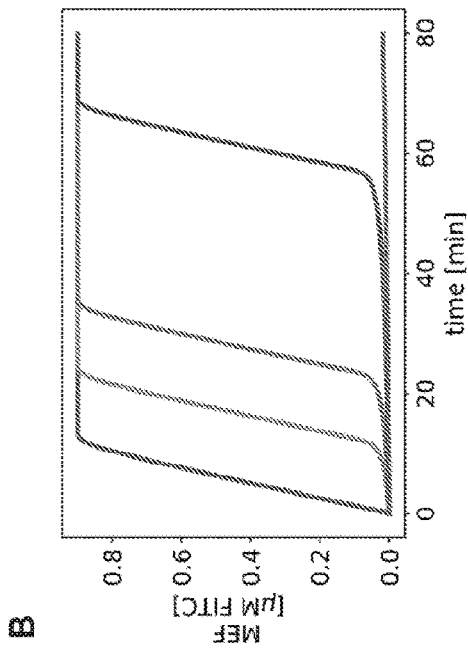

To further improve on the InvadeR platform, we hypothesize that by shortening the toehold length of the output gate, we can kinetically favor the strand displacement reaction of the threshold gate. This would prevent simultaneous strand displacement reactions of both the output and threshold gates, and only after all of the threshold gates have been consumed by InvadeR, InvadeR will strand-displace the output gate to generate fluorescent signal. Simulations of this genetic program show that the output gate with a 4-nucleotide toehold result in time delay of fluorescence-activation when the threshold gate with a 8-nucleotide toehold is present (FIG. 29). Furthermore, different analyte concentrations resulted in different time points at which the fluorescent output becomes visible when the threshold was present (FIG. 29). Thus, the quantification of the input concentration of analyte is communicated via the different times required to achieve an output signal—lower concentrations activate the signal after a longer period of time. Alternatively, this finding enables us to construct a panel of biosensors, each containing a different threshold gate concentration. By visualizing which tubes turn on at a pre-specified time point, we can quantify the input concentration of analyte.

This result demonstrates that genetic circuits such as the threshold gate can be implemented to modulate the fluorescent output in response to analyte concentrations, enabling us to quantify the analyte present in each sample.

Figure 30:
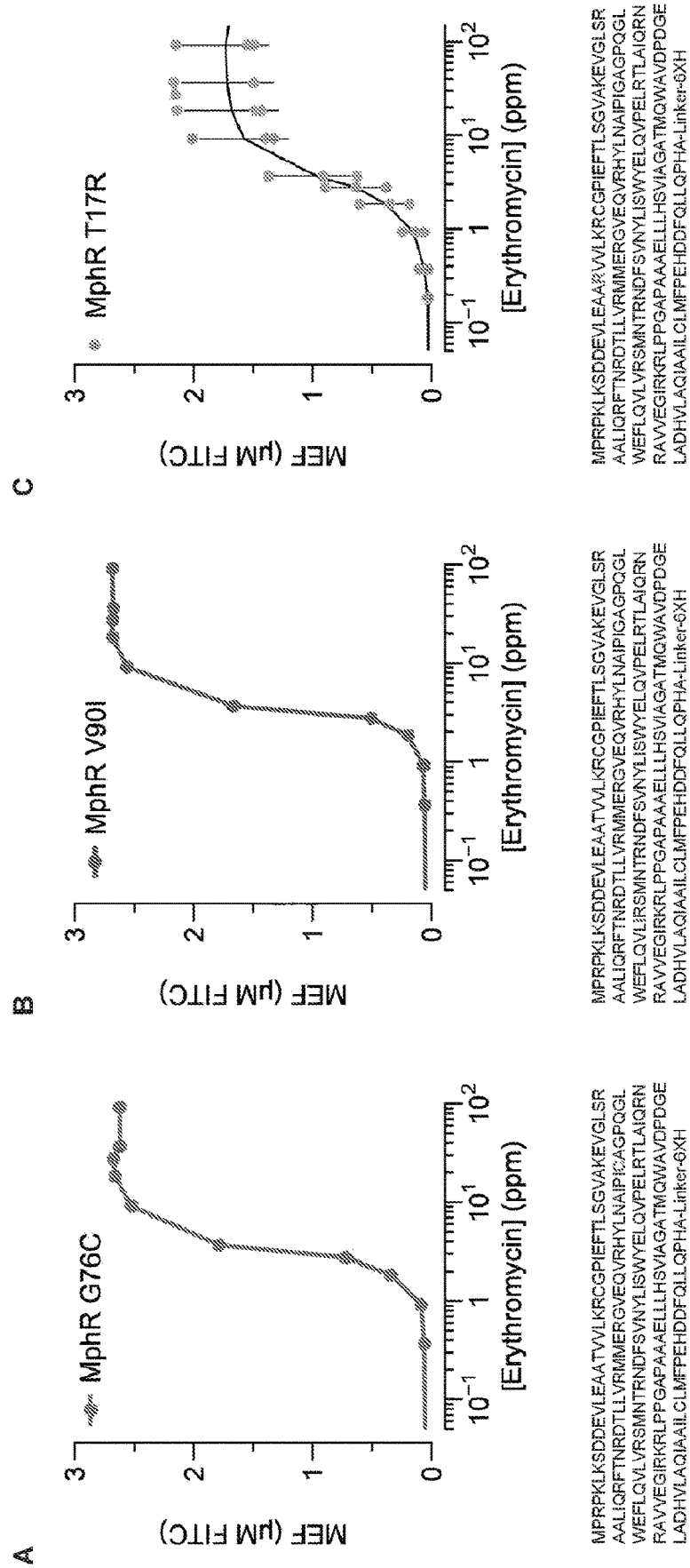
FIG. 30. In vitro transcriptions of fluorescence-activating aptamer (3WJdB) can be regulated with engineered transcription factors. Each reaction has 0.5 pmol of transcription template. The concentrations of transcription factors in each panel are 25 pmol in panel A and B, and 10 pmol in panel C. The three engineered transcription factors used are MphR G76C (panel A; SEQ ID NO: 13), MphR V90I (panel B; SEQ ID NO: 14), and MphR T17R (panel C; SEQ ID NO: 15).

Finally, we sought to implement an engineered transcription factor in the RIViTS platform. To demonstrate this, we tested three different MphR mutants, the macrolide sensor. (See FIG. 30). Each mutant has a single amino acid change that is reported to have altered sensitivities to erythromycin when compared to the wildtype MphR. When tested in RIViTS, all three engineered transcription factors resulted in expected dose-response curves to erythromycin.

Materials and Methods

DNA Transcription Templates. Oligonucleotides for cloning, amplification, and transcription were ordered from Integrated DNA Technologies and resuspended in $H_2O$ at 100 µM. For unregulated transcription of the 3WJdB aptamer, the pUC19-T7-3WJdB-T plasmid (Addgene plasmid #87308) was used.[19] Templates for regulated transcription of the 3WJdB aptamer were cloned into pUC19 plasmids by Gibson assembly. Assembled plasmids were heat-shock transformed into NEB Turbo Competent E. coli cells (New England Biolabs) and clonally isolated by streaking onto antibiotic-selective LB-agar plates grown overnight at 37° C. Plasmids were then purified using a QIAprep miniprep kit (Qiagen) following the manufacturer's protocol and verified by Sanger sequencing at Quintara Biosciences.

Linear DNA transcription templates were prepared by PCR amplification of sequence-verified plasmids. A forward primer annealing upstream of the promoter site and a reverse primer annealing to the 3' end of the terminator or the 3' end of the reporter RNA were used for PCR amplification. Phusion DNA polymerase (New England Biolabs) was used for PCR amplification following the manufacturers protocol. PCR products were purified using a PCR cleanup kit (Qiagen) and eluted in $H_2O$. A single band corresponding to the length of the amplified DNA transcription template was confirmed by running the purified PCR product on a TAE-agarose gel. Purified transcription templates were quantified for concentration using a Qubit dsDNA broad-range assay kit and Qubit 3.0 (Thermo Scientific), and stored at −20° C. until use.

For transcriptions involving the KB2 kleptamer, DNA templates were prepared by thermal annealing of two complementary oligos. In short, an equimolar amount of sense and antisense strands were incubated in water and heated to 95° C. for 3 minutes before slow-cooling (0.1° C./s) to room temperature.

Expression and Purification of Allosteric Transcription Factors. Oligonucleotides and gene fragments for cloning of ATFs were ordered from either Integrated DNA Technologies or Twist Biosciences. DNA encoding ATFs were codon optimized for E. coli and were cloned into pET28c plasmids by Gibson assembly to generate either C- or N-terminus 6×His tagged proteins. Assembled plasmids were heat-shock transformed into NEB Turbo Competent E. coli cells (New England Biolabs) and clonally isolated by streaking onto antibiotic-selective LB-agar plates grown overnight at 37° C. Plasmids were then purified using a QIAprep miniprep kit (Qiagen) and verified by Sanger sequencing at Quintara Biosciences.

Plasmids for expression of ATFs were heat-shock transformed into Rosetta 2(DE3)pLysS competent cells (Novagen) and clonally isolated by streaking onto antibiotic-selective LB-agar plates. A clonal isolate was then used to seed a 10 mL overnight culture (grown at 37° C. with 250 RPM shaking) in LB media with antibiotics. The following morning, overnight cultures were diluted 1:100 into expression cultures of 1-2 L and incubated at 37° C. with 250 RPM shaking. Overexpression was induced with the addition of 0.1-1 mM IPTG when optical density of the culture at 600 nm reached 0.5-1.0. Following a 3- to 4-hour outgrowth of the cultures, cells were pelleted by centrifugation at 12,000×g and spent media was removed. Pelleted cells were stored at −80° C. until further use.

Purification of ATFs was performed by resuspending cell pellets in sonication buffer (25 mM Tris-HCl pH 8, 500 mM NaCl, 1 mM TCEP) supplemented with protease inhibitors (Roche cOmplete EDTA-free). Lysis was performed by sonicating three times on ice in 30 second intervals with 2 minutes of rest in between. Lysates were then spun at 13,000×g at 4° C. for 15-30 minutes to pellet cellular debris. Supernatants were collected by careful decanting and then filtered through a 0.45 µM PES filter. Clarified cell lysates were then subject to affinity chromatography on Ni-NTA resin (Qiagen) to capture the 6×His-tagged proteins and a subset of the proteins were additionally subject to size-exclusion chromatography using a HiLoad 26/600 Superdex 200 pg column (GE Healthcare). Eluted peak fractions were collected and then concentrated and buffer exchanged into (50% glycerol v/v, 25 mM Tris-HCl pH 8.0, 100 mM NaCl, 1 mM TCEP) using an Amicon Ultra centrifugal filter units (Millipore Sigma). Proteins were quantified using a Qubit protein assay and Qubit 3.0 (Thermo Scientific). Purity and expected size of each purified ATF were confirmed with SDS-PAGE.

Purified AdcR was a gift of the Giedroc Lab (Indiana University Bloomington).

In Vitro Transcription. DFHBI-1T was purchased from either Lucerna or Tocris Bioscience and resuspended in DMSO at 40 mM. 45 nmol of DFHBI-1T was used in each transcription reaction involving the 3WJdB aptamer. Data from FIG. 1 was generated using a HiScribe T7 Quick High Yield RNA Synthesis Kit from New England BioLabs following the manufacturer's protocol and using 1 µg of template DNA (~5.2 pmol). All other T7 RNA polymerase transcriptions contained T7 transcription buffer (40 mM Tris-HCl pH 8.0, 20 mM NaCl, 10 mM DTT, 8 mM MgCl2, 2 mM spermidine), 8 mM NTPs, and 2 µL T7 RNA polymerase. Amount of template, inducer, and transcription factor are noted below each figure. T3 and SP6 RNA polymerase were purchased from New England BioLabs, and transcriptions using those polymerases were performed according to the manufacturers protocol. All transcriptions were performed at 37° C. and polymerase was added immediately before measurement.

Oligos for the InvadeR system were purchased from Integrated DNA Technologies and resuspended in TE buffer (10 mM Tris-HCl pH 8.0, 1 mM EDTA). The reporter strand was synthesized with a 3' 6-FAM (fluorescein) fluorophore modification and the quencher strand was synthesized with a 5' Iowa Black FQ quencher modification and HPLC purified. The DNA output gate was created by annealing 100 pmol of reporter and 200 pmol of quencher, heating to 95° C. for 3 minutes, and slow-cooling (0.1° C./s) to room temperature.

Reactions were monitored in real time by measuring on a BioTek Synergy H1 plate reader set to incubate at 37° C. For the 3WJdB output, an excitation wavelength of 472 nm and emission wavelength of 507 nm was used with measurements every 3 minutes. For the InvadeR system, excitation and emission wavelengths were set at 495 nm and 520 nm respectively and measurements were taken every minute.

The tetracycline and macrolide antibiotics were purchased from Gold Biotechnology, and benzalkonium chloride, salicylate and zinc (II) sulfate were purchased from Sigma. Ligands were prepared fresh for every measurement by weighing an appropriate amount and dissolving in an appropriate solvent ($H_2O$, DMSO, or ethanol).

REFERENCES

1. Fernandez-Lopez, R., Ruiz, R., la Cruz, de, F. & Moncalián, G. Transcription factor-based biosensors enlightened by the analyte. 6, 1-21 (2015).
2. Takahashi, M. K. et al. Characterizing and prototyping genetic networks with cell-free transcription-translation reactions. Methods 86, 60-72 (2015).
3. Grate, D. & Wilson, C. Laser-mediated, site-specific inactivation of RNA transcripts. Proc. Natl. Acad. Sci. U.S.A. 96, 6131-6136 (1999).
4. Babendure, J. R., Adams, S. R. & Tsien, R. Y. Aptamers switch on fluorescence of triphenylmethane dyes. J. Am. Chem. Soc. 125, 14716-14717 (2003).
5. Dolgosheina, E. V. et al. RNA mango aptamer-fluorophore: a bright, high-affinity complex for RNA labeling and tracking. ACS Chem Biol 9, 2412-2420 (2014).
6. Paige, J. S., Wu, K. Y. & Jaffrey, S. R. RNA mimics of green fluorescent protein. 333, 642-646 (2011).
7. Strack, R. L., Disney, M. D. & Jaffrey, S. R. A superfolding Spinach2 reveals the dynamic nature of trinucleotide repeat-containing RNA. Nature Methods 10, 1219-1224 (2013).
8. Filonov, G. S., Moon, J. D., Svensen, N. & Jaffrey, S. R. Broccoli: rapid selection of an RNA mimic of green fluorescent protein by fluorescence-based selection and directed evolution. J. Am. Chem. Soc. 136, 16299-16308 (2014).
9. Song, W. et al. Imaging RNA polymerase III transcription using a photostable RNA-fluorophore complex. Nat Chem Bio 13, 1187-1194 (2017).
10. Paige, J. S., Nguyen-Duc, T., Song, W. & Jaffrey, S. R. Fluorescence imaging of cellular metabolites with RNA. Science 335, 1194-1194 (2012).
11. Kellenberger, C. A., Wilson, S. C., Sales-Lee, J. & Hammond, M. C. RNA-Based Fluorescent Biosensors for Live Cell Imaging of Second Messengers Cyclic di-GMP and Cyclic AMP-GMP. J. Am. Chem. Soc. 135, 4906-4909 (2013).
12. Höfer, K., Langejürgen, L. V. & Jäschke, A. Universal aptamer-based real-time monitoring of enzymatic RNA synthesis. J. Am. Chem. Soc. 135, 13692-13694 (2013).
13. Autour, A., Westhof, E. & Ryckelynck, M. iSpinach: a fluorogenic RNA aptamer optimized for in vitro applications. Nucleic Acids Res. 44, 2491-2500 (2016).
14. Heili, J. M. et al. Real-Time Visualization of in Vitro Transcription of a Fluorescent RNA Aptamer: An Experiment for the Upper-Division Undergraduate or First-Year Graduate Laboratory. Journal of Chemical Education 95, 1867-1871 (2018).
15. Sajja, S., Chandler, M., Striplin, C. D. & Afonin, K. A. Activation of Split RNA Aptamers: Experiments Demonstrating the Enzymatic Synthesis of Short RNAs and Their Assembly As Observed by Fluorescent Response. Journal of Chemical Education 95, 1861-1866 (2018).
16. Han, K. Y., Leslie, B. J., Fei, J., Zhang, J. & Ha, T. Understanding the Photophysics of the Spinach-DFHBI RNA Aptamer-Fluorogen Complex To Improve Live-Cell RNA Imaging. J. Am. Chem. Soc. 135, 19033-19038 (2013).
17. Srinivas, N. et al. On the biophysics and kinetics of toehold-mediated DNA strand displacement. Nucleic Acids Res. 41, 10641-10658 (2013).
18. Zhang, D. Y., Turberfield, A. J., Yurke, B. & Winfree, E. Engineering entropy-driven reactions and networks catalyzed by DNA. Science 318, 1121-1125 (2007).
19. Alam, K. K., Tawiah, K. D., Lichte, M. F., Porciani, D. & Burke, D. H. A Fluorescent Split Aptamer for Visualizing RNA-RNA Assembly In Vivo. ACS Synth. Biol. 6, 1710-1721 (2017).

20. Song, W., Strack, R. L., Svensen, N. & Jaffrey, S. R. Plug-and-play fluorophores extend the spectral properties of Spinach. J. Am. Chem. Soc. 136, 1198-1201 (2014).
21. Bhadra, S. & Ellington, A. D. Design and application of cotranscriptional non-enzymatic RNA circuits and signal transducers. Nucleic Acids Res. 42, e58-e58 (2014).
22. Zhang, D. Y. & Seelig, G. Dynamic DNA nanotechnology using strand-displacement reactions. Nature Chemistry 3, 103-113 (2011).
23. Schaffter, S. W. et al. T7 RNA polymerase non-specifically transcribes and induces disassembly of DNA nanostructures. Nucleic Acids Res. 46, 5332-5343 (2018).
24. Yin, Y. W. & Steitz, T. A. Structural basis for the transition from initiation to elongation transcription in T7 RNA polymerase. Science 298, 1387-1395 (2002).
25. Saenger, W., Orth, P., Kisker, C., Hillen, W. & Hinrichs, W. The Tetracycline Repressor—A Paradigm for a Biological Switch. Angew Chem Int Ed Engl 39, 2042-2052 (2000).
26. Noguchi, N., Takada, K., Katayama, J., of, A. E. J.2000. Regulation of Transcription of the mph(A) Gene for Macrolide 2′-Phosphotransferase I in *Escherichia coli*: Characterization of the Regulatory Gene mphR(A). Am Soc Microbiol doi:10.1128/JB.182.18.5052-5058.2000
27. Kasey, C. M., Zerrad, M., Li, Y., Cropp, T. A. & Williams, G. J. Development of Transcription Factor-Based Designer Macrolide Biosensors for Metabolic Engineering and Synthetic Biology. ACS Synth. Biol. 7, 227-239 (2018).
28. Weber, W. et al. Macrolide-based transgene control in mammalian cells and mice. Nat. Biotechnol. 20, 901-907 (2002).
29. Grkovic, S., Brown, M. H., Roberts, N. J., Paulsen, I. T. & Skurray, R. A. QacR is a repressor protein that regulates expression of the *Staphylococcus aureus* multidrug efflux pump QacA. J. Biol. Chem. 273, 18665-18673 (1998).
30. Wang, W. et al. Development of a Synthetic Oxytetracycline-Inducible Expression System for Streptomycetes Using de Novo Characterized Genetic Parts. ACS Synth. Biol. 5, 765-773 (2016).
31. Zhu, T., Cheng, X., Liu, Y., Deng, Z. & You, D. Deciphering and engineering of the final step halogenase for improved chlortetracycline biosynthesis in industrial *Streptomyces aureofaciens*. Metabolic Engineering 19, 69-78 (2013).
32. Chang, Y. M., Chen, C. K. M., Ko, T. P., Chang-Chien, M. W. & Wang, A. H. J. Structural analysis of the antibiotic-recognition mechanism of MarR proteins. Acta Crystallogr. D Biol. Crystallogr. 69, 1138-1149 (2013).
33. Yoshida, M., Hiromoto, T., Hosokawa, K., Yamaguchi, H. & Fujiwara, S. Ligand specificity of MobR, a transcriptional regulator for the 3-hydroxybenzoate hydroxylase gene of *Comamonas testosteroni* KH122-3s. Biochem. Biophys. Res. Commun. 362, 275-280 (2007).
34. Busenlehner, L. S., Pennella, M. A. & Giedroc, D. P. The SmtB/ArsR family of metalloregulatory transcriptional repressors: structural insights into prokaryotic metal resistance. FEMS Microbiol Rev 27, 131-143 (2003).
35. Lloyd, J. et al. Dynamic Control of Aptamer-Ligand Activity Using Strand Displacement Reactions. ACS Synth. Biol. 7, 30-37 (2018).
36. Reyes-Caballero, H. et al. The Metalloregulatory Zinc Site in *Streptococcus pneumoniae* AdcR, a Zinc-activated MarR Family Repressor. J. Mol. Biol. 403, 197-216 (2010).

In the foregoing description, it will be readily apparent to one skilled in the art that varying substitutions and modifications may be made to the invention disclosed herein without departing from the scope and spirit of the invention. The invention illustratively described herein suitably may be practiced in the absence of any element or elements, limitation or limitations which is not specifically disclosed herein. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention. Thus, it should be understood that although the present invention has been illustrated by specific embodiments and optional features, modification and/or variation of the concepts herein disclosed may be resorted to by those skilled in the art, and that such modifications and variations are considered to be within the scope of this invention.

Citations to a number of patent and non-patent references may be made herein. The cited references are incorporated by reference herein in their entireties. In the event that there is an inconsistency between a definition of a term in the specification as compared to a definition of the term in a cited reference, the term should be interpreted based on the definition in the specification.

We claim:

1. A composition, system, or kit for detecting an analyte comprising as components:
   (a) an RNA polymerase;
   (b) an allosteric transcription factor (ATF), wherein the analyte is a ligand to which the ATF binds;
   (c) a reporter molecule comprising an RNA binding site; and
   (d) a first engineered transcription template, the first engineered transcription template comprising a promoter sequence for the RNA polymerase and an operator sequence for the ATF operably linked to a sequence encoding an RNA,
   wherein the ATF modulates transcription of the encoded RNA when the ATF binds the analyte as a ligand,
   wherein the transcribed RNA generates a detectable signal when bound to the RNA binding site of the reporter molecule, or interferes with a detectable signal, and
   wherein the reporter molecule is a fluorescently labeled double-stranded nucleic acid comprising a fluorophore and a quencher that quenches the fluorophore in the fluorescently labeled double-stranded nucleic acid and the transcribed RNA displaces one of the strands of the fluorescently labeled double-stranded nucleic acid which results in dequenching of the fluorophore to generate the detectable signal.

2. The composition, system, or kit of claim 1, further comprising a second engineered transcription template, the second engineered transcription template comprising a promoter sequence for the RNA polymerase operably linked to a sequence encoding a second RNA, wherein the second RNA binds to the RNA binding site of the reporter molecule which second RNA binding generates a detectable signal, and the RNA transcribed from the first engineered transcription template, namely the first RNA, interacts with the second RNA and interferes with the detectable signal generated by the second RNA binding to the reporter molecule.

3. The composition, system, or kit of claim 1, wherein the RNA polymerase is selected from T7 RNA polymerase, T3 RNA polymerase, SP6 RNA polymerase, and Syn5 RNA polymerase or the RNA polymerase is an engineered polymerase.

4. The composition, system, or kit of claim 1, wherein the RNA polymerase is an engineered RNA polymerase.

5. The composition, system, or kit of claim 1, wherein the ATF represses, blocks, or inhibits transcription from the engineered transcription template when the ATF binds the operator.

6. The composition, system, or kit of claim 1, wherein the ATF activates transcription from the engineered transcription template when the ATF binds the operator.

7. The composition, system, or kit of claim 1, wherein the system is configured such that at least one of the following conditions is met:
   (i) in the absence of the analyte as a ligand the ATF binds to the operator sequence;
   (ii) in the presence of the analyte as a ligand the ATF does not bind to the operator or binds to the operator at a lower affinity than in the absence of the analyte as a ligand;
   (iii) in the presence of the analyte as a ligand the ATF binds to the operator sequence; and
   (iv) in the absence of the analyte as a ligand the ATF does not bind to the operator or binds to the operator at a lower affinity than in the presence of the analyte as a ligand.

8. The composition, system, or kit of claim 1, wherein the ATF belongs to the TetR, MarR, or ArsR/SmtB class or family of transcription factors or the ATF is an engineered ATF.

9. The composition, system, or kit of claim 1, wherein the ATF is selected from the group consisting of TetR, MphR, QacR, OtrR, CtcS, SAR2349, MobR, SmtB, CadC, CsoR, AdcR, TtgR, and HucR.

10. The composition, system, or kit of claim 1, wherein the analyte that is a ligand for the ATF is a member of the tetracycline-family of antibiotics.

11. The composition, system, or kit of claim 1, wherein the analyte that is a ligand for the ATF is a member of the macrolide-family of antibiotics.

12. The composition, system, or kit of claim 1, wherein the analyte is a quaternary amine or salt thereof.

13. The composition, system, or kit of claim 1, wherein the analyte is a metal or a cation thereof.

14. The composition, system, or kit of claim 13, wherein the metal or the cation thereof is Zn, Pb, Cu, Cd, Ni, As, or Mn.

15. The composition, system, or kit of claim 1, wherein the analyte is selected from salicylate, 3-hydroxy benzoic acid, naringenin, and uric acid.

16. The composition, system, or kit of claim 1, wherein the transcribed RNA is a fluorescence-activating aptamer.

17. The composition, system, or kit of claim 1, wherein the transcribed RNA is a fluorescence-activating aptamer selected from the group consisting of Malachite Green aptamer, Mango aptamer, and the Spinach/Broccoli family of aptamers.

18. The composition, system, or kit of claim 16, wherein the system further comprises (e) a dye, wherein the aptamer binds and activates the fluorescence of the dye to generate the detectable signal.

19. The composition, system, or kit of claim 18, wherein the dye is selected from the group consisting of (5Z)-5-[(3,5-Difluoro-4-hydroxyphenyl) methylene]-3,5-dihydro-2,3-dimethyl-4H-Imidazol-4-one, (Z)-4-(3,5-Difluoro-4-hydroxybenzylidene)-1,2-dimethyl-1H-imidazol-5 (4H)-one (DFHBI), (5Z)-5-[(3,5-Difluoro-4-hydroxyphenyl) methylene]-3,5-dihydro-2-methyl-3-(2,2,2-trifluoroethyl)-4H-imidazol-4-one (DFHBI-1T), 3,5-difluoro-4-hydroxybenzylidene imidazolinone-2-oxime (DFHO), thiazole orange dyes; and Malachite Green.

20. The composition, system, or kit of claim 16, wherein the aptamer is a three-way junction dimeric Broccoli (3WJdB) aptamer.

21. The composition, system, or kit of claim 1, wherein the reporter molecule is a fluorescently labeled double-stranded DNA molecule comprising a top strand having a fluorophore conjugated at its 3'-end and a bottom strand having a quencher conjugated at its 5' end that quenches the fluorophore in the fluorescently labeled double-stranded DNA molecule and the transcribed RNA displaces the bottom strand of the fluorescently labeled double-stranded DNA molecule which results in dequenching of the fluorophore to generate the detectable signal.

22. The composition, system, or kit of claim 21, wherein the top strand is longer than the bottom strand and wherein the transcribed RNA comprises a sequence that is complementary to the full length of the top strand.

23. The composition, system, or kit of claim 1, wherein the system further comprises a non-labeled double-stranded DNA molecule comprising a top strand that comprises a nucleotide sequence that is identical to the nucleotide sequence of the top strand of the labeled double-stranded DNA molecule.

24. The composition, system, or kit of claim 23, wherein the top strand of the non-labeled double-stranded DNA molecule is longer than the bottom strand of the non-labeled double-stranded DNA molecule.

25. The composition, system, or kit of claim 23, wherein the bottom strand of the non-labeled double-stranded DNA molecule is shorter in length than the length of the bottom strand of the fluorescently labeled double-stranded DNA molecule.

26. The composition, system, or kit of claim 1 further comprising (e) one or more components for preparing a reaction mixture for RNA transcription.

27. The composition, system, or kit of claim 1, wherein the components are mixed and form an aqueous solution for performing RNA transcription.

28. The composition, system, or kit of claim 1, wherein the components are mixed and form a dried mixture which may be reconstituted to form a reaction mixture for performing RNA transcription.

29. A composition, system, or kit for detecting one or more analytes, the system comprising as components:
   (a) one or more RNA polymerases;
   (b)(i) a first allosteric transcription factor (ATF), wherein one or more of the analytes is a ligand to which the first ATF binds;
   (b)(ii) a second allosteric transcription factor (ATF) which may be the same as the first ATF or different than the first ATF, wherein one or more of the analytes is a ligand to which the second ATF binds;
   (c)(i) a first engineered transcription template, the first engineered transcription template comprising a promoter sequence for the RNA polymerase and an operator sequence to which the first ATF is capable of binding operably linked to a sequence encoding a first RNA, wherein the first ATF modulates transcription of the encoded first RNA when the first ATF binds the first analyte as a ligand;
   (c)(ii) a second engineered transcription template, the second engineered transcription template comprising a promoter sequence for the RNA polymerase and an operator sequence to which the second ATF is capable of binding operably linked to a sequence encoding a second RNA, wherein the second ATF modulates transcription of the encoded second RNA when the second ATF binds the analyte as a ligand; and (d) a reporter molecule comprising an RNA binding site; wherein the first RNA, the second RNA, and the reporter molecule form a complex that generates a detectable signal, or wherein the system is configured such that (i) the first RNA binds to the RNA binding site of the reporter molecule to generate a detectable signal, and (ii) the second RNA binds to the first RNA to inhibit the detectable signal or the second RNA binds to the first ATF to interfere with the first ATF binding to its operator sequence.

30. The composition, system, or kit of claim 29, wherein the first RNA and the second RNA interact to form a fluorescence-activating aptamer.

31. The composition, system, or kit of claim 29, wherein the first RNA and the second RNA are part of a Split-Broccoli aptamer system.

32. A method for detecting an analyte in a sample, the method comprising contacting the sample with the composition, system, or kit of claim 1 and detecting a detectable signal.

* * * * *

SEQUENCE LISTING

```
<160> NUMBER OF SEQ ID NOS: 16

<210> SEQ ID NO 1
<211> LENGTH: 240
<212> TYPE: DNA
<213> ORGANISM: Artificial Sequence
<220> FEATURE:
<223> OTHER INFORMATION: synthetic

<400> SEQUENCE: 1
taatacgact cactatagga ggtccctatc agtgatagag acccacatac tctgatgatc      60
cgagacggtc gggtccagat attcgtatct gtcgagtaga gtgtgggctc ggatcattca     120
tggcaagaga cggtcgggtc cagatattcg tatctgtcga gtagagtgtg ggctcttgcc     180
atgtgtatgt gggtagcata accccttggg gcctctaaac gggtcttgag gggtttttg     240
```

```
<210> SEQ ID NO 2
<211> LENGTH: 62
<212> TYPE: DNA
<213> ORGANISM: Artificial Sequence
<220> FEATURE:
<223> OTHER INFORMATION: synthetic

<400> SEQUENCE: 2
taatacgact cactataggt ccctatcagt gatagagact cgagatactg ttcccgatcc    60
aa                                                                  62

<210> SEQ ID NO 3
<211> LENGTH: 24
<212> TYPE: DNA
<213> ORGANISM: Artificial Sequence
<220> FEATURE:
<223> OTHER INFORMATION: synthetic

<400> SEQUENCE: 3
ttggatcggg aacagtatct cgag                                          24

<210> SEQ ID NO 4
<211> LENGTH: 16
<212> TYPE: DNA
<213> ORGANISM: Artificial Sequence
<220> FEATURE:
<223> OTHER INFORMATION: synthetic

<400> SEQUENCE: 4
ccttgtcata gagctc                                                   16

<210> SEQ ID NO 5
<211> LENGTH: 36
<212> TYPE: DNA
<213> ORGANISM: Artificial Sequence
<220> FEATURE:
<223> OTHER INFORMATION: synthetic

<400> SEQUENCE: 5
taatacgact cactatatcc ctatcagtga tagaga                              36

<210> SEQ ID NO 6
<211> LENGTH: 36
<212> TYPE: DNA
<213> ORGANISM: Artificial Sequence
<220> FEATURE:
<223> OTHER INFORMATION: synthetic

<400> SEQUENCE: 6
aatacgactc actataggtc cctatcagtg atagag                              36

<210> SEQ ID NO 7
<211> LENGTH: 36
<212> TYPE: DNA
<213> ORGANISM: Artificial Sequence
<220> FEATURE:
<223> OTHER INFORMATION: synthetic

<400> SEQUENCE: 7
atacgactca ctatagggat ccctatcagt gataga                              36

<210> SEQ ID NO 8
<211> LENGTH: 36
<212> TYPE: DNA
<213> ORGANISM: Artificial Sequence
<220> FEATURE:
```

-continued

<223> OTHER INFORMATION: synthetic

<400> SEQUENCE: 8
tacgactcac tataggagga tccctatcag tgatag                                36

<210> SEQ ID NO 9
<211> LENGTH: 36
<212> TYPE: DNA
<213> ORGANISM: Artificial Sequence
<220> FEATURE:
<223> OTHER INFORMATION: synthetic

<400> SEQUENCE: 9
acgactcact atagggagac tccctatca gtgata                                 36

<210> SEQ ID NO 10
<211> LENGTH: 36
<212> TYPE: DNA
<213> ORGANISM: Artificial Sequence
<220> FEATURE:
<223> OTHER INFORMATION: synthetic

<400> SEQUENCE: 10
cgactcacta tagggagacc actccctatc agtgat                                36

<210> SEQ ID NO 11
<211> LENGTH: 36
<212> TYPE: DNA
<213> ORGANISM: Artificial Sequence
<220> FEATURE:
<223> OTHER INFORMATION: synthetic

<400> SEQUENCE: 11
gactcactat agggagacca caatccctat cagtga                                36

<210> SEQ ID NO 12
<211> LENGTH: 36
<212> TYPE: DNA
<213> ORGANISM: Artificial Sequence
<220> FEATURE:
<223> OTHER INFORMATION: synthetic

<400> SEQUENCE: 12
actcactata gggagaccac aacgtcccta tcagtg                                36

<210> SEQ ID NO 13
<211> LENGTH: 194
<212> TYPE: PRT
<213> ORGANISM: Artificial Sequence
<220> FEATURE:
<223> OTHER INFORMATION: synthetic

<400> SEQUENCE: 13

Met Pro Arg Pro Lys Leu Lys Ser Asp Asp Glu Val Leu Glu Ala Ala
1               5                   10                  15

Thr Val Val Leu Lys Arg Cys Gly Pro Ile Glu Phe Thr Leu Ser Gly
                20                  25                  30

Val Ala Lys Glu Val Gly Leu Ser Arg Ala Ala Leu Ile Gln Arg Phe
            35                  40                  45

Thr Asn Arg Asp Thr Leu Leu Val Arg Met Met Glu Arg Gly Val Glu
        50                  55                  60

Gln Val Arg His Tyr Leu Asn Ala Ile Pro Ile Cys Ala Gly Pro Gln
65                  70                  75                  80

Gly Leu Trp Glu Phe Leu Gln Val Leu Val Arg Ser Met Asn Thr Arg
                85                  90                  95

Asn Asp Phe Ser Val Asn Tyr Leu Ile Ser Trp Tyr Glu Leu Gln Val
            100                 105                 110

Pro Glu Leu Arg Thr Leu Ala Ile Gln Arg Asn Arg Ala Val Val Glu
            115                 120                 125

Gly Ile Arg Lys Arg Leu Pro Pro Gly Ala Pro Ala Ala Glu Leu
        130                 135                 140

Leu Leu His Ser Val Ile Ala Gly Ala Thr Met Gln Trp Ala Val Asp
145                 150                 155                 160

Pro Asp Gly Glu Leu Ala Asp His Val Leu Ala Gln Ile Ala Ala Ile
            165                 170                 175

Leu Cys Leu Met Phe Pro Glu His Asp Asp Phe Gln Leu Leu Gln Pro
            180                 185                 190

His Ala

<210> SEQ ID NO 14
<211> LENGTH: 194
<212> TYPE: PRT
<213> ORGANISM: Artificial Sequence
<220> FEATURE:
<223> OTHER INFORMATION: synthetic

<400> SEQUENCE: 14

Met Pro Arg Pro Lys Leu Lys Ser Asp Asp Glu Val Leu Glu Ala Ala
1               5                   10                  15

Thr Val Val Leu Lys Arg Cys Gly Pro Ile Glu Phe Thr Leu Ser Gly
            20                  25                  30

Val Ala Lys Glu Val Gly Leu Ser Arg Ala Ala Leu Ile Gln Arg Phe
        35                  40                  45

Thr Asn Arg Asp Thr Leu Leu Val Arg Met Met Glu Arg Gly Val Glu
50                  55                  60

Gln Val Arg His Tyr Leu Asn Ala Ile Pro Ile Gly Ala Gly Pro Gln
65                  70                  75                  80

Gly Leu Trp Glu Phe Leu Gln Val Leu Ile Arg Ser Met Asn Thr Arg
                85                  90                  95

Asn Asp Phe Ser Val Asn Tyr Leu Ile Ser Trp Tyr Glu Leu Gln Val
            100                 105                 110

Pro Glu Leu Arg Thr Leu Ala Ile Gln Arg Asn Arg Ala Val Val Glu
            115                 120                 125

Gly Ile Arg Lys Arg Leu Pro Pro Gly Ala Pro Ala Ala Glu Leu
        130                 135                 140

Leu Leu His Ser Val Ile Ala Gly Ala Thr Met Gln Trp Ala Val Asp
145                 150                 155                 160

Pro Asp Gly Glu Leu Ala Asp His Val Leu Ala Gln Ile Ala Ala Ile
            165                 170                 175

Leu Cys Leu Met Phe Pro Glu His Asp Asp Phe Gln Leu Leu Gln Pro
            180                 185                 190

His Ala

<210> SEQ ID NO 15
<211> LENGTH: 194
<212> TYPE: PRT
<213> ORGANISM: Artificial Sequence
<220> FEATURE:
<223> OTHER INFORMATION: synthetic

```
<400> SEQUENCE: 15

Met Pro Arg Pro Lys Leu Lys Ser Asp Asp Glu Val Leu Glu Ala Ala
1               5                   10                  15

Arg Val Val Leu Lys Arg Cys Gly Pro Ile Glu Phe Thr Leu Ser Gly
                20                  25                  30

Val Ala Lys Glu Val Gly Leu Ser Arg Ala Ala Leu Ile Gln Arg Phe
            35                  40                  45

Thr Asn Arg Asp Thr Leu Leu Val Arg Met Met Glu Arg Gly Val Glu
        50                  55                  60

Gln Val Arg His Tyr Leu Asn Ala Ile Pro Ile Gly Ala Gly Pro Gln
65                  70                  75                  80

Gly Leu Trp Glu Phe Leu Gln Val Leu Val Arg Ser Met Asn Thr Arg
                85                  90                  95

Asn Asp Phe Ser Val Asn Tyr Leu Ile Ser Trp Tyr Glu Leu Gln Val
                100                 105                 110

Pro Glu Leu Arg Thr Leu Ala Ile Gln Arg Asn Arg Ala Val Val Glu
                115                 120                 125

Gly Ile Arg Lys Arg Leu Pro Pro Gly Ala Pro Ala Ala Ala Glu Leu
    130                 135                 140

Leu Leu His Ser Val Ile Ala Gly Ala Thr Met Gln Trp Ala Val Asp
145                 150                 155                 160

Pro Asp Gly Glu Leu Ala Asp His Val Leu Ala Gln Ile Ala Ala Ile
                165                 170                 175

Leu Cys Leu Met Phe Pro Glu His Asp Asp Phe Gln Leu Leu Gln Pro
                180                 185                 190

His Ala

<210> SEQ ID NO 16
<211> LENGTH: 6
<212> TYPE: PRT
<213> ORGANISM: Artificial Sequence
<220> FEATURE:
<223> OTHER INFORMATION: Synthetic- 6XHis Tag

<400> SEQUENCE: 16

His His His His His His
1               5
```